US009951337B2

(12) United States Patent
Brys et al.

(10) Patent No.: US 9,951,337 B2
(45) Date of Patent: Apr. 24, 2018

(54) METHODS AND MEANS FOR TREATMENT OF OSTEOARTHRITIS

(71) Applicant: GALAPAGOS NV, Mechelen (BE)

(72) Inventors: Reginald Christophe Xavier Brys, Mechelen (BE); Luc Nelles, Mechelen (BE); Nick Ernest Rene Vandeghinste, Mechelen (BE); Blandine Mille-Baker, CR Leiden (NL); Michela Angela Tessari, CR Leiden (NL)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 15/014,290

(22) Filed: Feb. 3, 2016

(65) Prior Publication Data

US 2016/0208266 A1 Jul. 21, 2016

Related U.S. Application Data

(62) Division of application No. 14/162,908, filed on Jan. 24, 2014, now abandoned, which is a division of application No. 13/262,634, filed as application No. PCT/EP2010/054412 on Apr. 1, 2010, now Pat. No. 8,663,930.

(60) Provisional application No. 61/211,740, filed on Apr. 1, 2009.

(51) Int. Cl.

| | |
|---|---|
| ***G01N 33/48*** | (2006.01) |
| ***G01N 33/50*** | (2006.01) |
| ***G01N 33/53*** | (2006.01) |
| ***C12N 15/113*** | (2010.01) |
| ***G01N 33/68*** | (2006.01) |

(52) U.S. Cl.

CPC ........ *C12N 15/1137* (2013.01); *C12N 15/113* (2013.01); *C12N 15/1138* (2013.01); *G01N 33/5032* (2013.01); *G01N 33/6887* (2013.01); *C12N 2310/14* (2013.01); *G01N 2333/726* (2013.01); *G01N 2333/912* (2013.01); *G01N 2333/9121* (2013.01); *G01N 2333/96486* (2013.01); *G01N 2333/96494* (2013.01); *G01N 2500/04* (2013.01); *G01N 2500/10* (2013.01); *G01N 2500/20* (2013.01); *G01N 2800/105* (2013.01)

(58) Field of Classification Search

None

See application file for complete search history.

(56) References Cited

U.S. PATENT DOCUMENTS

| | | | | |
|---|---|---|---|---|
| 7,332,337 | B2 | 2/2008 | Van Es et al. | |
| 2002/0110894 | A1* | 8/2002 | Apte | C12N 9/6489 435/226 |
| 2003/0180258 | A1 | 9/2003 | Van Es et al. | |
| 2003/0198627 | A1 | 10/2003 | Arts et al. | |
| 2007/0071660 | A1 | 3/2007 | McGrew | |

FOREIGN PATENT DOCUMENTS

| | | |
|---|---|---|
| EP | 1426056 | 6/2004 |
| WO | WO9402595 | 2/1994 |
| WO | WO9617823 | 6/1996 |
| WO | WO2003/022300 | 3/2003 |
| WO | WO03020931 | 3/2003 |
| WO | WO04038405 | 5/2004 |
| WO | WO04046332 | 6/2004 |
| WO | WO04092735 | 10/2004 |
| WO | WO04094636 | 11/2004 |
| WO | WO06040357 | 4/2006 |
| WO | WO06047298 | 5/2006 |
| WO | WO2008/014008 | 1/2008 |

OTHER PUBLICATIONS

Alberts et al., 2002, Molecular Biology of the Cell, 4th edition, New York, Garland Science, pp. 1-2.*
Davidson RK et al (2006) Expression profiling of metalloproteinases and their inhibitors in synovium and cartilage Arthritis Res Ther 8(4):R124—XP21020604A.
Porter S et al (2004) Dysregulated Expression of Adamalysin-Thrombospondin Genes in Human Breast Carcinoma Clin Cancer Res 10(7):2429-2440—XP002617699A.
Appleton, CTG et al (2007) Global analyses of gene expression in early experimental osteoarthritis Arthritis Rheum 56(6):1854-1868.
Billinghurst, RC et al (1997) Enhanced cleavage of type II collagen by collagenases in osteoarthritic articular cartilage J Clin Invest 99(7):1534-1545.
Billinghurst, RC et al (2000) Comparison of the degradation of type II collagen and proteoglycan in nasal and articular cartilages induced by interleukin-1 and the selective inhibition of type II collagen cleavage by collagenase Arthritis Rheum. 43(3):664-672.
Cao, Z et al (1996) TRAF6 is a signal transducer for interleukin-1 Nature 383(6599):443-446.
Chen, CJ et al (1992) Multitarget-ribozyme directed to cleave at up to nine highly conserved HIV-1 env RNA regions inhibits HIV-1 replication—potential effectiveness against most presently sequenced HIV-1 isolates Nucleic Acids Res 20(17):4581-4589.

(Continued)

*Primary Examiner* — Elizabeth C Kemmerer
(74) *Attorney, Agent, or Firm* — Klauber & Jackson LLC

(57) ABSTRACT

The invention relates to the field of medicinal research, cartilage physiology and diseases involving the degeneration of cartilage tissue. More specifically, the invention relates to methods and means for identifying compounds that inhibit catabolic processes in chondrocytes and that decrease the degradation of cartilage and/or ECM. The invention also relates to the compounds that are useful in the treatment of osteoarthritis. The invention also relates to targets, the modulation of which results in a decrease in the degradation of ECM and/or cartilage and decrease inflammation. In addition, the invention relates to compositions and methods for the use thereof in treating conditions that are characterized by the degradation of ECM and/or cartilage and inflammation.

11 Claims, 8 Drawing Sheets

(56) References Cited

OTHER PUBLICATIONS

Cooper, MA et al (2009) Distribution of EphA5 receptor protein in the developing and adult mouse nervous system J Comp Neurol 514(4):310-328.
Dahlberg, L et al (2000) Distribution of EphA5 receptor protein in the developing and adult mouse nervous system Arthritis Rheum 43(3):673-682.
Fukushima, K et al (2006) Filopodia formation via a specific Eph family member and PI3K in immortalized cholangiocytes Am J Physiol Gastrointest Liver Physiol 291(5):G812-G819.
Ge, H et al (2008) Activation of G protein-coupled receptor 43 in adipocytes leads to inhibition of lipolysis and suppression of plasma free fatty acids Endocrinology 149(9):4519-4526.
Ivanov, AI et al (2006) Putative dual role of ephrin-Eph receptor interactions in inflammation IUBMB Life 58(7):389-394.
Karin, M (1999) The beginning of the end: IkappaB kinase (IKK) and NF-kappaB activation J Biol Chem. 274(39):27339-27342.
Merlos-Suárez, A et al (2008) Eph-ephrin signalling in adult tissues and cancer Curr Opin Cell Biol 20(2):194-200.
Mitchell, PG et al (1996) Cloning, expression, and type II collagenolytic activity of matrix metalloproteinase-13 from human osteoarthritic cartilage J Clin Invest 97(3):761-768.
Neuhold, LA et al (2001) Postnatal expression in hyaline cartilage of constitutively active human collagenase-3 (MMP-13) induces osteoarthritis in mice J Clin Invest 107(1):35-44.
Pei, Y et al (2006) On the art of identifying effective and specific siRNAs Nat Methods 3(9):670-676.
Romanovsky, AA et al (2006) Microsomal prostaglandin E synthase-1, ephrins, and ephrin kinases as suspected therapeutic targets in arthritis: exposed by "criminal profiling" Ann N Y Acad Sci 1069:183-194.
Schmidt, MR et al (2000) Expression of a human coxsackie/adenovirus receptor transgene permits adenovirus infection of primary lymphocytes J Immunol 165(7):4112-4119.
Shlopov, BV et al (1997) Osteoarthritic lesions. Involvement of three different collagenases Arthritis Rheum 40(11):2065-2074.
Traunecker, A et al (1991) Bispecific single chain molecules (Janusins) target cytotoxic lymphocytes on HIV infected cells EMBO J. 10(12):3655-3659.
Tyner, JW et al (2008) RNAi screening of the tyrosine kinome identifies therapeutic targets in acute myeloid leukemia Blood 111(4):2238-2245.
Ventura, M et al (1993) Activation of HIV-specific ribozyme activity by self-cleavage Nucl. Acids Res. 21(14):3249-3255.
Wang, GL et al (2008) Inhibition of lysophosphatidic acid receptor-2 expression by RNA interference decreases lysophosphatidic acid-induced urokinase plasminogen activator activation, cell invasion, and migration in ovarian cancer SKOV-3 cells Croat Med J 49(2):175-181.
Wu, W et al (2002) Sites of collagenase cleavage and denaturation of type II collagen in aging and osteoarthritic articular cartilage and their relationship to the distribution of matrix metalloproteinase 1 and matrix metalloproteinase 13 Arthritis Rheum 46(8):2087-2094.
Young, DA et al (2005) Histone deacetylase inhibitors modulate metalloproteinase gene expression in chondrocytes and block cartilage resorption Arthritis Res Ther 7(3):R503-R512.
Yuan, ZL et al (2004) Central role of the threonine residue within the p+1 loop of receptor tyrosine kinase in STAT3 constitutive phosphorylation in metastatic cancer cells Mol Cell Biol 24(21):9390-9400.

* cited by examiner

MMP13 assay on NHACs: schematic representation of general protocol

Figure 7

Oligonucleotide primers used for SYBR® Green quantitative real-time PCR.

| Hit-ID | 2nd hit-ID | Target Gene Symbol | Forward primer | SEQ ID NO: | Reverse primer | SEQ ID NO: |
|---|---|---|---|---|---|---|
| H54-127 | H54-305 | ADAM15 | TGGAGATCAGCCCAAACCC | 61 | GCCAGTGGAGGAAGTTTTCG | 62 |
| H54-269 | | CSNK1G2 | AAGACGGTGCTGATGATCGC | 63 | CACATACTCCATGCGCGTG | 64 |
| H54-257 | | EPHA5 | CCACAATGGCATGCACAAG | 65 | TTGAGATGGCATTCCGAGG | 66 |
| H54-024 | H54-025 | GPR43 | GACGCAGAGGCAAAGACACA | 67 | CCACACCCCTGTCCTCATTT | 68 |
| H54-094 | | KCNN4 | CACCTCAAGTGCAAGGACCA | 69 | AAGCCAACCCACTCCAAGC | 70 |
| H54-044 | | MAP2K2 | TTGCATGGAACACATGGACG | 71 | GCCTCTTTCAGCACCTGGTC | 72 |
| H54-140 | | MAP4K1 | GCATCTTCATCCTGAACCGG | 73 | AGAGCATTTCCAGCGTGGC | 74 |
| H54-165 | | MC3R | CACCATCTTTTACGCGCTCC | 75 | GCCTTCCTCACGGTCATGAT | 76 |
| H54-001 | | MET | TTCCCAGATCATCCATTGCA | 77 | CGTTTCCTTTAGCCTTCTCACTGA | 78 |
| H54-016 | | STK32B | GAATATGGGCGGGAACCACT | 79 | TCATTCTCGTCAAACACGGG | 80 |

SEQUENCE LISTING

```
<160> NUMBER OF SEQ ID NOS: 80

<210> SEQ ID NO 1
<211> LENGTH: 6641
<212> TYPE: DNA
<213> ORGANISM: Homo sapiens

<400> SEQUENCE: 1

gccctcgccg cccgcggcgc cccgagcgct ttgtgagcag atgcggagcc gagtggaggg     60

cgcgagccag atgcggggcg acagctgact tgctgagagg aggcggggag gcgcggagcg    120

cgcgtgtggt ccttgcgccg ctgacttctc cactggttcc tgggcaccga aagataaacc    180

tctcataatg aaggcccccg ctgtgcttgc acctggcatc ctcgtgctcc tgtttacctt    240

ggtgcagagg agcaatgggg agtgtaaaga ggcactagca aagtccgaga tgaatgtgaa    300

tatgaagtat cagcttccca acttcaccgc ggaaacaccc atccagaatg tcattctaca    360

tgagcatcac attttccttg gtgccactaa ctacatttat gttttaaatg aggaagacct    420

tcagaaggtt gctgagtaca agactgggcc tgtgctggaa cacccagatt gtttcccatg    480

tcaggactgc agcagcaaag ccaatttatc aggaggtgtt tggaaagata acatcaacat    540
```

-continued ggctctagtt gtcgacacct actatgatga tcaactcatt agctgtggca gcgtcaacag 600
agggacctgc cagcgacatg tctttcccca caatcatact gctgacatac agtcggaggt 660
tcactgcata ttctccccac agatagaaga gcccagccag tgtcctgact gtgtggtgag 720
cgccctggga gccaaagtcc tttcatctgt aaaggaccgg ttcatcaact tctttgtagg 780
caataccata aattcttctt atttcccaga tcatccattg cattcgatat cagtgagaag 840
gctaaaggaa acgaaagatg gttttatgtt tttgacggac cagtcctaca ttgatgtttt 900
acctgagttc agagattctt accccattaa gtatgtccat gcctttgaaa gcaacaattt 960
tatttacttc ttgacggtcc aaagggaaac tctagatgct cagacttttc acacaagaat 1020
aatcaggttc tgttccataa actctggatt gcattcctac atggaaatgc ctctggagtg 1080
tattctcaca gaaaagagaa aaaagagatc cacaaagaag gaagtgttta atatacttca 1140
ggctgcgtat gtcagcaagc ctggggccca gcttgctaga caaataggag ccagcctgaa 1200
tgatgacatt cttttcgggg tgttcgcaca aagcaagcca gattctgccg aaccaatgga 1260
tcgatctgcc atgtgtgcat tccctatcaa atatgtcaac gacttcttca acaagatcgt 1320
caacaaaaac aatgtgagat gtctccagca tttttacgga cccaatcatg agcactgctt 1380
taataggaca cttctgagaa attcatcagg ctgtgaagcg cgccgtgatg aatatcgaac 1440
agagtttacc acagctttgc agcgcgttga cttattcatg ggtcaattca gcgaagtcct 1500
cttaacatct atatccacct tcattaaagg agacctcacc atagctaatc ttgggacatc 1560
agagggtcgc ttcatgcagg ttgtggtttc tcgatcagga ccatcaaccc ctcatgtgaa 1620
ttttctcctg gactcccatc cagtgtctcc agaagtgatt gtggagcata cattaaacca 1680
aaatggctac acactggtta tcactgggaa gaagatcacg aagatcccat tgaatggctt 1740
gggctgcaga catttccagt cctgcagtca atgcctctct gccccaccct ttgttcagtg 1800
tggctggtgc cacgacaaat gtgtgcgatc ggaggaatgc ctgagcggga catggactca 1860
acagatctgt ctgcctgcaa tctacaaggt tttcccaaat agtgcacccc ttgaaggagg 1920
gacaaggctg accatatgtg gctgggactt tggatttcgg aggaataata aatttgattt 1980
aaagaaaact agagttctcc ttggaaatga gagctgcacc ttgactttaa gtgagagcac 2040
gatgaataca ttgaaatgca cagttggtcc tgccatgaat aagcatttca atatgtccat 2100
aattatttca aatggccacg ggacaacaca atacagtaca ttctcctatg tggatcctgt 2160
aataacaagt atttcgccga aatacggtcc tatggctggt ggcactttac ttactttaac 2220
tggaaattac ctaaacagtg ggaattctag acacatttca attggtggaa aaacatgtac 2280
tttaaaaagt gtgtcaaaca gtattcttga atgttatacc ccagcccaaa ccatttcaac 2340
tgagtttgct gttaaattga aaattgactt agccaaccga gagacaagca tcttcagtta 2400
ccgtgaagat cccattgtct atgaaattca tccaaccaaa tcttttatta gtggtgggag 2460
cacaataaca ggtgttggga aaaacctgaa ttcagttagt gtcccgagaa tggtcataaa 2520
tgtgcatgaa gcaggaagga actttacagt ggcatgtcaa catcgctcta attcagagat 2580
aatctgttgt accactcctt ccctgcaaca gctgaatctg caactccccc tgaaaaccaa 2640
agccttttc atgttagatg ggatcctttc caaatacttt gatctcattt atgtacataa 2700
tcctgtgttt aagccttttg aaaagccagt gatgatctca atgggcaatg aaaatgtact 2760
ggaaattaag ggaaatgata ttgaccctga agcagttaaa ggtgaagtgt taaaagttgg 2820
aaataagagc tgtgagaata tacacttaca ttctgaagcc gttttatgca cggtccccaa 2880
tgacctgctg aaattgaaca gcgagctaaa tatagagtgg aagcaagcaa tttcttcaac 2940

-continued

```
cgtccttgga aaagtaatag ttcaaccaga tcagaatttc acaggattga ttgctggtgt   3000
tgtctcaata tcaacagcac tgttattact acttgggttt ttcctgtggc tgaaaaagag   3060
aaagcaaatt aaagatctgg gcagtgaatt agttcgctac gatgcaagag tacacactcc   3120
tcatttggat aggcttgtaa gtgcccgaag tgtaagccca actacagaaa tggtttcaaa   3180
tgaatctgta gactaccgag ctacttttcc agaagatcag tttcctaatt catctcagaa   3240
cggttcatgc cgacaagtgc agtatcctct gacagacatg tcccccatcc taactagtgg   3300
ggactctgat atatccagtc cattactgca aaatactgtc cacattgacc tcagtgctct   3360
aaatccagag ctggtccagg cagtgcagca tgtagtgatt gggcccagta gcctgattgt   3420
gcatttcaat gaagtcatag gaagagggca ttttggttgt gtatatcatg ggactttgtt   3480
ggacaatgat ggcaagaaaa ttcactgtgc tgtgaaatcc ttgaacagaa tcactgacat   3540
aggagaagtt tcccaatttc tgaccgaggg aatcatcatg aaagatttta gtcatcccaa   3600
tgtcctctcg ctcctgggaa tctgcctgcg aagtgaaggg tctccgctgg tggtcctacc   3660
atacatgaaa catggagatc ttcgaaattt cattcgaaat gagactcata atccaactgt   3720
aaaagatctt attggctttg gtcttcaagt agccaaaggc atgaaatatc ttgcaagcaa   3780
aaagtttgtc cacagagact tggctgcaag aaactgtatg ctggatgaaa aattcacagt   3840
caaggttgct gattttggtc ttgccagaga catgtatgat aaagaatact atagtgtaca   3900
caacaaaaca ggtgcaaagc tgccagtgaa gtggatggct ttggaaagtc tgcaaactca   3960
aaagtttacc accaagtcag atgtgtggtc ctttggcgtg ctcctctggg agctgatgac   4020
aagaggagcc ccaccttatc ctgacgtaaa cacctttgat ataactgttt acttgttgca   4080
agggagaaga ctcctacaac ccgaatactg cccagacccc ttatatgaag taatgctaaa   4140
atgctggcac cctaaagccg aaatgcgccc atccttttct gaactggtgt cccggatatc   4200
agcgatcttc tctactttca ttggggagca ctatgtccat gtgaacgcta cttatgtgaa   4260
cgtaaaatgt gtcgctccgt atccttctct gttgtcatca gaagataacg ctgatgatga   4320
ggtggacaca cgaccagcct ccttctggga gacatcatag tgctagtact atgtcaaagc   4380
aacagtccac actttgtcca atggtttttt cactgcctga cctttaaaag gccatcgata   4440
ttctttgctc ttgccaaaat tgcactatta taggacttgt attgttattt aaattactgg   4500
attctaagga atttcttatc tgacagagca tcagaaccag aggcttggtc ccacaggcca   4560
cggaccaatg gcctgcagcc gtgacaacac tcctgtcata ttggagtcca aaacttgaat   4620
tctgggttga atttttaaa aatcaggtac cacttgattt catatgggaa attgaagcag   4680
gaaatattga gggcttcttg atcacagaaa actcagaaga gatagtaatg ctcaggacag   4740
gagcggcagc cccagaacag gccactcatt tagaattcta gtgtttcaaa acacttttgt   4800
gtgttgtatg gtcaataaca tttttcatta ctgatggtgt cattcaccca ttaggtaaac   4860
attccctttt aaatgtttgt ttgtttttttg agacaggatc tcactctgtt gccagggctg   4920
tagtgcagtg gtgtgatcat agctcactgc aacctccacc tcccaggctc aagcctcccg   4980
aatagctggg actacaggcg cacaccacca tccccggcta atttttgtat tttttgtaga   5040
gacggggttt tgccatgttg ccaaggctgg tttcaaactc ctggactcaa gaaatccacc   5100
cacctcagcc tcccaaagtg ctaggattac aggcatgagc cactgcgccc agcccttata   5160
aatttttgta tagacattcc tttggttgga agaatattta taggcaatac agtcaaagtt   5220
tcaaaatagc atcacacaaa acatgtttat aaatgaacag gatgtaatgt acatagatga   5280
```

-continued

```
cattaagaaa atttgtatga aataatttag tcatcatgaa atatttagtt gtcatataaa   5340

aacccactgt ttgagaatga tgctactctg atctaatgaa tgtgaacatg tagatgtttt   5400

gtgtgtattt ttttaaatga aaactcaaaa taagacaagt aatttgttga taaatatttt   5460

taaagataac tcagcatgtt tgtaaagcag gatacatttt actaaaaggt tcattggttc   5520

caatcacagc tcataggtag agcaaagaaa gggtggatgg attgaaaaga ttagcctctg   5580

tctcggtggc aggttcccac ctcgcaagca attggaaaca aaacttttgg ggagttttat   5640

tttgcattag ggtgtgtttt atgttaagca aaacatactt tagaaacaaa tgaaaaaggc   5700

aattgaaaat cccagctatt tcacctagat ggaatagcca ccctgagcag aactttgtga   5760

tgcttcattc tgtggaattt tgtgcttgct actgtatagt gcatgtggtg taggttactc   5820

taactggttt tgtcgacgta aacatttaaa gtgttatatt ttttataaaa atgtttattt   5880

ttaatgatat gagaaaaatt ttgttaggcc acaaaaacac tgcactgtga acattttaga   5940

aaaggtatgt cagactggga ttaatgacag catgattttc aatgactgta aattgcgata   6000

aggaaatgta ctgattgcca atacacccca ccctcattac atcatcagga cttgaagcca   6060

agggttaacc cagcaagcta caaagagggt gtgtcacact gaaactcaat agttgagttt   6120

ggctgttgtt gcaggaaaat gattataact aaaagctctc tgatagtgca gagacttacc   6180

agaagacaca aggaattgta ctgaagagct attacaatcc aaatattgcc gtttcataaa   6240

tgtaataagt aatactaatt cacagagtat tgtaaatggt ggatgacaaa agaaaatctg   6300

ctctgtggaa agaaagaact gtctctacca gggtcaagag catgaacgca tcaatagaaa   6360

gaactcgggg aaacatccca tcaacaggac tacacacttg tatatacatt cttgagaaca   6420

ctgcaatgtg aaaatcacgt ttgctattta taaacttgtc cttagattaa tgtgtctgga   6480

cagattgtgg gagtaagtga ttcttctaag aattagatac ttgtcactgc ctatacctgc   6540

agctgaactg aatggtactt cgtatgttaa tagttgttct gataaatcat gcaattaaag   6600

taaagtgatg caacatcttg taaaaaaaaa aaaaaaaaaa a                       6641
```

<210> SEQ ID NO 2
<211> LENGTH: 3224
<212> TYPE: DNA
<213> ORGANISM: Homo sapiens

<400> SEQUENCE: 2

```
gtcccacatc ccgcatccgg catcccagcg gccgggcatg tagcagcggc agcaacggcg     60

gaatatgggc gggaaccact cccacaagcc ccccgtgttt gacgagaatg aggaagtcaa    120

ctttgaccat tttcagattc tgcgggccat tggtaaaggg agttttggaa aggtatgcat    180

cgtgcagaag cgagacacta agaaaatgta tgcaatgaag tacatgaaca agcagaagtg    240

catcgagagg gatgaggttc ggaatgtttt ccgggagctg cagatcatgc aagggctgga    300

gcaccccttc ctggtcaatc tgtggtactc cttccaggat gaggaggaca tgttcatggt    360

ggtggacctg ctcctgggag gcgacctgcg ctaccatctg cagcagaatg tgcatttcac    420

agaggggact gtgaaactct acatctgtga gctggcactg gccctggagt atcttcagag    480

gtaccacatc atccacagag acatcaagcc agacaatatc ctgctggatg aacacggaca    540

tgttcacatt acagacttca acatagcgac ggtagtgaaa ggagcagaaa gggcttcctc    600

catggctggc accaagccct acatggctcc agaagtattc caggtgtaca tggacagagg    660

ccccggatac tcgtaccctg tcgactggtg gtccctgggc atcacagcct atgagctgct    720

gcggggctgg aggccgtacg aaatccactc ggtcacgccc atcgatgaaa tcctcaacat    780
```

-continued gttcaaggtg gagcgtgtcc actactcctc cacgtggtgc aaggggatgg tggccctgct 840
gaggaagctc ctgaccaagg atcctgagag ccgcgtgtcc agccttcatg acatacagag 900
cgtgccctac ttggccgaca tgaactggga cgcggtgttc aagaaggcac tgatgcccgg 960
ctttgtgccc aataaaggga ggttgaactg cgatccccaca tttgagcttg aagagatgat 1020
tctagaatcc aagccacttc acaaaaagaa gaagcgattg gcaaagaaca gatccaggga 1080
tggcacaaag gacagctgcc cgctgaatgg acacctgcag cactgtttgg agactgtccg 1140
ggaggaattc atcatattca acagagagaa gctcaggagg cagcagggac agggcagcca 1200
gctcttggac accgacagcc gagggggagg ccaggcccaa agcaagctcc aggacgggtg 1260
caacaacaac ctcctcaccc acacctgcac ccgtggctgc agcagctgag cccacacttg 1320
ttgctgctca acaggactgc actcgtctct gccctgccca cccagagccc ctctttgtgc 1380
cctgatggtc cctgtctcac ccctgaaaac atcagatgca gaaaaagccc tggacttgga 1440
gctgggaagc ctgggttctg gtcccatctc catgactgat tcacgtgtga cctcagacaa 1500
gtcacgccct ctctgtgcct ccgttttctg catctgccaa aggggttaaa cacttctgcc 1560
ccacttcaaa ttacaagatt atggggagaa cccaattagg taggaaacat gaaaaacctt 1620
tgatatttat aaaatcattt ttacgtgcaa aatataacct taatatttga agtgaccccc 1680
attccccaaa gcaatcaaac cgtcatgact ttgcaatttg gcacatccta gcttgttaga 1740
gggcacttcc gaaaaacaca gccctgacag caaaataaag gtctgatatg ttggcccctt 1800
ctatggaaac aacgctgcca aatcctggag caaaacctga agtgtcttca tgtgcattct 1860
ctggcaggcc acagtcctga gcttgtaaga tggtgcagca tgcagaccag acttgtcccc 1920
aaggtctcag cgctgcggtc tcactcctcc cctcatttaa gaagactatc cttacctttt 1980
agtttcagca gtcctcacca ccaccatatc cccagtgctg ggatggcaca caggtgtcca 2040
ttcagatgag agttgggtcg ctgagcattg gttactcctg cagagtgtaa tcagcacccc 2100
atccaactgg cccgaaagcc cagacctgca gcagaactct ccaactctct atcagctttc 2160
agggttttct ctcctgggaa gggtgtaaaa tcagcttgtc agattcttct tacagagagt 2220
atccaatcgg tattggtgga gcggctccct atttatacaa taggaagcat gggtgcttag 2280
aaagtttatt tcaggaggaa aatgggttca cacaaaaagc aaactacatt ctgatctgct 2340
cagggagaag cttgcctttg aactggaaga tgttgggatg agcagggaaa gcttagactt 2400
tggagtcagg tttgtgttca gaatccagcc ctgctggcta ctaactaact gggagacctt 2460
aggcaaagca tgcaatcgct ctgaatggca gtttcctcat ttttaaacag ggataataaa 2520
actaatattg caggggagtt acagggttaa ataagatcct gtgtgtaacc ccaagcattg 2580
gatgactcat agaatggcct tttttgtcag cataatcgtc atcattattt agatactttc 2640
ttccttcact cacccagcag gtcagttttc tgtgcaaaca aacctgttta ggattcttcc 2700
aaatgttctt cctggggtct ttgatatttg tttgttacat cctgctgaag ttcgactgtg 2760
tttttatttt ttcatccaac ttccattttt cactttttac atgattactc aatccttggg 2820
gctgtccatg tcatctctta gatttcttaa aagacatttt aatgtatggt taggttttat 2880
atttttattt tttaaaaaag aaatagtcag tgttttcctc ctttcaaccg agactatttc 2940
tggattgtgt gctcctcgtc agttgacttg ttttgcacac ttttctttac ttcatgtccc 3000
catcaacaac cgtcctgctc cccacctccc ccaggaaata aggggcctgc tcctctccct 3060
actgtgaccc tggaggctct taagatgatg atggtttttt ttattgggct gagttcacga 3120

-continued attaggggca ggagctggaa gtcgccctag gaacaccaga tttcctggtt ctgttcaagt 3180
tggcatttct tgtttggaat aaactatttc ttggacattc cttc 3224

<210> SEQ ID NO 3
<211> LENGTH: 1862
<212> TYPE: DNA
<213> ORGANISM: Homo sapiens

<400> SEQUENCE: 3
aaccaattgc accacgaccg gatggaagag cccagctgac acaaccaaga cgagtctcag 60
tgtctaggga agcttggggt tctgctcctt ttacttcagg cgaacctgaa ctttaatgca 120
attttgaagc atgccctgaa tagattcagt cattatcaag tcaaactaaa aacggtgaaa 180
ggttgcgact attaccaaat agaagacaat gagaagtcat accataacaa tgacgacaac 240
ttcagtcagc agctggcctt actcctccca cagaatgcgc tttataacca atcatagcga 300
ccaaccgcca caaaacttct cagcaacacc aaatgttact acctgtccca tggatgaaaa 360
attgctatct actgtgttaa ccacatccta ctctgttatt ttcatcgtgg gactggttgg 420
gaacataatc gccctctatg tatttctggg tattcaccgt aaaagaaatt ccattcaaat 480
ttatctactt aacgtagcca ttgcagacct cctactcatc ttctgcctcc ctttccgaat 540
aatgtatcat attaaccaaa acaagtggac actaggtgtg attctgtgca aggttgtggg 600
aacactgttt tatatgaaca tgtacattag cattattttg cttggattca tcagtttgga 660
tcgctatata aaaattaatc ggtctataca gcaacggaag gcaataacaa ccaaacaaag 720
tatttatgtc tgttgtatag tatggatgct tgctcttggt ggattcctaa ctatgattat 780
tttaacactt aagaaaggag ggcataattc cacaatgtgt ttccattaca gagataagca 840
taacgcaaaa ggagaagcca tttttaactt cattcttgtg gtaatgttct ggctaatttt 900
cttactaata atcctttcat atattaagat tgggaagaat ctattgagga tttctaaaag 960
gaggtcaaaa tttcctaatt ctggtaaata tgccactaca gctcgtaact cctttattgt 1020
acttatcatt tttactatat gttttgttcc ctatcatgcc tttcgattca tctacatttc 1080
ttcacagcta aatgtatcat cttgctactg gaaagaaatt gttcacaaaa ccaatgagat 1140
catgctggtt ctctcatctt tcaatagttg cttagatcca gtcatgtatt tcctgatgtc 1200
cagtaacatt cgcaaaataa tgtgccaact tctttttaga cgatttcaag gtgaaccaag 1260
taggagtgaa agcacttcag aatttaaacc aggatactcc ctgcatgata catctgtggc 1320
agtgaaaata cagtctagtt ctaaaagtac ttgaggtaaa catactaaaa tgaattatat 1380
aatgcagcct cttaattctt tgaagaacta aaaaattagg aaacaaagtt ctagcattta 1440
caaaactcag atctcaaagc tctgcttgta tttgtgatat ttcatttgct taactgtaaa 1500
ccatttcaag gtactaactt ttaaatctgt atgtaaaatc ttttcaaaat acatttttaa 1560
gctaatactc ttaacataga ttatgaagtt aagtgaaatt tatggctcta acagcaaaat 1620
aattaaagtg ccatagtttc tcaagtgact aaagtagtta ttaaaatcaa gcacttgata 1680
ctaatttgaa gtgtgtttaa aagtaaatga tttgggaact gacaatgtgt cagaaaatat 1740
atgttcattt atcattttaa aatcttgtat aatttgccac tgtattcatt tatgcctaaa 1800
tctctataac agatgaaaag ataattaata aaatcctaat taaaaaatga gaaaaaaaaa 1860
aa 1862

<210> SEQ ID NO 4
<211> LENGTH: 1509

<212> TYPE: DNA
<213> ORGANISM: Homo sapiens

<400> SEQUENCE: 4

```
aagagcccag ctgacacaac caagacgagt ctcagtgtct agggaagctt ggggttctgc     60

tccttttact tcaggcgaac ctgaactcag ttaatgcaat tttgaagcat gccctgaata    120

gattcagtca ttatcaagtc aaactaaaaa cggtgaaagg ttgcgactat taccaaatag    180

cattctcatc tccagggtaa cgtgcctatt tccttcaact tgcttctttg acatgatttg    240

agttcttctc tccatttggt ccatggcctt ttctaagtgt gctgctgtgg atcaaacact    300

gcattccagg aaaaatctga agacataaga actacacatg aggaatatgt catttagcac    360

tttcactttt tgatctccac agaagacaat gagaagtcat accataacaa tgacgacaac    420

ttcagtcagc agctggcctt actcctccca cagaatgcgc tttataacca atcatagcga    480

ccaaccgcca caaaacttct cagcaacacc aaatgttact acctgtccca tggatgaaaa    540

attgctatct actgtgttaa ccacatccta ctctgttatt ttcatcgtgg gactggttgg    600

gaacataatc gccctctatg tatttctggg tattcaccgt aaaagaaatt ccattcaaat    660

ttatctactt aacgtagcca ttgcagacct cctactcatc ttctgcctcc ctttccgaat    720

aatgtatcat attaaccaaa acaagtggac actaggtgtg attctgtgca aggttgtggg    780

aacactgttt tatatgaaac aaagtattta tgtctgttgt atagtatgga tgcttgctct    840

tggtggattc ctaactatga ttattttaac acttaagaaa ggagggcata attccacaat    900

gtgtttccat tacagagata agcataacgc aaaaggagaa gccattttta acttcattct    960

tgtggtaatg ttctggctaa ttttcttact aataatcctt tcatatatta agattgggaa   1020

gaatctattg aggatttcta aaaggaggtc aaaatttcct aattctggta aatatgccac   1080

tacagctcgt aactccttta ttgtacttat catttttact atatgttttg ttccctatca   1140

tgcctttcga ttcatctaca tttcttcaca gctaaatgta tcatcttgct actggaaaga   1200

aattgttcac aaaaccaatg agatcatgct ggttctctca tctttcaata gttgcttaga   1260

tccagtcatg tatttcctga tgtccagtaa cattcgcaaa ataatgtgcc aacttctttt   1320

tagacgattt caaggtgaac caagtaggag tgaaagcact tcagaattta aaccaggata   1380

ctccctgcat gatacatctg tggcagtgaa aatacagtct agttctaaaa gtacttgagg   1440

taaacatact aaaatgaatt atataatgca gcctcttaat tctttgaaga actaaaaaat   1500

taggaaaca                                                            1509
```

<210> SEQ ID NO 5
<211> LENGTH: 1282
<212> TYPE: DNA
<213> ORGANISM: Homo sapiens

<400> SEQUENCE: 5

```
ggttctrctc cttttacttc aggcgaacct gaactcagtt aatgcaattt tgaagcatgc     60

cctgaataga ttcagtcatt atcaagtcaa actaaaaacg gtgaaaggtt gcgactatta    120

ccaaatagga aaaacctgaa gacataagaa ctacacatga ggaatatgtc atttagcact    180

ttcacttttt gatctccaca gaagacaatg agaagtcata ccataacaat gacgacaact    240

tcagtcagca gcaacaccaa atgttactac ctgtcccatg gatgaaaaat tgctatctac    300

tgtgttaacc acatcctact ctgttatttt catcgtggga ctggttggga acataatcgc    360

cctctatgta tttctgggta ttcaccgtaa aagaaattcc attcaaattt atctacttaa    420
```

-continued

```
cgtagccatt gcagacctcc tactcatctt ctgcctccct ttccgaataa tgtatcatat    480

taaccaaaac aagtggacac taggtgtgat tctgtgcaag gttgtgggaa cactgtttta    540

tatgaacatg tacattagca ttattttgct tggattcatc agtttggatc gctatataaa    600

aattaatcgg tctatacagc aacggaaggc aataacaacc aaacaaagta tttatgtctg    660

ttgtatagta tggatgcttg ctcttggtgg attcctaact atgattattt taacacttaa    720

gaaaggaggg cataattcca caatgtgttt ccattacaga gataagcata acgcaaaagg    780

agaagccatt tttaacttca ttcttgtggt aatgttctgg ctaattttct tactaataat    840

cctttcatat attaagattg ggaagaatct attgaggatt tctaaaagga ggtcaaaatt    900

tcctaattct ggtaaatatg ccactacagc tcgtaactcc tttattgtac ttatcatttt    960

tactatatgt tttgttccct atcatgcctt tcgattcatc tacatttctt cacagctaaa   1020

tgtatcatct tgctactgga aagaaattgt tcacaaaacc aatgagatca tgctggttct   1080

ctcatctttc aatagttgct tagatccagt catgtatttc ctgatgtcca gtaacattcg   1140

caaaataatg tgccaacttc tttttagacg atttcaaggt gaaccaagta ggagtgaaag   1200

cacttcagaa tttaaaccag gatactccct gcatgataca tctgtggcag tgaaaataca   1260

gtctagttct aaaagtactt ga                                            1282
```

<210> SEQ ID NO 6
<211> LENGTH: 993
<212> TYPE: DNA
<213> ORGANISM: Homo sapiens

<400> SEQUENCE: 6

```
atgctgccgg actggaagag ctccttgatc ctcatggctt acatcatcat cttcctcact     60

ggcctccctg ccaacctcct ggccctgcgg gcctttgtgg ggcggatccg ccagccccag    120

cctgcacctg tgcacatcct cctgctgagc ctgacgctgg ccgacctcct cctgctgctg    180

ctgctgccct tcaagatcat cgaggctgcg tcgaacttcc gctggtacct gcccaaggtc    240

gtctgcgccc tcacgagttt tggcttctac agcagcatct actgcagcac gtggctcctg    300

gcgggcatca gcatcgagcg ctacctggga gtggctttcc ccgtgcagta caagctctcc    360

cgccggcctc tgtatggagt gattgcagct ctggtggcct gggttatgtc ctttggtcac    420

tgcaccatcg tgatcatcgt tcaatacttg aacacgactg agcaggtcag aagtggcaat    480

gaaattacct gctacgagaa cttcaccgat aaccagttgg acgtggtgct gcccgtgcgg    540

ctggagctgt gcctggtgct cttcttcatc cccatggcag tcaccatctt ctgctactgg    600

cgttttgtgt ggatcatgct ctcccagccc cttgtggggg cccagaggcg gcgccgagcc    660

gtggggctgg ctgtggtgac gctgctcaat ttcctggtgt gcttcggacc ttacaacgtg    720

tcccacctgg tggggtatca ccagagaaaa agcccctggt ggcggtcaat agccgtggtg    780

ttcagttcac tcaacgccag tctggacccc ctgctcttct atttctcttc ttcagtggtg    840

cgcagggcat ttgggagagg gctgcaggtg ctgcggaatc agggctcctc cctgttggga    900

cgcagaggca aagacacagc agaggggaca aatgaggaca ggggtgtggg tcaaggagaa    960

gggatgccaa gttcggactt cactacagag tag                                 993
```

<210> SEQ ID NO 7
<211> LENGTH: 1759
<212> TYPE: DNA
<213> ORGANISM: Homo sapiens

<400> SEQUENCE: 7

```
cccctgcctc tcggactcgg gctgcggcgt cagccttctt cgggcctcgg cagcggtagc     60
ggctcgctcg cctcagcccc agcgcccctc ggctaccctc ggcccaggcc cgcagcgccg    120
cccgccctcg gccgccccga cgccggcctg ggccgcggcc gcagccccgg gctcgcgtag    180
gcgccgaccg ctcccggccc gcccccctatg ggccccggct agaggcgccg ccgccgccgg   240
cccgcggagc cccgatgctg gcccggagga agccggtgct gccggcgctc accatcaacc    300
ctaccatcgc cgagggccca tcccctacca gcgagggcgc ctccgaggca aacctggtgg    360
acctgcagaa gaagctggag gagctggaac ttgacgagca gcagaagaag cggctggaag    420
cctttctcac ccagaaagcc aaggtcggcg aactcaaaga cgatgacttc gaaaggatct    480
cagagctggg cgcgggcaac ggcggggtgg tcaccaaagt ccagcacaga ccctcgggcc    540
tcatcatggc caggaagctg atccaccttg agatcaagcc ggccatccgg aaccagatca    600
tccgcgagct gcaggtcctg cacgaatgca actcgccgta catcgtgggc ttctacgggg    660
ccttctacag tgacggggag atcagcattt gcatggaaca catggacggc ggctccctgg    720
accaggtgct gaaagaggcc aagaggattc ccgaggagat cctggggaaa gtcagcatcg    780
cggttctccg gggcttggcg tacctccgag agaagcacca gatcatgcac cgagatgtga    840
agccctccaa catcctcgtg aactctagag gggagatcaa gctgtgtgac ttcggggtga    900
gcggccagct catcgactcc atggccaact ccttcgtggg cacgcgctcc tacatggctc    960
cggagcggtt gcagggcaca cattactcgg tgcagtcgga catctggagc atgggcctgt   1020
ccctggtgga gctggccgtc ggaaggtacc ccatcccccc gcccgacgcc aaagagctgg   1080
aggccatctt tggccggccc gtggtcgacg gggaagaagg agagcctcac agcatctcgc   1140
ctcggccgag gccccccggg cgccccgtca gcggtcacgg gatggatagc cggcctgcca   1200
tggccatctt tgaactcctg gactatattg tgaacgagcc acctcctaag ctgcccaacg   1260
gtgtgttcac ccccgacttc caggagtttg tcaataaatg cctcatcaag aacccagcgg   1320
agcgggcgga cctgaagatg ctcacaaacc acaccttcat caagcggtcc gaggtggaag   1380
aagtggattt tgccggctgg ttgtgtaaaa ccctgcggct gaaccagccc ggcacaccca   1440
cgcgcaccgc cgtgtgacag tggccgggct ccctgcgtcc cgctggtgac ctgcccaccg   1500
tccctgtcca tgccccgccc ttccagctga ggacaggctg gcgcctccac ccaccctcct   1560
gcctcacccc tgcggagagc accgtggcgg ggcgacagcg catgcaggaa cgggggtctc   1620
ctctcctgcc cgtcctggcc ggggtgcctc tggggacggg cgacgctgct gtgtgtggtc   1680
tcagaggctc tgcttcctta ggttacaaaa caaaacaggg agagaaaaag caaaaaaaaa   1740
aaaaaaaaaa aaaaaaaaa                                                1759
```

<210> SEQ ID NO 8
<211> LENGTH: 2848
<212> TYPE: DNA
<213> ORGANISM: Homo sapiens

<400> SEQUENCE: 8

```
aatcatccag ttttctaaat tatggaaatt ttgtggaaga cgttgacctg gattttgagc     60
ctcatcatgg cttcatcgga atttcatagt gaccacaggc tttcatacag ttctcaagag    120
gaattcctga cttatcttga acactaccag ctaactattc caataagggt tgatcaaaat    180
ggagcatttc tcagctttac tgtgaaaaat gataaacact caaggagaag acggagtatg    240
gaccctattg atccacagca ggcagtatct aagttatttt ttaaactttc agcctatggc    300
```

-continued

```
aagcactttc atctaaactt gactctcaac acagattttg tgtccaaaca ttttacagta    360
gaatattggg ggaaagatgg accccagtgg aaacatgatt ttttagacaa ctgtcattac    420
acaggatatt tgcaagatca acgtagtaca actaaagtgg ctttaagcaa ctgtgttggg    480
ttgcatggtg ttattgctac agaagatgaa gagtatttta tcgaaccttt aaagaatacc    540
acagaggatt ccaagcattt tagttatgaa aatggccacc ctcatgttat ttacaaaaag    600
tctgcccttc aacaacgaca tctgtatgat cactctcatt gtggggtttc ggatttcaca    660
agaagtggca aaccttggtg gctgaatgac acatccactg tttcttattc actaccaatt    720
aacaacacac atatccacca cagacagaag agatcagtga gcattgaacg gtttgtggag    780
acattggtag tggcagacaa aatgatggtg ggctaccatg gccgcaaaga cattgaacat    840
tacattttga gtgtgatgaa tattgttgcc aaactttacc gtgattccag cctaggaaac    900
gttgtgaata ttatagtggc ccgcttaatt gttctcacag aagatcagcc aaacttggag    960
ataaaccacc atgcagacaa gtccctcgat agcttctgta aatggcagaa atccattctc   1020
tcccaccaaa gtgatggaaa caccattcca gaaaatggga ttgcccacca cgataatgca   1080
gttcttatta ctagatatga tatctgcact tataaaaata agccctgtgg aacactgggc   1140
ttggcctctg tggctggaat gtgtgagcct gaaaggagct gcagcattaa tgaagacatt   1200
ggcctgggtt cagcttttac cattgcacat gagattgttc acaattttgg tatgaaccat   1260
gatggaattg gaaattcttg tggacgaaag gtcatgaagc agcaaaatta tggcagctca   1320
cattactgcg aataccaatc ctttttcctg gtctgcttgc agtcgagact acatcaccag   1380
ctttttagag aagtgtgtag agagctctgg tgtctcagca aaagcaaccg ctgtgtcacc   1440
aacagtattc cagcagctga ggggacactg tgtcaaactg ggaatattga aaaagggtgg   1500
tgttatcagg gagattgtgt tccttttggc acttggcccc agagcataga tgggggctgg   1560
ggtccctggt cactatgggg agagtgcagc aggacctgcg gggggaggcgt ctcctcatcc  1620
ctaagacact gtgacagtcc agcaccttca ggaggtggaa aatattgcct tggggaaagg   1680
aaacggtatc gctcctgtaa cacagatcca tgccctttgg gttcccgaga ttttcgagag   1740
aaacagtgtg cagactttga caatatgcct ttccgaggaa agtattataa ctggaaaccc   1800
tatactggag gtggggtaaa accttgtgca ttaaactgct tggctgaagg ttataatttc   1860
tacactgaac gtgctcctgc ggtgatcgat gggacccagt gcaatgcgga ttcactggat   1920
atctgcatca atggagaatg caagcacgta ggctgtgata atattttggg atctgatgct   1980
agggaagata gatgtcgagt ctgtggaggg gacggaagca catgtgatgc cattgaaggg   2040
ttcttcaatg attcactgcc caggggaggc tacatggaag tggtgcagat accaagaggc   2100
tctgttcaca ttgaagttag agaagttgcc atgtcaaaga actatattgc tttaaaatct   2160
gaaggagatg attactatat taatggtgcc tggactattg actggcctag gaaatttgat   2220
gttgctggga cagcttttca ttacaagaga ccaactgatg aaccagaatc cttggaagct   2280
ctaggtccta cctcagaaaa tctcatcgtc atggttctgc ttcaagaaca gaatttggga   2340
attaggtata agttcaatgt tcccatcact cgaactggca gtggagataa tgaagttggc   2400
tttacatgga atcatcagcc ttggtcagaa tgctcagcta cttgtgctgg aggtaagatg   2460
cccactaggc agcccaccca gagggcaaga tggagaacaa aacacattct gagctatgct   2520
ttgtgtttgt taaaaaagct aattggaaac atttcttgca ggtttgcttc aagctgtaat   2580
ttagcaaaag aaactttgct ttaattatat tatattccat ttgttttcaa cctcatgtaa   2640
tttgtgcaga tttgttggta aaatacatct tggcacaatg agtgtctctg ctggtgcttc   2700
```

```
tcccaagact atcttgaagg tggctgttt gcctttcgtg aacacattct tggtaaagaa   2760

catcaaaagt tttaaaaaag aaaatgagca agaatcagac atcacagatg caacttcttg   2820

taatgggaga tgagaatgta cggctgtg                                      2848


<210> SEQ ID NO 9
<211> LENGTH: 2240
<212> TYPE: DNA
<213> ORGANISM: Homo sapiens

<400> SEQUENCE: 9

gtccttcggt gtctgggtgt ggtgagtaga ggtgtgtgtc acaaagtaca gaccattgtg     60

tgtgacaaag cccatcgtgt gtctgtgtgt gtctttatcc acgtggatgg acgtctcttt    120

cttgctctgc cccaagacac accctagccc ctccttattc tcaaaagggg gagctgggga    180

gcctcccccct accctggggc ctcccctgcc cctccccgcc ctgcctggcc gtcaccactc   240

cccagagggc acagggctct gctgtgcctc agagcaaaag tcccagagcc agcagagcag    300

gctgacgacc tgcaagccac agtggctgcc ctgtgcgtgc tgcgaggtgg gggaccctgg    360

gcaggaagct ggctgagccc caagaccccg ggggccatgg gcggggatct ggtgcttggc    420

ctgggggcct tgagacgccg aaagcgcttg ctggagcagg agaagtctct ggccggctgg    480

gcactggtgc tggcaggaac tggcattgga ctcatggtgc tgcatgcaga gatgctgtgg    540

ttcggggggt gctcgtgggc gctctacctg ttcctggtta aatgcacgat cagcatttcc    600

accttcttac tcctctgcct catcgtggcc tttcatgcca aagaggtcca gctgttcatg    660

accgacaacg ggctgcggga ctggcgcgtg gcgctgaccg ggcggcaggc ggcgcagatc    720

gtgctggagc tggtggtgtg tgggctgcac ccggcgcccg tgcggggccc gccgtgcgtg    780

caggatttag ggcgccgct gacctccccg cagccctggc cgggattcct gggccaaggg     840

gaagcgctgc tgtccctggc catgctgctg cgtctctacc tggtgccccg cgccgtgctc    900

ctgcgcagcg gcgtcctgct caacgcttcc taccgcagca tcggcgctct caatcaagtc    960

cgcttccgcc actggttcgt ggccaagctt tacatgaaca cgcaccctgg ccgcctgctg   1020

ctcggcctca cgcttggcct ctggctgacc accgcctggg tgctgtccgt ggccgagagg   1080

caggctgtta atgccactgg gcacctttca gacacacttt ggctgatccc catcacattc   1140

ctgaccatcg gctatggtga cgtggtgccg ggcaccatgt ggggcaagat cgtctgcctg   1200

tgcactggag tcatgggtgt ctgctgcaca gccctgctgg tggccgtggt ggcccggaag   1260

ctggagttta acaaggcaga gaagcacgtg cacaacttca tgatggatat ccagtatacc   1320

aaagagatga aggagtccgc tgcccgagtg ctacaagaag cctggatgtt ctacaaacat   1380

actcgcagga aggagtctca tgctgcccgc aggcatcagc gcaagctgct ggccgccatc   1440

aacgcgttcc gccaggtgcg gctgaaacac cggaagctcc gggaacaagt gaactccatg   1500

gtggacatct ccaagatgca catgatcctg tatgacctgc agcagaatct gagcagctca   1560

caccgggccc tggagaaaca gattgacacg ctggcgggga agctggatgc cctgactgag   1620

ctgcttagca ctgccctggg gccgaggcag cttccagaac ccagccagca gtccaagtag   1680

ctggacccac gaggaggaac caggctactt tccccagtac tgaggtggtg gacatcgtct   1740

ctgccactcc tgacccagcc ctgaacaaag cacctcaagt gcaaggacca aagggggccc   1800

tggcttggag tgggttggct tgctgatggc tgctggaggg gacgctggct aaagtgggta   1860

ggccttggcc cacctgaggc cccaggtggg aacatggtca cccccactct gcataccctc   1920
```

-continued

```
atcaaaaaca ctctcactat gctgctatgg acgacctcca gctctcagtt acaagtgcag   1980

gcgactggag gcaggactcc tgggtccctg ggaaagaggg tactaggggc ccggatccag   2040

gattctggga ggcttcagtt accgctggcc gagctgaaga actgggtatg aggctggggc   2100

ggggctggag gtggcgcccc ctggtgggac aacaaagagg acaccatttt tccagagctg   2160

cagagagcac ctggtgggga ggaagaagtg taactcacca gcctctgctc ttatctttgt   2220

aataaatgtt aaagccagaa                                               2240
```

<210> SEQ ID NO 10
<211> LENGTH: 2823
<212> TYPE: DNA
<213> ORGANISM: Homo sapiens

<400> SEQUENCE: 10

```
gcgcggcgct gctgggttct ccgaggcgac ctggccgccg gccgctcctc cgcgcgctgt     60

tccgcacttg ctgccctcgc ccggcccgga gcgccgctgc catgcggctg gcgctgctct    120

gggccctggg gctcctgggc gcgggcagcc ctctgccttc ctggccgctc ccaaatatag    180

gtggcactga ggagcagcag gcagagtcag agaaggcccc gagggagccc ttggagcccc    240

aggtccttca ggacgatctc ccaattagcc tcaaaaaggt gcttcagacc agtctgcctg    300

agcccctgag gatcaagttg gagctggacg gtgacagtca tatcctggag ctgctacaga    360

atagggagtt ggtcccaggc cgcccaaccc tggtgtggta ccagcccgat ggcactcggg    420

tggtcagtga gggacacact ttggagaact gctgctacca gggaagagtg cggggatatg    480

caggctcctg ggtgtccatc tgcacctgct ctgggctcag aggcttggtg gtcctgaccc    540

cagagagaag ctataccctg gagcaggggc ctggggacct tcagggtcct cccattattt    600

cgcgaatcca agatctccac ctgccaggcc acacctgtgc cctgagctgg cgggaatctg    660

tacacactca gaagccacca gagcaccccc tgggacagcg ccacattcgc cggaggcggg    720

atgtggtaac agagaccaag actgtggagt tggtgattgt ggctgatcac tcggaggccc    780

agaaataccg ggacttccag cacctgctaa accgcacact ggaagtggcc ctcttgctgg    840

acacattctt ccggcccctg aatgtacgag tggcactagt gggcctggag gcctggaccc    900

agcgtgacct ggtggagatc agcccaaacc cagctgtcac cctcgaaaac ttcctccact    960

ggcgcagggc acatttgctg cctcgattgc cccatgacag tgcccagctg gtgactggta   1020

cttcattctc tgggcctacg gtgggcatgg ccattcagaa ctccatctgt tctcctgact   1080

tctcaggagg tgtgaacatg gaccactcca ccagcatcct gggagtcgcc tcctccatag   1140

cccatgagtt gggccacagc ctgggcctgg accatgattt gcctgggaat agctgcccct   1200

gtccaggtcc agccccagcc aagacctgca tcatggaggc ctccacagac ttcctaccag   1260

gcctgaactt cagcaactgc agccgacggg ccctggagaa agccctcctg gatggaatgg   1320

gcagctgcct cttcgaacgg ctgcctagcc taccccctat ggctgctttc tgcggaaata   1380

tgtttgtgga gccgggcgag cagtgtgact gtggcttcct ggatgactgc gtcgatccct   1440

gctgtgattc tttgacctgc cagctgaggc caggtgcaca gtgtgcatct gacggaccct   1500

gttgtcaaaa ttgccagctg cgcccgtctg gctggcagtg tcgtcctacc agaggggatt   1560

gtgacttgcc tgaattctgc ccaggagaca gctcccagtg tccccctgat gtcagcctag   1620

gggatggcga gccctgcgct ggcgggcaag ctgtgtgcat gcacgggcgt tgtgcctcct   1680

atgcccagca gtgccagtca ctttggggac ctggagccca gcccgctgcg ccactttgcc   1740

tccagacagc taatactcgg ggaaatgctt ttgggagctg tgggcgcaac cccagtggca   1800
```

-continued

```
gttatgtgtc ctgcacccct agagatgcca tttgtgggca gctccagtgc cagacaggta   1860

ggacccagcc tctgctgggc tccatccggg atctactctg ggagacaata gatgtgaatg   1920

ggactgagct gaactgcagc tgggtgcacc tggacctggg cagtgatgtg gcccagcccc   1980

tcctgactct gcctggcaca gcctgtggcc ctggcctggt gtgtatagac catcgatgcc   2040

agcgtgtgga tctcctgggg gcacaggaat gtcgaagcaa atgccatgga catggggtct   2100

gtgacagcaa caggcactgc tactgtgagg agggctgggc acccccctgac tgcaccactc  2160

agctcaaagc aaccagctcc ctgaccacag ggctgctcct cagcctcctg gtcttattgg   2220

tcctggtgat gcttggtgcc agctactggt accgtgcccg cctgcaccag cgactctgcc   2280

agctcaaggg acccacctgc cagtacaggg cagcccaatc tggtccctct gaacggccag   2340

gacctccgca gagggccctg ctggcacgag gcactaagtc tcaggggcca gccaagcccc   2400

cacccccaag gaagccactg cctgccgacc cccagggccg gtgcccatcg ggtgacctgc   2460

ccggcccagg ggctggaatc ccgcccctag tggtaccctc cagaccagcg ccaccgcctc   2520

cgacagtgtc ctcgctctac ctctgacctc tccggaggtt ccgctgcctc caagccggac   2580

ttagggcttc aagaggcggg cgtgccctct ggagtcccct accatgactg aaggcgccag   2640

agactggcgg tgtcttaaga ctccgggcac cgccacgcgc tgtcaagcaa cactctgcgg   2700

acctgccggc gtagttgcag cgggggcttg gggaggggct gggggttgga cgggattgag   2760

gaaggtccgc acagcctgtc tctgctcagt tgcaataaac gtgacatctt gggagcgttc   2820

aaa                                                                 2823
```

```
<210> SEQ ID NO 11
<211> LENGTH: 2753
<212> TYPE: DNA
<213> ORGANISM: Homo sapiens

<400> SEQUENCE: 11

gcgcggcgct gctgggttct ccgaggcgac ctggccgccg gccgctcctc cgcgcgctgt     60

tccgcacttg ctgccctcgc ccggcccgga gcgccgctgc catgcggctg gcgctgctct    120

gggccctggg gctcctgggc gcgggcagcc ctctgccttc ctggccgctc ccaaatatag    180

gtggcactga ggagcagcag gcagagtcag agaaggcccc gagggagccc ttggagcccc    240

aggtccttca ggacgatctc ccaattagcc tcaaaaaggt gcttcagacc agtctgcctg    300

agcccctgag gatcaagttg gagctggacg gtgacagtca tatcctggag ctgctacaga    360

atagggagtt ggtcccaggc cgcccaaccc tggtgtggta ccagcccgat ggcactcggg    420

tggtcagtga gggacacact ttggagaact gctgctacca gggaagagtg cggggatatg    480

caggctcctg ggtgtccatc tgcacctgct ctgggctcag aggcttggtg gtcctgaccc    540

cagagagaag ctataccctg gagcaggggc ctggggacct tcagggtcct cccattattt    600

cgcgaatcca agatctccac ctgccaggcc acacctgtgc cctgagctgg cgggaatctg    660

tacacactca gaagccacca gagcaccccc tgggacagcg ccacattcgc cggaggcggg    720

atgtggtaac agagaccaag actgtggagt tggtgattgt ggctgatcac tcggaggccc    780

agaaataccg ggacttccag cacctgctaa accgcacact ggaagtggcc ctcttgctgg    840

acacattctt ccggcccctg aatgtacgag tggcactagt gggcctggag gcctggaccc    900

agcgtgacct ggtggagatc agcccaaacc cagctgtcac cctcgaaaac ttcctccact    960

ggcgcagggc acatttgctg cctcgattgc cccatgacag tgcccagctg gtgactggta   1020
```

-continued

```
cttcattctc tgggcctacg gtgggcatgg ccattcagaa ctccatctgt tctcctgact   1080

tctcaggagg tgtgaacatg gaccactcca ccagcatcct gggagtcgcc tcctccatag   1140

cccatgagtt gggccacagc ctgggcctgg accatgattt gcctgggaat agctgcccct   1200

gtccaggtcc agccccagcc aagacctgca tcatggaggc ctccacagac ttcctaccag   1260

gcctgaactt cagcaactgc agccgacggg ccctggagaa agccctcctg gatggaatgg   1320

gcagctgcct cttcgaacgg ctgcctagcc tacccccctat ggctgctttc tgcggaaata   1380

tgtttgtgga gccgggcgag cagtgtgact gtggcttcct ggatgactgc gtcgatccct   1440

gctgtgattc tttgacctgc cagctgaggc caggtgcaca gtgtgcatct gacggaccct   1500

gttgtcaaaa ttgccagctg cgcccgtctg gctggcagtg tcgtcctacc agaggggatt   1560

gtgacttgcc tgaattctgc ccaggagaca gctcccagtg tccccctgat gtcagcctag   1620

gggatggcga gccctgcgct ggcgggcaag ctgtgtgcat gcacgggcgt tgtgcctcct   1680

atgcccagca gtgccagtca ctttggggac ctggagccca gcccgctgcg ccactttgcc   1740

tccagacagc taatactcgg ggaaatgctt ttgggagctg tgggcgcaac cccagtggca   1800

gttatgtgtc ctgcacccct agagatgcca tttgtgggca gctccagtgc cagacaggta   1860

ggacccagcc tctgctgggc tccatccggg atctactctg ggagacaata gatgtgaatg   1920

ggactgagct gaactgcagc tgggtgcacc tggacctggg cagtgatgtg gcccagcccc   1980

tcctgactct gcctggcaca gcctgtggcc ctggcctggt gtgtatagac catcgatgcc   2040

agcgtgtgga tctcctgggg gcacaggaat gtcgaagcaa atgccatgga catggggtct   2100

gtgacagcaa caggcactgc tactgtgagg agggctgggc accccctgac tgcaccactc   2160

agctcaaagc aaccagctcc ctgaccacag ggctgctcct cagcctcctg gtcttattgg   2220

tcctggtgat gcttggtgcc agctactggt accgtgcccg cctgcaccag cgactctgcc   2280

agctcaaggg acccacctgc cagtacagtc tcaggggcca gccaagcccc cacccccaag   2340

gaagccactg cctgccgacc cccagggccg gtgcccatcg ggtgacctgc ccggcccagg   2400

ggctggaatc ccgcccctag tggtaccctc cagaccagcg ccaccgcctc cgacagtgtc   2460

ctcgctctac ctctgacctc tccggaggtt ccgctgcctc caagccggac ttagggcttc   2520

aagaggcggg cgtgccctct ggagtcccct accatgactg aaggcgccag agactggcgg   2580

tgtcttaaga ctccgggcac cgccacgcgc tgtcaagcaa cactctgcgg acctgccggc   2640

gtagttgcag cgggggcttg gggaggggct gggggttgga cgggattgag gaaggtccgc   2700

acagcctgtc tctgctcagt tgcaataaac gtgacatctt gggagcgttc aaa          2753
```

<210> SEQ ID NO 12
<211> LENGTH: 2898
<212> TYPE: DNA
<213> ORGANISM: Homo sapiens

<400> SEQUENCE: 12

```
gcgcggcgct gctgggttct ccgaggcgac ctggccgccg gccgctcctc cgcgcgctgt     60

tccgcacttg ctgccctcgc ccggcccgga gcgccgctgc catgcggctg gcgctgctct    120

gggccctggg gctcctgggc gcgggcagcc ctctgccttc ctggccgctc ccaaatatag    180

gtggcactga ggagcagcag gcagagtcag agaaggcccc gagggagccc ttggagcccc    240

aggtccttca ggacgatctc ccaattagcc tcaaaaaggt gcttcagacc agtctgcctg    300

agcccctgag gatcaagttg gagctggacg gtgacagtca tatcctggag ctgctacaga    360

atagggagtt ggtcccaggc cgcccaaccc tggtgtggta ccagcccgat ggcactcggg    420
```

-continued

```
tggtcagtga gggacacact ttggagaact gctgctacca gggaagagtg cggggatatg    480
caggctcctg ggtgtccatc tgcacctgct ctgggctcag aggcttggtg gtcctgaccc    540
cagagagaag ctataccctg gagcaggggc ctggggacct tcagggtcct cccattattt    600
cgcgaatcca agatctccac ctgccaggcc acacctgtgc cctgagctgg cgggaatctg    660
tacacactca gaagccacca gagcaccccc tgggacagcg ccacattcgc cggaggcggg    720
atgtggtaac agagaccaag actgtggagt tggtgattgt ggctgatcac tcggaggccc    780
agaaataccg ggacttccag cacctgctaa accgcacact ggaagtggcc ctcttgctgg    840
acacattctt ccggcccctg aatgtacgag tggcactagt gggcctggag gcctggaccc    900
agcgtgacct ggtggagatc agcccaaacc cagctgtcac cctcgaaaac ttcctccact    960
ggcgcagggc acatttgctg cctcgattgc cccatgacag tgcccagctg gtgactggta   1020
cttcattctc tgggcctacg gtgggcatgg ccattcagaa ctccatctgt tctcctgact   1080
tctcaggagg tgtgaacatg gaccactcca ccagcatcct gggagtcgcc tcctccatag   1140
cccatgagtt gggccacagc ctgggcctgg accatgattt gcctgggaat agctgcccct   1200
gtccaggtcc agccccagcc aagacctgca tcatggaggc ctccacagac ttcctaccag   1260
gcctgaactt cagcaactgc agccgacggg ccctggagaa agccctcctg gatggaatgg   1320
gcagctgcct cttcgaacgg ctgcctagcc taccccctat ggctgctttc tgcggaaata   1380
tgtttgtgga gccgggcgag cagtgtgact gtggcttcct ggatgactgc gtcgatccct   1440
gctgtgattc tttgacctgc cagctgaggc caggtgcaca gtgtgcatct gacggaccct   1500
gttgtcaaaa ttgccagctg cgcccgtctg gctggcagtg tcgtcctacc agaggggatt   1560
gtgacttgcc tgaattctgc ccaggagaca gctcccagtg tccccctgat gtcagcctag   1620
gggatggcga gccctgcgct ggcgggcaag ctgtgtgcat gcacgggcgt tgtgcctcct   1680
atgcccagca gtgccagtca ctttggggac ctggagccca gcccgctgcg ccactttgcc   1740
tccagacagc taatactcgg ggaaatgctt ttgggagctg tgggcgcaac cccagtggca   1800
gttatgtgtc ctgcacccct agagatgcca tttgtgggca gctccagtgc cagacaggta   1860
ggacccagcc tctgctgggc tccatccggg atctactctg ggagacaata gatgtgaatg   1920
ggactgagct gaactgcagc tgggtgcacc tggacctggg cagtgatgtg gcccagcccc   1980
tcctgactct gcctggcaca gcctgtggcc ctggcctggt gtgtatagac catcgatgcc   2040
agcgtgtgga tctcctgggg gcacaggaat gtcgaagcaa atgccatgga catggggtct   2100
gtgacagcaa caggcactgc tactgtgagg agggctgggc accccctgac tgcaccactc   2160
agctcaaagc aaccagctcc ctgaccacag ggctgctcct cagcctcctg gtcttattgg   2220
tcctggtgat gcttggtgcc agctactggt accgtgcccg cctgcaccag cgactctgcc   2280
agctcaaggg acccacctgc cagtacaggg cagcccaatc tggtccctct gaacggccag   2340
gacctccgca gagggccctg ctggcacgag gcactaagca ggctagtgct ctcagcttcc   2400
cggccccccc ttccaggccg ctgccgcctg accctgtgtc caagagactc cagtctcagg   2460
ggccagccaa gcccccaccc ccaaggaagc cactgcctgc cgacccccag ggccggtgcc   2520
catcgggtga cctgcccggc ccaggggctg gaatcccgcc cctagtggta ccctccagac   2580
cagcgccacc gcctccgaca gtgtcctcgc tctacctctg acctctccgg aggttccgct   2640
gcctccaagc cggacttagg gcttcaagag gcgggcgtgc cctctggagt cccctaccat   2700
gactgaaggc gccagagact ggcggtgtct taagactccg ggcaccgcca cgcgctgtca   2760
```

-continued agcaacactc tgcggacctg ccggcgtagt tgcagcgggg gcttggggag gggctggggg 2820
ttggacggga ttgaggaagg tccgcacagc ctgtctctgc tcagttgcaa taaacgtgac 2880
atcttgggag cgttcaaa 2898

<210> SEQ ID NO 13
<211> LENGTH: 2895
<212> TYPE: DNA
<213> ORGANISM: Homo sapiens

<400> SEQUENCE: 13
gcgcggcgct gctgggttct ccgaggcgac ctggccgccg gccgctcctc cgcgcgctgt 60
tccgcacttg ctgccctcgc ccggcccgga gcgccgctgc catgcggctg gcgctgctct 120
gggccctggg gctcctgggc gcgggcagcc ctctgccttc ctggccgctc ccaaatatag 180
gtggcactga ggagcagcag gcagagtcag agaaggcccc gagggagccc ttggagcccc 240
aggtccttca ggacgatctc ccaattagcc tcaaaaaggt gcttcagacc agtctgcctg 300
agcccctgag gatcaagttg gagctggacg gtgacagtca tatcctggag ctgctacaga 360
atagggagtt ggtcccaggc cgcccaaccc tggtgtggta ccagcccgat ggcactcggg 420
tggtcagtga gggacacact ttggagaact gctgctacca gggaagagtg cggggatatg 480
caggctcctg ggtgtccatc tgcacctgct ctgggctcag aggcttggtg gtcctgaccc 540
cagagagaag ctataccctg gagcaggggc ctggggacct tcagggtcct cccattattt 600
cgcgaatcca agatctccac ctgccaggcc acacctgtgc cctgagctgg cgggaatctg 660
tacacactca gaagccacca gagcaccccc tgggacagcg ccacattcgc cggaggcggg 720
atgtggtaac agagaccaag actgtggagt tggtgattgt ggctgatcac tcggaggccc 780
agaaataccg ggacttccag cacctgctaa accgcacact ggaagtggcc ctcttgctgg 840
acacattctt ccggcccctg aatgtacgag tggcactagt gggcctggag gcctggaccc 900
agcgtgacct ggtggagatc agcccaaacc cagctgtcac cctcgaaaac ttcctccact 960
ggcgcagggc acatttgctg cctcgattgc cccatgacag tgcccagctg gtgactggta 1020
cttcattctc tgggcctacg gtgggcatgg ccattcagaa ctccatctgt tctcctgact 1080
tctcaggagg tgtgaacatg gaccactcca ccagcatcct gggagtcgcc tcctccatag 1140
cccatgagtt gggccacagc ctgggcctgg accatgattt gcctgggaat agctgcccct 1200
gtccaggtcc agccccagcc aagacctgca tcatggaggc ctccacagac ttcctaccag 1260
gcctgaactt cagcaactgc agccgacggg ccctggagaa agccctcctg gatggaatgg 1320
gcagctgcct cttcgaacgg ctgcctagcc taccccctat ggctgctttc tgcggaaata 1380
tgtttgtgga gccgggcgag cagtgtgact gtggcttcct ggatgactgc gtcgatccct 1440
gctgtgattc tttgacctgc cagctgaggc caggtgcaca gtgtgcatct gacggaccct 1500
gttgtcaaaa ttgccagctg cgcccgtctg gctggcagtg tcgtcctacc agaggggatt 1560
gtgacttgcc tgaattctgc ccaggagaca gctcccagtg tccccctgat gtcagcctag 1620
gggatggcga gccctgcgct ggcgggcaag ctgtgtgcat gcacgggcgt tgtgcctcct 1680
atgcccagca gtgccagtca ctttggggac ctggagccca gcccgctgcg ccactttgcc 1740
tccagacagc taatactcgg ggaaatgctt ttgggagctg tgggcgcaac cccagtggca 1800
gttatgtgtc ctgcacccct agagatgcca tttgtgggca gctccagtgc cagacaggta 1860
ggacccagcc tctgctgggc tccatccggg atctactctg ggagacaata gatgtgaatg 1920
ggactgagct gaactgcagc tgggtgcacc tggacctggg cagtgatgtg gcccagcccc 1980
tcctgactct gcctggcaca gcctgtggcc ctggcctggt gtgtatagac catcgatgcc 2040
agcgtgtgga tctcctgggg gcacaggaat gtcgaagcaa atgccatgga catggggtct 2100
gtgacagcaa caggcactgc tactgtgagg agggctgggc accccctgac tgcaccactc 2160
agctcaaagc aaccagctcc ctgaccacag ggctgctcct cagcctcctg gtcttattgg 2220
tcctggtgat gcttggtgcc agctactggt accgtgcccg cctgcaccag cgactctgcc 2280
agctcaaggg acccacctgc cagtacaggg cagcccaatc tggtccctct gaacggccag 2340
gacctccgca gagggccctg ctggcacgag gcactaaggc tgagctggct gaccgaccca 2400
atccccctac ccgccctctg cccgctgacc cggtggtgag aagcccgaag tctcaggggc 2460
cagccaagcc cccacccccca aggaagccac tgcctgccga cccccagggc cggtgcccat 2520
cgggtgacct gcccggccca ggggctggaa tcccgcccct agtggtaccc tccagaccag 2580
cgccaccgcc tccgacagtg tcctcgctct acctctgacc tctccggagg ttccgctgcc 2640
tccaagccgg acttagggct tcaagaggcg ggcgtgccct ctggagtccc ctaccatgac 2700
tgaaggcgcc agagactggc ggtgtcttaa gactccgggc accgccacgc gctgtcaagc 2760
aacactctgc ggacctgccg gcgtagttgc agcgggggct tggggagggg ctgggggttg 2820
gacgggattg aggaaggtcc gcacagcctg tctctgctca gttgcaataa acgtgacatc 2880
ttgggagcgt tcaaa 2895

<210> SEQ ID NO 14
<211> LENGTH: 2967
<212> TYPE: DNA
<213> ORGANISM: Homo sapiens

<400> SEQUENCE: 14
gcgcggcgct gctgggttct ccgaggcgac ctggccgccg gccgctcctc cgcgcgctgt 60
tccgcacttg ctgccctcgc ccggcccgga gcgccgctgc catgcggctg gcgctgctct 120
gggccctggg gctcctgggc gcgggcagcc ctctgccttc ctggccgctc ccaaatatag 180
gtggcactga ggagcagcag gcagagtcag agaaggcccc gagggagccc ttggagcccc 240
aggtccttca ggacgatctc ccaattagcc tcaaaaaggt gcttcagacc agtctgcctg 300
agcccctgag gatcaagttg gagctggacg gtgacagtca tatcctggag ctgctacaga 360
atagggagtt ggtcccaggc cgcccaaccc tggtgtggta ccagcccgat ggcactcggg 420
tggtcagtga gggacacact ttggagaact gctgctacca gggaagagtg cggggatatg 480
caggctcctg ggtgtccatc tgcacctgct ctgggctcag aggcttggtg gtcctgaccc 540
cagagagaag ctataccctg gagcaggggc ctggggacct tcagggtcct cccattattt 600
cgcgaatcca agatctccac ctgccaggcc acacctgtgc cctgagctgg cgggaatctg 660
tacacactca gaagccacca gagcaccccc tgggacagcg ccacattcgc cggaggcggg 720
atgtggtaac agagaccaag actgtggagt tggtgattgt ggctgatcac tcggaggccc 780
agaaataccg ggacttccag cacctgctaa accgcacact ggaagtggcc ctcttgctgg 840
acacattctt ccggcccctg aatgtacgag tggcactagt gggcctggag gcctggaccc 900
agcgtgacct ggtggagatc agcccaaacc cagctgtcac cctcgaaaac ttcctccact 960
ggcgcagggc acatttgctg cctcgattgc cccatgacag tgcccagctg gtgactggta 1020
cttcattctc tgggcctacg gtgggcatgg ccattcagaa ctccatctgt tctcctgact 1080
tctcaggagg tgtgaacatg gaccactcca ccagcatcct gggagtcgcc tcctccatag 1140
cccatgagtt gggccacagc ctgggcctgg accatgattt gcctgggaat agctgcccct 1200
gtccaggtcc agccccagcc aagacctgca tcatggaggc ctccacagac ttcctaccag 1260
gcctgaactt cagcaactgc agccgacggg ccctggagaa agccctcctg gatggaatgg 1320
gcagctgcct cttcgaacgg ctgcctagcc taccccctat ggctgctttc tgcggaaata 1380
tgtttgtgga gccgggcgag cagtgtgact gtggcttcct ggatgactgc gtcgatccct 1440
gctgtgattc tttgacctgc cagctgaggc caggtgcaca gtgtgcatct gacggaccct 1500
gttgtcaaaa ttgccagctg cgcccgtctg gctggcagtg tcgtcctacc agaggggatt 1560
gtgacttgcc tgaattctgc ccaggagaca gctcccagtg tccccctgat gtcagcctag 1620
gggatggcga gccctgcgct ggcgggcaag ctgtgtgcat gcacgggcgt tgtgcctcct 1680
atgcccagca gtgccagtca ctttggggac ctggagccca gcccgctgcg ccactttgcc 1740
tccagacagc taatactcgg ggaaatgctt ttgggagctg tgggcgcaac cccagtggca 1800
gttatgtgtc ctgcacccct agagatgcca tttgtgggca gctccagtgc cagacaggta 1860
ggacccagcc tctgctgggc tccatccggg atctactctg ggagacaata gatgtgaatg 1920
ggactgagct gaactgcagc tgggtgcacc tggacctggg cagtgatgtg gcccagcccc 1980
tcctgactct gcctggcaca gcctgtggcc ctggcctggt gtgtatagac catcgatgcc 2040
agcgtgtgga tctcctgggg gcacaggaat gtcgaagcaa atgccatgga catggggtct 2100
gtgacagcaa caggcactgc tactgtgagg agggctgggc acccccctgac tgcaccactc 2160 agctcaaagc aaccagctcc ctgaccacag ggctgctcct cagcctcctg gtcttattgg 2220
tcctggtgat gcttggtgcc agctactggt accgtgcccg cctgcaccag cgactctgcc 2280
agctcaaggg acccacctgc cagtacaggg cagcccaatc tggtccctct gaacggccag 2340
gacctccgca gagggccctg ctggcacgag gcactaaggc tagtgctctc agcttcccgg 2400
cccccccttc caggccgctg ccgcctgacc ctgtgtccaa gagactccag gctgagctgg 2460
ctgaccgacc caatccccct acccgccctc tgcccgctga cccggtggtg agaagcccga 2520
agtctcaggg gccagccaag cccccacccc caaggaagcc actgcctgcc gacccccagg 2580
gccggtgccc atcgggtgac ctgcccggcc caggggctgg aatcccgccc ctagtggtac 2640
cctccagacc agcgccaccg cctccgacag tgtcctcgct ctacctctga cctctccgga 2700
ggttccgctg cctccaagcc ggacttaggg cttcaagagg cgggcgtgcc ctctggagtc 2760
ccctaccatg actgaaggcg ccagagactg gcggtgtctt aagactccgg gcaccgccac 2820
gcgctgtcaa gcaacactct gcggacctgc cggcgtagtt gcagcggggg cttggggagg 2880
ggctgggggt tggacgggat tgaggaaggt ccgcacagcc tgtctctgct cagttgcaat 2940
aaacgtgaca tcttgggagc gttcaaa 2967

<210> SEQ ID NO 15
<211> LENGTH: 2970
<212> TYPE: DNA
<213> ORGANISM: Homo sapiens

<400> SEQUENCE: 15
gcgcggcgct gctgggttct ccgaggcgac ctggccgccg gccgctcctc cgcgcgctgt 60
tccgcacttg ctgccctcgc ccggcccgga gcgccgctgc catgcggctg gcgctgctct 120
gggccctggg gctcctgggc gcgggcagcc ctctgccttc ctggccgctc ccaaatatag 180
gtggcactga ggagcagcag gcagagtcag agaaggcccc gagggagccc ttggagcccc 240
aggtccttca ggacgatctc ccaattagcc tcaaaaaggt gcttcagacc agtctgcctg 300

-continued

```
agcccctgag gatcaagttg gagctggacg gtgacagtca tatcctggag ctgctacaga    360
atagggagtt ggtcccaggc cgcccaaccc tggtgtggta ccagcccgat ggcactcggg    420
tggtcagtga gggacacact ttggagaact gctgctacca gggaagagtg cggggatatg    480
caggctcctg ggtgtccatc tgcacctgct ctgggctcag aggcttggtg gtcctgaccc    540
cagagagaag ctataccctg gagcaggggc ctggggacct tcagggtcct cccattattt    600
cgcgaatcca agatctccac ctgccaggcc acacctgtgc cctgagctgg cgggaatctg    660
tacacactca gaagccacca gagcaccccc tgggacagcg ccacattcgc cggaggcggg    720
atgtggtaac agagaccaag actgtggagt tggtgattgt ggctgatcac tcggaggccc    780
agaaataccg ggacttccag cacctgctaa accgcacact ggaagtggcc ctcttgctgg    840
acacattctt ccggcccctg aatgtacgag tggcactagt gggcctggag gcctggaccc    900
agcgtgacct ggtggagatc agcccaaacc cagctgtcac cctcgaaaac ttcctccact    960
ggcgcagggc acatttgctg cctcgattgc cccatgacag tgcccagctg gtgactggta   1020
cttcattctc tgggcctacg gtgggcatgg ccattcagaa ctccatctgt tctcctgact   1080
tctcaggagg tgtgaacatg gaccactcca ccagcatcct gggagtcgcc tcctccatag   1140
cccatgagtt gggccacagc ctgggcctgg accatgattt gcctgggaat agctgcccct   1200
gtccaggtcc agccccagcc aagacctgca tcatggaggc ctccacagac ttcctaccag   1260
gcctgaactt cagcaactgc agccgacggg ccctggagaa agccctcctg gatggaatgg   1320
gcagctgcct cttcgaacgg ctgcctagcc tacccccctat ggctgctttc tgcggaaata   1380
tgtttgtgga gccgggcgag cagtgtgact gtggcttcct ggatgactgc gtcgatccct   1440
gctgtgattc tttgacctgc cagctgaggc caggtgcaca gtgtgcatct gacggaccct   1500
gttgtcaaaa ttgccagctg cgcccgtctg gctggcagtg tcgtcctacc agaggggatt   1560
gtgacttgcc tgaattctgc ccaggagaca gctcccagtg tccccctgat gtcagcctag   1620
gggatggcga gccctgcgct ggcgggcaag ctgtgtgcat gcacgggcgt tgtgcctcct   1680
atgcccagca gtgccagtca ctttggggac ctggagccca gcccgctgcg ccactttgcc   1740
tccagacagc taatactcgg ggaaatgctt ttgggagctg tgggcgcaac cccagtggca   1800
gttatgtgtc ctgcacccct agagatgcca tttgtgggca gctccagtgc cagacaggta   1860
ggacccagcc tctgctgggc tccatccggg atctactctg ggagacaata gatgtgaatg   1920
ggactgagct gaactgcagc tgggtgcacc tggacctggg cagtgatgtg gcccagcccc   1980
tcctgactct gcctggcaca gcctgtggcc ctggcctggt gtgtatagac catcgatgcc   2040
agcgtgtgga tctcctgggg gcacaggaat gtcgaagcaa atgccatgga catggggtct   2100
gtgacagcaa caggcactgc tactgtgagg agggctgggc accccctgac tgcaccactc   2160
agctcaaagc aaccagctcc ctgaccacag ggctgctcct cagcctcctg gtcttattgg   2220
tcctggtgat gcttggtgcc agctactggt accgtgcccg cctgcaccag cgactctgcc   2280
agctcaaggg acccacctgc cagtacaggg cagcccaatc tggtccctct gaacggccag   2340
gacctccgca gagggccctg ctggcacgag gcactaagca ggctagtgct ctcagcttcc   2400
cggccccccc ttccaggccg ctgccgcctg accctgtgtc caagagactc caggctgagc   2460
tggctgaccg acccaatccc cctacccgcc ctctgcccgc tgacccggtg gtgagaagcc   2520
cgaagtctca ggggccagcc aagcccccac ccccaaggaa gccactgcct gccgaccccc   2580
agggccggtg cccatcgggt gacctgcccg gcccaggggc tggaatcccg cccctagtgg   2640
```

-continued

```
taccctccag accagcgcca ccgcctccga cagtgtcctc gctctacctc tgacctctcc   2700

ggaggttccg ctgcctccaa gccggactta gggcttcaag aggcgggcgt gccctctgga   2760

gtcccctacc atgactgaag gcgccagaga ctggcggtgt cttaagactc cgggcaccgc   2820

cacgcgctgt caagcaacac tctgcggacc tgccggcgta gttgcagcgg gggcttgggg   2880

aggggctggg ggttggacgg gattgaggaa ggtccgcaca gcctgtctct gctcagttgc   2940

aataaacgtg acatcttggg agcgttcaaa                                    2970
```

<210> SEQ ID NO 16
<211> LENGTH: 2786
<212> TYPE: DNA
<213> ORGANISM: Homo sapiens

<400> SEQUENCE: 16

```
gcggaggcaa ggcgggtgca gggcttctgg ggacggaggg aggtgccaga agttgagccc     60

tgaggccctg ctggccccctg ggcgcaggcc cagctcaggc ccccagggat ggacgtcgtg   120

gaccctgaca ttttcaatag agacccccgg gaccactatg acctgctaca gcggctgggt   180

ggcggcacgt atggggaagt ctttaaggct cgagacaagg tgtcagggga cctggtggca   240

ctgaagatgg tgaagatgga gcctgatgat gatgtctcca cccttcagaa ggaaatcctc   300

atattgaaaa cttgccggca cgccaacatc gtggcctacc atgggagtta tctctggttg   360

cagaaactct ggatctgcat ggaattctgt ggggctggtt ctctccagga catctaccaa   420

gtgacaggct ccctgtcaga gctccagatt agctatgtct gccgggaagt gctccaggga   480

ctggcctatt tgcactcaca gaagaagata cacagggaca tcaagggagc taacatcctc   540

atcaatgatg ctggggaggt cagattggct gactttggca tctcggccca gattggggct   600

acactggcca gacgcctctc tttcattggg acaccctact ggatggctcc ggaagtggca   660

gctgtggccc tgaagggagg atacaatgag ctgtgtgaca tctggtccct gggcatcacg   720

gccatcgaac tggccgagct acagccaccg ctctttgatg tgcaccctct cagagttctc   780

ttcctcatga ccaagagtgg ctaccagcct ccccgactga aggaaaaagg caaatggtcg   840

gctgccttcc acaacttcat caaagtcact ctgactaaga gtcccaagaa acgacccagc   900

gccaccaaga tgctcagtca tcaactggta tcccagcctg ggctgaatcg aggcctgatc   960

ctggatcttc ttgacaaact gaagaatccc gggaaaggac cctccattgg ggacattgag  1020

gatgaggagc ccgagctacc ccctgctatc cctcggcgga tcagatccac ccaccgctcc  1080

agctctctgg ggatcccaga tgcagactgc tgtcggcggc acatggagtt caggaagctc  1140

cgaggaatgg agaccagacc cccagccaac accgctcgcc tacagcctcc tcgagacctc  1200

aggagcagca gccccaggaa gcaactgtca gagtcgtctg acgatgacta tgacgacgtg  1260

gacatcccca cccctgcaga ggacacacct cctccacttc cccccaagcc caagttccgt  1320

tctccatcag acgagggtcc tgggagcatg gggatgatg ggcagctgag cccgggggtg  1380

ctggtccggt gtgccagtgg gcccccacca aacagccccc gtcctgggcc tcccccatcc  1440

accagcagcc cccacctcac cgcccattca gaaccctcac tctggaaccc accctcccgg  1500

gagcttgaca agcccccact tctgcccccc aagaaggaaa agatgaagag aaagggatgt  1560

gcccttctcg taaagttgtt caatggctgc cccctccgga tccacagcac ggccgcctgg  1620

acacatccct ccaccaagga ccagcacctg ctcctggggg cagaggaagg catcttcatc  1680

ctgaaccgga atgaccagga ggccacgctg gaaatgctct ttcctagccg gactacgtgg  1740

gtgtactcca tcaacaacgt tctcatgtct ctctcaggaa agaccccccca cctgtattct  1800
```

-continued

```
catagcatcc ttggcctgct ggaacggaaa gagaccagag caggaaaccc catcgctcac   1860

attagccccc accgcctact ggcaaggaag aacatggttt ccaccaagat ccaggacacc   1920

aaaggctgcc gggcgtgctg tgtggcggag ggtgcgagct ctgggggccc gttcctgtgc   1980

ggtgcattgg agacgtccgt tgtcctgctt cagtggtacc agcccatgaa caaattcctg   2040

cttgtccggc aggtgctgtt cccactgccg acgcctctgt ccgtgttcgc gctgctgacc   2100

gggccaggct ctgagctgcc cgctgtgtgc atcggcgtga gccccgggcg gccggggaag   2160

tcggtgctct tccacacggt gcgctttggc gcgctctctt gctggctggg cgagatgagc   2220

accgagcaca ggggacccgt gcaggtgacc caggtagagg aagatatggt gatggtgttg   2280

atggatggct ctgtgaagct ggtgaccccg gaggggtccc cagtccgggg acttcgcaca   2340

cctgagatcc ccatgaccga agcggtggag gccgtggcta tggttggagg tcagcttcag   2400

gccttctgga agcatggagt gcaggtgtgg gctctaggct cggatcagct gctacaggag   2460

ctgagagacc ctaccctcac tttccgtctg cttggctccc ccaggctgga gtgcagtggc   2520

acgatctcgc ctcactgcaa cctcctcctc ccaggttcaa gcaattctcc tgcctcagcc   2580

tcccgagtag ctgggattac aggcctgtag tggtggagac acgcccagtg gatgatccta   2640

ctgctcccag caacctctac atccaggaat gagtccctag gggggtgtca ggaactagtc   2700

cttgcacccc ctcccccata gacacactag tggtcatggc atgtcctcat ctcccaataa   2760

acatgacttt agcctctgca aaaaaa                                        2786
```

<210> SEQ ID NO 17
<211> LENGTH: 1084
<212> TYPE: DNA
<213> ORGANISM: Homo sapiens

<400> SEQUENCE: 17

```
aatgagcatc caaaagacgt atctggaggg agattttgtc tttcctgtga gcagcagcag     60

cttcctacgg accctgctgg agccccagct cggatcagcc cttctgacag caatgaatgc    120

ttcgtgctgc ctgccctctg ttcagccaac actgcctaat ggctcggagc acctccaagc    180

ccctttcttc agcaaccaga gcagcagcgc cttctgtgag caggtcttca tcaagcccga    240

ggttttcctg tctctgggca tcgtcagtct gctggaaaac atcctggtta tcctggccgt    300

ggtcaggaac ggcaacctgc actccccgat gtacttcttt ctctgcagcc tggcggtggc    360

cgacatgctg gtaagtgtgt ccaatgccct ggagaccatc atgatcgcca tcgtccacag    420

cgactacctg accttcgagg accagtttat ccagcacatg gacaacatct tcgactccat    480

gatctgcatc tccctggtgg cctccatctg caacctcctg gccatcgccg tcgacaggta    540

cgtcaccatc ttttacgcgc tccgctacca cagcatcatg accgtgagga aggccctcac    600

cttgatcgtg gccatctggg tctgctgcgg cgtctgtggc gtggtgttca tcgtctactc    660

ggagagcaaa atggtcattg tgtgcctcat caccatgttc ttcgccatga tgctcctcat    720

gggcaccctc tacgtgcaca tgttcctctt tgcgcggctg cacgtcaagc gcatagcagc    780

actgccacct gccgacgggg tggccccaca gcaacactca tgcatgaagg gggcagtcac    840

catcaccatt ctcctgggcg tgttcatctt ctgctgggcc cccttcttcc tccacctggt    900

cctcatcatc acctgcccca ccaaccccta ctgcatctgc tacactgccc acttcaacac    960

ctacctggtc ctcatcatgt gcaactccgt catcgaccca ctcatctacg ctttccggag   1020

cctggaattg cgcaacacct ttagggagat tctctgtggc tgcaacggca tgaacttggg   1080
```

-continued atag 1084

<210> SEQ ID NO 18
<211> LENGTH: 3349
<212> TYPE: DNA
<213> ORGANISM: Homo sapiens

<400> SEQUENCE: 18
ggtggactga gccgctcggg acagcggcac cggaggaggc tcggagaaga tgcggggctc 60
ggggccccgg ggtgcgggac accggcggcc cccaagcggc ggcggcgaca cccccatcac 120
cccagcgtcc ctggccggct gctactctgc acctcgacgg gctcccctct ggacgtgcct 180
tctcctgtgc gccgcactcc ggaccctcct ggccagcccc agcaacgaag tgaatttatt 240
ggattcacgc actgtcatgg gggacctggg atggattgct tttccaaaaa atgggtggga 300
agagattggt gaagtggatg aaaattatgc ccctatccac acataccaag tatgcaaagt 360
gatggaacag aatcagaata actggctttt gaccagttgg atctccaatg aaggtgcttc 420
cagaatcttc atagaactca aatttaccct gcgggactgc aacagccttc ctggaggact 480
ggggacctgt aaggaaacct ttaatatgta ttactttgag tcagatgatc agaatgggag 540
aaacatcaag gaaaaccaat acatcaaaat tgataccatt gctgccgatg aaagctttac 600
agaacttgat cttggtgacc gtgttatgaa actgaataca gaggtcagag atgtaggacc 660
tctaagcaaa aagggatttt atcttgcttt tcaagatgtt ggtgcttgca ttgctctggt 720
ttctgtgcgt gtatactata aaaaatgccc ttctgtggta cgacacttgg ctgtcttccc 780
tgacaccatc actggagctg attcttccca attgctcgaa gtgtcaggct cctgtgtcaa 840
ccattctgtg accgatgaac ctcccaaaat gcactgcagc gccgaagggg agtggctggt 900
gcccatcggg aaatgcatgt gcaaggcagg atatgaagag aaaaatggca cctgtcaagt 960
gtgcagacct gggttcttca aagcctcacc tcacatccag agctgcggca aatgtccacc 1020
tcacagttat acccatgagg aagcttcaac ctcttgtgtc tgtgaaaagg attatttcag 1080
gagagagtct gatccaccca caatggcatg cacaagaccc ccctctgctc ctcggaatgc 1140
catctcaaat gttaatgaaa ctagtgtctt tctggaatgg attccgcctg ctgacactgg 1200
tggaaggaaa gacgtgtcat attatattgc atgcaagaag tgcaactccc atgcaggtgt 1260
gtgtgaggag tgtggcggtc atgtcaggta ccttccccgg caaagcggcc tgaaaaacac 1320
ctctgtcatg atggtggatc tactcgctca cacaaactat acctttgaga ttgaggcagt 1380
gaatggagtg tccgacttga gcccaggagc ccggcagtat gtgtctgtaa atgtaaccac 1440
aaatcaagca gctccatctc cagtcaccaa tgtgaaaaaa gggaaaattg caaaaaacag 1500
catctctttg tcttggcaag aaccagatcg tcccaatgga atcatcctag agtatgaaat 1560
caagtatttt gaaaaggacc aagagaccag ctacacgatt atcaaatcta aagagacaac 1620
tattactgca gagggcttga aaccagcttc agtttatgtc ttccaaattc gagcacgtac 1680
agcagcaggc tatggtgtct tcagtcgaag atttgagttt gaaaccaccc cagtgtttgc 1740
agcatccagc gatcaaagcc agattcctgt aattgctgtg tctgtgacag tgggagtcat 1800
tttgttggca gtggttatcg gcgtcctcct cagtggaagt tgctgcgaat gtggctgtgg 1860
gagggcttct tccctgtgcg ctgttgccca tccaagccta atatggcggt gtggctacag 1920
caaagcaaaa caagatccag aagaggaaaa gatgcatttt cataatgggc acattaaact 1980
gccaggagta agaacttaca ttgatccaca tacctatgag gatcccaatc aagctgtcca 2040
cgaatttgct aaggagatag aagcatcatg tatcaccatt gagagagtta ttggagcagg 2100

```
tgaatttggt gaagtttgta gtggacgttt gaaactacca ggaaaaagag aattacctgt   2160
ggctatcaaa acccttaaag taggctatac tgaaaagcaa cgcagagatt tcctaggtga   2220
agcaagtatc atgggacagt ttgatcatcc taacatcatc catttagaag gtgtggtgac   2280
caaaagtaaa ccagtgatga tcgtgacaga gtatatggag aatggctctt tagatacatt   2340
tttgaagaaa aacgatgggc agttcactgt gattcagctt gttggcatgc tgagaggtat   2400
ctctgcagga atgaagtacc tttctgacat gggctatgtg catagagatc ttgctgccag   2460
aaacatctta atcaacagta accttgtgtg caaagtgtct gactttggac tttcccgggt   2520
actggaagat gatcccgagg cagcctacac cacaagggga ggaaaaattc caatcagatg   2580
gactgcccca gaagcaatag ctttccgaaa gtttacttct gccagtgatg tctggagtta   2640
tggaatagta atgtgggaag ttgtgtctta tggagagaga ccctactggg agatgaccaa   2700
tcaagatgtg attaaagcgg tagaggaagg ctatcgtctg ccaagcccca tggattgtcc   2760
tgctgctctc tatcagttaa tgctggattg ctggcagaaa gagcgaaata gcaggcccaa   2820
gtttgatgaa atagtcaaca tgttggacaa gctgatacgt aacccaagta gtctgaagac   2880
gctggttaat gcatcctgca gagtatctaa tttattggca gaacatagcc cactaggatc   2940
tggggcctac agatcagtag gtgaatggct agaggcaatc aagatgggcc ggtatacaga   3000
gattttcatg gaaaatggat acagttcaat ggacgctgtg gctcaggtga ccttggagga   3060
tttgagacgg cttggagtga ctcttgtcgg tcaccagaag aagatcatga acagccttca   3120
agaaatgaag gtgcagctgg taaacggaat ggtgccattg taacttcatg taaatgtcgc   3180
ttcttcaagt gaatgattct gcactttgta aacagcactg agatttattt taacaaaaaa   3240
agggggaaaa gggaaaacag tgatttctaa accttagaaa acatttgcct cagccacaga   3300
atttgtaatc atggttttac tgaagtatcc agttcttagt ccttagtct              3349
```

<210> SEQ ID NO 19
<211> LENGTH: 3283
<212> TYPE: DNA
<213> ORGANISM: Homo sapiens

<400> SEQUENCE: 19

```
ggtggactga gccgctcggg acagcggcac cggaggaggc tcggagaaga tgcggggctc     60
ggggccccgg ggtgcgggac accggcggcc cccaagcggc ggcggcgaca cccccatcac    120
cccagcgtcc ctggccggct gctactctgc acctcgacgg gctcccctct ggacgtgcct    180
tctcctgtgc gccgcactcc ggaccctcct ggccagcccc agcaacgaag tgaatttatt    240
ggattcacgc actgtcatgg gggacctggg atggattgct tttccaaaaa atgggtggga    300
agagattggt gaagtggatg aaaattatgc ccctatccac acataccaag tatgcaaagt    360
gatggaacag aatcagaata actggctttt gaccagttgg atctccaatg aaggtgcttc    420
cagaatcttc atagaactca aatttaccct gcgggactgc aacagccttc ctggaggact    480
ggggacctgt aaggaaacct ttaatatgta ttactttgag tcagatgatc agaatgggag    540
aaacatcaag gaaaaccaat acatcaaaat tgataccatt gctgccgatg aaagctttac    600
agaacttgat cttggtgacc gtgttatgaa actgaataca gaggtcagag atgtaggacc    660
tctaagcaaa aagggatttt atcttgcttt tcaagatgtt ggtgcttgca ttgctctggt    720
ttctgtgcgt gtatactata aagaatgccc ttctgtggta cgacacttgg ctgtcttccc    780
tgacaccatc actggagctg attcttccca attgctcgaa gtgtcaggct cctgtgtcaa    840
```

-continued

```
ccattctgtg accgatgaac ctcccaaaat gcactgcagc gccgaagggg agtggctggt    900
gcccatcggg aaatgcatgt gcaaggcagg atatgaagag aaaaatggca cctgtcaagt    960
gtgcagacct gggttcttca aagcctcacc tcacatccag agctgcggca aatgtccacc   1020
tcacagttat acccatgagg aagcttcaac ctcttgtgtc tgtgaaaagg attatttcag   1080
gagagagtct gatccaccca caatggcatg cacaagaccc ccctctgctc ctcggaatgc   1140
catctcaaat gttaatgaaa ctagtgtctt tctggaatgg attccgcctg ctgacactgg   1200
tggaaggaaa gacgtgtcat attatattgc atgcaagaag tgcaactccc atgcaggtgt   1260
gtgtgaggag tgtggcggtc atgtcaggta ccttccccgg caaagcggcc tgaaaaacac   1320
ctctgtcatg atggtggatc tactcgctca cacaaactat acctttgaga ttgaggcagt   1380
gaatggagtg tccgacttga gcccaggagc ccggcagtat gtgtctgtaa atgtaaccac   1440
aaatcaagca gctccatctc cagtcaccaa tgtgaaaaaa gggaaaattg caaaaaacag   1500
catctctttg tcttggcaag aaccagatcg tcccaatgga atcatcctag agtatgaaat   1560
caagtatttt gaaaaggacc aagagaccag ctacacgatt atcaaatcta aagagacaac   1620
tattactgca gagggcttga aaccagcttc agtttatgtc ttccaaattc gagcacgtac   1680
agcagcaggc tatggtgtct tcagtcgaag atttgagttt gaaaccaccc cagtgtttgc   1740
agcatccagc gatcaaagcc agattcctgt aattgctgtg tctgtgacag tgggagtcat   1800
tttgttggca gtggttatcg gcgtcctcct cagtggaagg cggtgtggct acagcaaagc   1860
aaaacaagat ccagaagagg aaaagatgca ttttcataat gggcacatta aactgccagg   1920
agtaagaact tacattgatc cacataccta tgaggatccc aatcaagctg tccacgaatt   1980
tgctaaggag atagaagcat catgtatcac cattgagaga gttattggag caggtgaatt   2040
tggtgaagtt tgtagtggac gtttgaaact accaggaaaa agagaattac ctgtggctat   2100
caaaaccctt aaagtaggct atactgaaaa gcaacgcaga gatttcctag gtgaagcaag   2160
tatcatggga cagtttgatc atcctaacat catccattta gaaggtgtgg tgaccaaaag   2220
taaaccagtg atgatcgtga cagagtatat ggagaatggc tctttagata catttttgaa   2280
gaaaaacgat gggcagttca ctgtgattca gcttgttggc atgctgagag gtatctctgc   2340
aggaatgaag tacctttctg acatgggcta tgtgcataga gatcttgctg ccagaaacat   2400
cttaatcaac agtaaccttg tgtgcaaagt gtctgacttt ggactttccc gggtactgga   2460
agatgatccc gaggcagcct acaccacaag ggaggaaaa attccaatca gatggactgc   2520
cccagaagca atagctttcc gaaagtttac ttctgccagt gatgtctgga gttatggaat   2580
agtaatgtgg gaagttgtgt cttatggaga gagaccctac tgggagatga ccaatcaaga   2640
tgtgattaaa gcggtagagg aaggctatcg tctgccaagc cccatggatt gtcctgctgc   2700
tctctatcag ttaatgctgg attgctggca gaaagagcga aatagcaggc ccaagtttga   2760
tgaaatagtc aacatgttgg acaagctgat acgtaaccca agtagtctga agacgctggt   2820
taatgcatcc tgcagagtat ctaatttatt ggcagaacat agcccactag gatctggggc   2880
ctacagatca gtaggtgaat ggctagaggc aatcaagatg ggccggtata cagagatttt   2940
catggaaaat ggatacagtt caatggacgc tgtggctcag gtgaccttgg aggatttgag   3000
acggcttgga gtgactcttg tcggtcacca gaagaagatc atgaacagcc ttcaagaaat   3060
gaaggtgcag ctggtaaacg gaatggtgcc attgtaactt catgtaaatg tcgcttcttc   3120
aagtgaatga ttctgcactt tgtaaacagc actgagattt attttaacaa aaaaaggggg   3180
aaaagggaaa acagtgattt ctaaacctta gaaaacattt gcctcagcca cagaatttgt   3240
```

-continued aatcatggtt ttactgaagt atccagttct tagtccttag tct 3283

<210> SEQ ID NO 20
<211> LENGTH: 2921
<212> TYPE: DNA
<213> ORGANISM: Homo sapiens

<400> SEQUENCE: 20
ccccgctggc agacgctggc ggcgtaaggc gcgcgggccc cggagcgggc gcggcggagc 60
gcggcgagcc cggcgcctcc cgtcccgaac atgcggaggc cggcccaggc ggcgcgggag 120
ccggagcggg ggcccaagcg ggcaccggag ccggagcgcg agggggcgcg gggcccggag 180
cgggggtccg cgctgcgctg ctgaggccgg gccggccgcc cagacgctgc ccgcgggccc 240
ggccacggcg gagccaagct gtgagccgtg agctttgagg cggtgggatg tgtcagcaga 300
atgtctcctg cccccgagag cgaccccgag gccactgaga agagcagcgc ggcctggccg 360
gcccgaacgc ctgcgtctca gtagctggga gccacgggcc cacgcccgcc caccggccgc 420
agtgatgttc tagccacaga ggagccaaga cctcaggttt ccagagactt gggatttgca 480
cggcagcaga gtcaccgtgg agaggccagg gtatcacaaa cttatggatt ttgacaagaa 540
aggagggaaa ggggagacgg aggagggccg gagaatgtcc aaggccggcg ggggccggag 600
cagccacggc atccggagct cggggaccag ctcgggggtc ctgatggtgg gccccaactt 660
ccgcgtcggc aagaagatcg gctgcggcaa cttcggggag ctccgcctag gaaagaatct 720
ctatacaaat gaatacgtgg ctatcaaatt ggagccgatc aagtcccggg ccccgcagct 780
gcacctggag taccggttct acaagcagct cagcgccaca gagggcgtcc ctcaggtcta 840
ctacttcggt ccgtgcggga agtacaacgc catggtgctg gagctgctgg ggcccagcct 900
ggaggacctg ttcgacctgt gcgaccggac cttcacgctc aagacggtgc tgatgatcgc 960
catccagctg atcacgcgca tggagtatgt gcacaccaag agcctaatct accgggacgt 1020
gaagcccgag aacttcctgg tgggccgccc ggggaccaag cggcagcatg ccatccacat 1080
catcgacttc gggctggcca aggagtacat cgaccccgag accaagaagc acatcccgta 1140
ccgcgagcac aagagcctga cgggcacggc gcgctacatg agcatcaaca cgcacctggg 1200
caaggagcag agccgccgcg acgacctgga ggcgctgggc cacatgttca tgtacttcct 1260
gcgcggcagc ctcccctggc aggggctcaa ggccgacacg ctcaaggagc ggtaccagaa 1320
gatcggggac accaaacgcg ccacgcccat cgaggtgctc tgcgagaact tcccagagga 1380
gatggccacg tacctgcgct atgtgcggcg cctggacttc ttcgagaagc ccgactatga 1440
ctacctgcgg aagctcttca ccgacctctt cgaccgcagt ggcttcgtgt tcgactatga 1500
gtacgactgg gccgggaagc ccctgccgac ccccatcggc accgtccaca ccgacctgcc 1560
ctcccagcct cagctccggg acaaaaccca gccgcacagc aaaaaccagg cgttgaactc 1620
caccaacggg gagctgaatg cggacgaccc cacggccggc cactccaacg ccccgatcac 1680
agcgcctgca gaggtggagg tggccgatga aaccaaatgc tgctgtttct tcaagaggag 1740
aaagagaaaa tcgctgcagc gacacaagtg accctgggcg cgtgcagccc cctgaatctt 1800
ctccgtgcag ccccttgggg cgcgaccttg tgcgaggccc tcggggccca cccacagcgg 1860
cccagggcca gaccctggct ggaagccaga acgcagactg caggggccgc gcctggctca 1920
ggcggcccca cccccgggac gtggggtcac ttccttcatg taagactttg gccgaaattt 1980
ctacacctgt gtctagtcct cccctccaag agcattaact atttaaaaca aggaaaagag 2040

```
gaaaaaaaaa acagaggccc gccctacccc actcctgccc ctccgtttct ttgctgaagt   2100

gagtagtgtg atcctggagg ccccccggcc tggccccgcc ccgccagccg cccccgttag   2160

cgtcataaag tccagcttgt ctccctcgat ccaaaggccg ttttctcgag gggagggcag   2220

gcccggcctg gaggggtgct gtggagctgt cttgcccagg ccctcctggg agggggacag   2280

gcattgttgc caggggtgag gccgtgcccc aggcctcccc gaaaccaaag gggaaggcag   2340

gggtggggcc gtggctgaag ccggctcccc aaccaaaatg ctgcaccaaa gctcgggcgc   2400

cgcgggcacg gctgctgcag tctcttccca gcctggccct ggcaaggggc gggtgggcgc   2460

tgccaggcgg gtgcttctcg acgcacttgc tcccggaggc tgcgccccgg cgcctggaac   2520

ccgaggtggg aggaccggtt ggtgtcaccc tgctcggccc tcagccctgc cgcgtggggc   2580

gcgtgggcac ggagcttcct gcctctctgc tccgacaccc ggcaagcagc cggagacaaa   2640

acgccttaaa gcccccggcc cagccctgca ggtatattgc aggggcctgg gggcggccct   2700

ggactggcgg gcggttcccc agtggggtgc cctggaggct gccgggcaga gtggagcagc   2760

ttggggccgt gcccagggcg gtggctgtga gtctagtttt tgctttacca agtgtacaga   2820

aatggcattt acgtttctct gatgctccct tgaagccata gaatttaggg gctttttttaa   2880

aaaaataaaa gaaaaatgaa accaaaaaaa aaaaaaaaaa a                       2921
```

<210> SEQ ID NO 21
<211> LENGTH: 1803
<212> TYPE: DNA
<213> ORGANISM: Homo sapiens

<400> SEQUENCE: 21

```
ctcccgcgcc ctctcagcaa cccgcacagg gcgcacccgg acgctctacc gctcccgccg     60

cagtcgccgg gccatgggcc tcgagcccgc cccgaacccc cgcgagcccg ccttgtctgc    120

ggcgtgactg gaggcccaga tggtcatcat gggccagtgc tactacaacg agaccatcgg    180

cttcttctat aacaacagtg gcaaagagct cagctcccac tggcggccca aggatgtggt    240

cgtggtggca ctggggctga ccgtcagcgt gctggtgctg ctgaccaatc tgctggtcat    300

agcagccatc gcctccaacc gccgcttcca ccagcccatc tactacctgc tcggcaatct    360

ggccgcggct gacctcttcg cgggcgtggc ctacctcttc ctcatgttcc acactggtcc    420

ccgcacagcc cgactttcac ttgagggctg gttcctgcgg cagggcttgc tggacacaag    480

cctcactgcg tcggtggcca cactgctggc catcgccgtg gagcggcacc gcagtgtgat    540

ggccgtgcag ctgcacagcc gcctgccccg tggccgcgtg gtcatgctca ttgtgggcgt    600

gtgggtggct gccctgggcc tggggctgct gcctgcccac tcctggcact gcctctgtgc    660

cctggaccgc tgctcacgca tggcacccct gctcagccgc tcctatttgg ccgtctgggc    720

tctgtcgagc ctgcttgtct tcctgctcat ggtggctgtg tacacccgca ttttcttcta    780

cgtgcggcgg cgagtgcagc gcatggcaga gcatgtcagc tgccaccccc gctaccgaga    840

gaccacgctc agcctggtca agactgttgt catcatcctg gggcgttcg tggtctgctg    900

gacaccaggc caggtggtac tgctcctgga tggtttaggc tgtgagtcct gcaatgtcct    960

ggctgtagaa aagtacttcc tactgttggc cgaggccaac tcactggtca atgctgctgt   1020

gtactcttgc cgagatgctg agatgcgccg caccttccgc cgccttctct gctgcgcgtg   1080

cctccgccag tccacccgcg agtctgtcca ctatacatcc tctgcccagg gaggtgccag   1140

cactcgcatc atgcttcccg agaacggcca cccactgatg gactccaccc tttagctacc   1200

ttgaacttca gcggtacgcg gcaagcaaca aatccacagc ccctgatgac ttgtgggtgc   1260
```

```
tcctggctca acccaaccaa caggactgac tgactggcag gacaaggtct ggcatggcac   1320

agcaccactg ccaggcctcc ccaggcacac cactctgccc agggaatggg ggctttgggt   1380

catctcccac tgcctggggg agtcagatgg ggtgcaggaa tctggctctt cagccatctc   1440

aggtttaggg ggtttgtaac agacattatt ctgttttcac tgcgtatcct tggtaagccc   1500

tgtggactgg ttcctgctgt gtgatgctga gggttttaag gtggggagag ataagggctc   1560

tctcgggcca tgctacccgg tatgactggg taatgaggac agactgtgga caccccatct   1620

acctgagtct gattctttag cagcagagac tgaggggtgc agagtgtgag ctgggaaagg   1680

tttgtggctc cttgcagcct ccagggactg gcctgtcccc gatagaattg aagcagtcca   1740

cggggagggg atgatacaag gagtaaacct ttctttacac tctgaggtct ccaaaaaaaa   1800

aaa                                                                 1803
```

<210> SEQ ID NO 22
<211> LENGTH: 1390
<212> TYPE: PRT
<213> ORGANISM: Homo sapiens

<400> SEQUENCE: 22

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270
```

```
Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685
```

```
His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
```

```
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155

Tyr Met  Lys His Gly Asp Leu  Arg Asn Phe Ile Arg  Asn Glu Thr
    1160                1165                1170

His Asn  Pro Thr Val Lys Asp  Leu Ile Gly Phe Gly  Leu Gln Val
    1175                1180                1185

Ala Lys  Gly Met Lys Tyr Leu  Ala Ser Lys Lys Phe  Val His Arg
    1190                1195                1200

Asp Leu  Ala Ala Arg Asn Cys  Met Leu Asp Glu Lys  Phe Thr Val
    1205                1210                1215

Lys Val  Ala Asp Phe Gly Leu  Ala Arg Asp Met Tyr  Asp Lys Glu
    1220                1225                1230

Tyr Tyr  Ser Val His Asn Lys  Thr Gly Ala Lys Leu  Pro Val Lys
    1235                1240                1245

Trp Met  Ala Leu Glu Ser Leu  Gln Thr Gln Lys Phe  Thr Thr Lys
    1250                1255                1260

Ser Asp  Val Trp Ser Phe Gly  Val Leu Leu Trp Glu  Leu Met Thr
    1265                1270                1275

Arg Gly  Ala Pro Pro Tyr Pro  Asp Val Asn Thr Phe  Asp Ile Thr
    1280                1285                1290

Val Tyr  Leu Leu Gln Gly Arg  Arg Leu Leu Gln Pro  Glu Tyr Cys
    1295                1300                1305

Pro Asp  Pro Leu Tyr Glu Val  Met Leu Lys Cys Trp  His Pro Lys
    1310                1315                1320

Ala Glu  Met Arg Pro Ser Phe  Ser Glu Leu Val Ser  Arg Ile Ser
    1325                1330                1335

Ala Ile  Phe Ser Thr Phe Ile  Gly Glu His Tyr Val  His Val Asn
    1340                1345                1350

Ala Thr  Tyr Val Asn Val Lys  Cys Val Ala Pro Tyr  Pro Ser Leu
    1355                1360                1365

Leu Ser  Ser Glu Asp Asn Ala  Asp Asp Glu Val Asp  Thr Arg Pro
    1370                1375                1380

Ala Ser  Phe Trp Glu Thr Ser
    1385                1390


<210> SEQ ID NO 23
<211> LENGTH: 414
<212> TYPE: PRT
<213> ORGANISM: Homo sapiens

<400> SEQUENCE: 23

Met Gly Gly Asn His Ser His Lys Pro Pro Val Phe Asp Glu Asn Glu
1               5                   10                  15

Glu Val Asn Phe Asp His Phe Gln Ile Leu Arg Ala Ile Gly Lys Gly
            20                  25                  30

Ser Phe Gly Lys Val Cys Ile Val Gln Lys Arg Asp Thr Lys Lys Met
        35                  40                  45

Tyr Ala Met Lys Tyr Met Asn Lys Gln Lys Cys Ile Glu Arg Asp Glu
    50                  55                  60
```

-continued

```
Val Arg Asn Val Phe Arg Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
            100                 105                 110

Gln Gln Asn Val His Phe Thr Glu Gly Thr Val Lys Leu Tyr Ile Cys
        115                 120                 125

Glu Leu Ala Leu Ala Leu Glu Tyr Leu Gln Arg Tyr His Ile Ile His
    130                 135                 140

Arg Asp Ile Lys Pro Asp Asn Ile Leu Leu Asp Glu His Gly His Val
145                 150                 155                 160

His Ile Thr Asp Phe Asn Ile Ala Thr Val Val Lys Gly Ala Glu Arg
                165                 170                 175

Ala Ser Ser Met Ala Gly Thr Lys Pro Tyr Met Ala Pro Glu Val Phe
            180                 185                 190

Gln Val Tyr Met Asp Arg Gly Pro Gly Tyr Ser Tyr Pro Val Asp Trp
        195                 200                 205

Trp Ser Leu Gly Ile Thr Ala Tyr Glu Leu Leu Arg Gly Trp Arg Pro
    210                 215                 220

Tyr Glu Ile His Ser Val Thr Pro Ile Asp Glu Ile Leu Asn Met Phe
225                 230                 235                 240

Lys Val Glu Arg Val His Tyr Ser Ser Thr Trp Cys Lys Gly Met Val
                245                 250                 255

Ala Leu Leu Arg Lys Leu Leu Thr Lys Asp Pro Glu Ser Arg Val Ser
            260                 265                 270

Ser Leu His Asp Ile Gln Ser Val Pro Tyr Leu Ala Asp Met Asn Trp
        275                 280                 285

Asp Ala Val Phe Lys Lys Ala Leu Met Pro Gly Phe Val Pro Asn Lys
    290                 295                 300

Gly Arg Leu Asn Cys Asp Pro Thr Phe Glu Leu Glu Glu Met Ile Leu
305                 310                 315                 320

Glu Ser Lys Pro Leu His Lys Lys Lys Lys Arg Leu Ala Lys Asn Arg
                325                 330                 335

Ser Arg Asp Gly Thr Lys Asp Ser Cys Pro Leu Asn Gly His Leu Gln
            340                 345                 350

His Cys Leu Glu Thr Val Arg Glu Glu Phe Ile Ile Phe Asn Arg Glu
        355                 360                 365

Lys Leu Arg Arg Gln Gln Gly Gln Gly Ser Gln Leu Leu Asp Thr Asp
    370                 375                 380

Ser Arg Gly Gly Gly Gln Ala Gln Ser Lys Leu Gln Asp Gly Cys Asn
385                 390                 395                 400

Asn Asn Leu Leu Thr His Thr Cys Thr Arg Gly Cys Ser Ser
                405                 410


<210> SEQ ID NO 24
<211> LENGTH: 381
<212> TYPE: PRT
<213> ORGANISM: Homo sapiens

<400> SEQUENCE: 24

Met Arg Ser His Thr Ile Thr Met Thr Thr Thr Ser Val Ser Ser Trp
1               5                   10                  15

Pro Tyr Ser Ser His Arg Met Arg Phe Ile Thr Asn His Ser Asp Gln
            20                  25                  30
```

```
Pro Pro Gln Asn Phe Ser Ala Thr Pro Asn Val Thr Thr Cys Pro Met
        35                  40                  45

Asp Glu Lys Leu Leu Ser Thr Val Leu Thr Thr Ser Tyr Ser Val Ile
    50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Ala Ile Ala Asp Leu Leu Leu Ile Phe Cys Leu Pro Phe Arg Ile Met
            100                 105                 110

Tyr His Ile Asn Gln Asn Lys Trp Thr Leu Gly Val Ile Leu Cys Lys
        115                 120                 125

Val Val Gly Thr Leu Phe Tyr Met Asn Met Tyr Ile Ser Ile Ile Leu
    130                 135                 140

Leu Gly Phe Ile Ser Leu Asp Arg Tyr Ile Lys Ile Asn Arg Ser Ile
145                 150                 155                 160

Gln Gln Arg Lys Ala Ile Thr Thr Lys Gln Ser Ile Tyr Val Cys Cys
                165                 170                 175

Ile Val Trp Met Leu Ala Leu Gly Gly Phe Leu Thr Met Ile Ile Leu
            180                 185                 190

Thr Leu Lys Lys Gly Gly His Asn Ser Thr Met Cys Phe His Tyr Arg
        195                 200                 205

Asp Lys His Asn Ala Lys Gly Glu Ala Ile Phe Asn Phe Ile Leu Val
    210                 215                 220

Val Met Phe Trp Leu Ile Phe Leu Leu Ile Ile Leu Ser Tyr Ile Lys
225                 230                 235                 240

Ile Gly Lys Asn Leu Leu Arg Ile Ser Lys Arg Arg Ser Lys Phe Pro
                245                 250                 255

Asn Ser Gly Lys Tyr Ala Thr Thr Ala Arg Asn Ser Phe Ile Val Leu
            260                 265                 270

Ile Ile Phe Thr Ile Cys Phe Val Pro Tyr His Ala Phe Arg Phe Ile
        275                 280                 285

Tyr Ile Ser Ser Gln Leu Asn Val Ser Ser Cys Tyr Trp Lys Glu Ile
    290                 295                 300

Val His Lys Thr Asn Glu Ile Met Leu Val Leu Ser Ser Phe Asn Ser
305                 310                 315                 320

Cys Leu Asp Pro Val Met Tyr Phe Leu Met Ser Ser Asn Ile Arg Lys
                325                 330                 335

Ile Met Cys Gln Leu Leu Phe Arg Arg Phe Gln Gly Glu Pro Ser Arg
            340                 345                 350

Ser Glu Ser Thr Ser Glu Phe Lys Pro Gly Tyr Ser Leu His Asp Thr
        355                 360                 365

Ser Val Ala Val Lys Ile Gln Ser Ser Ser Lys Ser Thr
    370                 375                 380
```

<210> SEQ ID NO 25
<211> LENGTH: 349
<212> TYPE: PRT
<213> ORGANISM: Homo sapiens

<400> SEQUENCE: 25

```
Met Arg Ser His Thr Ile Thr Met Thr Thr Thr Ser Val Ser Ser Trp
1               5                   10                  15

Pro Tyr Ser Ser His Arg Met Arg Phe Ile Thr Asn His Ser Asp Gln
```

```
            20                  25                  30

Pro Pro Gln Asn Phe Ser Ala Thr Pro Asn Val Thr Thr Cys Pro Met
        35                  40                  45

Asp Glu Lys Leu Leu Ser Thr Val Leu Thr Thr Ser Tyr Ser Val Ile
    50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Ala Ile Ala Asp Leu Leu Leu Ile Phe Cys Leu Pro Phe Arg Ile Met
            100                 105                 110

Tyr His Ile Asn Gln Asn Lys Trp Thr Leu Gly Val Ile Leu Cys Lys
        115                 120                 125

Val Val Gly Thr Leu Phe Tyr Met Lys Gln Ser Ile Tyr Val Cys Cys
    130                 135                 140

Ile Val Trp Met Leu Ala Leu Gly Gly Phe Leu Thr Met Ile Ile Leu
145                 150                 155                 160

Thr Leu Lys Lys Gly Gly His Asn Ser Thr Met Cys Phe His Tyr Arg
                165                 170                 175

Asp Lys His Asn Ala Lys Gly Glu Ala Ile Phe Asn Phe Ile Leu Val
            180                 185                 190

Val Met Phe Trp Leu Ile Phe Leu Leu Ile Ile Leu Ser Tyr Ile Lys
        195                 200                 205

Ile Gly Lys Asn Leu Leu Arg Ile Ser Lys Arg Arg Ser Lys Phe Pro
    210                 215                 220

Asn Ser Gly Lys Tyr Ala Thr Thr Ala Arg Asn Ser Phe Ile Val Leu
225                 230                 235                 240

Ile Ile Phe Thr Ile Cys Phe Val Pro Tyr His Ala Phe Arg Phe Ile
                245                 250                 255

Tyr Ile Ser Ser Gln Leu Asn Val Ser Ser Cys Tyr Trp Lys Glu Ile
            260                 265                 270

Val His Lys Thr Asn Glu Ile Met Leu Val Leu Ser Ser Phe Asn Ser
        275                 280                 285

Cys Leu Asp Pro Val Met Tyr Phe Leu Met Ser Ser Asn Ile Arg Lys
    290                 295                 300

Ile Met Cys Gln Leu Leu Phe Arg Arg Phe Gln Gly Glu Pro Ser Arg
305                 310                 315                 320

Ser Glu Ser Thr Ser Glu Phe Lys Pro Gly Tyr Ser Leu His Asp Thr
                325                 330                 335

Ser Val Ala Val Lys Ile Gln Ser Ser Ser Lys Ser Thr
            340                 345
```

<210> SEQ ID NO 26
<211> LENGTH: 334
<212> TYPE: PRT
<213> ORGANISM: Homo sapiens

<400> SEQUENCE: 26

```
Met Asp Glu Lys Leu Leu Ser Thr Val Leu Thr Thr Ser Tyr Ser Val
1               5                   10                  15

Ile Phe Ile Val Gly Leu Val Gly Asn Ile Ile Ala Leu Tyr Val Phe
            20                  25                  30

Leu Gly Ile His Arg Lys Arg Asn Ser Ile Gln Ile Tyr Leu Leu Asn
        35                  40                  45
```

-continued

```
Val Ala Ile Ala Asp Leu Leu Leu Ile Phe Cys Leu Pro Phe Arg Ile
    50                  55                  60

Met Tyr His Ile Asn Gln Asn Lys Trp Thr Leu Gly Val Ile Leu Cys
65                  70                  75                  80

Lys Val Val Gly Thr Leu Phe Tyr Met Asn Met Tyr Ile Ser Ile Ile
                85                  90                  95

Leu Leu Gly Phe Ile Ser Leu Asp Arg Tyr Ile Lys Ile Asn Arg Ser
            100                 105                 110

Ile Gln Gln Arg Lys Ala Ile Thr Thr Lys Gln Ser Ile Tyr Val Cys
        115                 120                 125

Cys Ile Val Trp Met Leu Ala Leu Gly Gly Phe Leu Thr Met Ile Ile
    130                 135                 140

Leu Thr Leu Lys Lys Gly Gly His Asn Ser Thr Met Cys Phe His Tyr
145                 150                 155                 160

Arg Asp Lys His Asn Ala Lys Gly Glu Ala Ile Phe Asn Phe Ile Leu
                165                 170                 175

Val Val Met Phe Trp Leu Ile Phe Leu Leu Ile Ile Leu Ser Tyr Ile
            180                 185                 190

Lys Ile Gly Lys Asn Leu Leu Arg Ile Ser Lys Arg Arg Ser Lys Phe
        195                 200                 205

Pro Asn Ser Gly Lys Tyr Ala Thr Thr Ala Arg Asn Ser Phe Ile Val
    210                 215                 220

Leu Ile Ile Phe Thr Ile Cys Phe Val Pro Tyr His Ala Phe Arg Phe
225                 230                 235                 240

Ile Tyr Ile Ser Ser Gln Leu Asn Val Ser Ser Cys Tyr Trp Lys Glu
                245                 250                 255

Ile Val His Lys Thr Asn Glu Ile Met Leu Val Leu Ser Ser Phe Asn
            260                 265                 270

Ser Cys Leu Asp Pro Val Met Tyr Phe Leu Met Ser Ser Asn Ile Arg
        275                 280                 285

Lys Ile Met Cys Gln Leu Leu Phe Arg Arg Phe Gln Gly Glu Pro Ser
    290                 295                 300

Arg Ser Glu Ser Thr Ser Glu Phe Lys Pro Gly Tyr Ser Leu His Asp
305                 310                 315                 320

Thr Ser Val Ala Val Lys Ile Gln Ser Ser Ser Lys Ser Thr
                325                 330


<210> SEQ ID NO 27
<211> LENGTH: 330
<212> TYPE: PRT
<213> ORGANISM: Homo sapiens

<400> SEQUENCE: 27

Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95
```

-continued

```
Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330


<210> SEQ ID NO 28
<211> LENGTH: 400
<212> TYPE: PRT
<213> ORGANISM: Homo sapiens

<400> SEQUENCE: 28

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
```

```
    130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400


<210> SEQ ID NO 29
<211> LENGTH: 1117
<212> TYPE: PRT
<213> ORGANISM: Homo sapiens

<400> SEQUENCE: 29

Met Glu Ile Leu Trp Lys Thr Leu Thr Trp Ile Leu Ser Leu Ile Met
1               5                   10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110
```

-continued

```
Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Ala Lys Leu Tyr Arg Asp
        275                 280                 285

Ser Ser Leu Gly Asn Val Val Asn Ile Ile Val Ala Arg Leu Ile Val
    290                 295                 300

Leu Thr Glu Asp Gln Pro Asn Leu Glu Ile Asn His His Ala Asp Lys
305                 310                 315                 320

Ser Leu Asp Ser Phe Cys Lys Trp Gln Lys Ser Ile Leu Ser His Gln
                325                 330                 335

Ser Asp Gly Asn Thr Ile Pro Glu Asn Gly Ile Ala His His Asp Asn
            340                 345                 350

Ala Val Leu Ile Thr Arg Tyr Asp Ile Cys Thr Tyr Lys Asn Lys Pro
        355                 360                 365

Cys Gly Thr Leu Gly Leu Ala Ser Val Ala Gly Met Cys Glu Pro Glu
    370                 375                 380

Arg Ser Cys Ser Ile Asn Glu Asp Ile Gly Leu Gly Ser Ala Phe Thr
385                 390                 395                 400

Ile Ala His Glu Ile Gly His Asn Phe Gly Met Asn His Asp Gly Ile
                405                 410                 415

Gly Asn Ser Cys Gly Thr Lys Gly His Glu Ala Ala Lys Leu Met Ala
            420                 425                 430

Ala His Ile Thr Ala Asn Thr Asn Pro Phe Ser Trp Ser Ala Cys Ser
        435                 440                 445

Arg Asp Tyr Ile Thr Ser Phe Leu Asp Ser Gly Arg Gly Thr Cys Leu
    450                 455                 460

Asp Asn Glu Pro Pro Lys Arg Asp Phe Leu Tyr Pro Ala Val Ala Pro
465                 470                 475                 480

Gly Gln Val Tyr Asp Ala Asp Glu Gln Cys Arg Phe Gln Tyr Gly Ala
                485                 490                 495

Thr Ser Arg Gln Cys Lys Tyr Gly Glu Val Cys Arg Glu Leu Trp Cys
            500                 505                 510

Leu Ser Lys Ser Asn Arg Cys Val Thr Asn Ser Ile Pro Ala Ala Glu
        515                 520                 525

Gly Thr Leu Cys Gln Thr Gly Asn Ile Glu Lys Gly Trp Cys Tyr Gln
```

-continued

```
    530                 535                 540

Gly Asp Cys Val Pro Phe Gly Thr Trp Pro Gln Ser Ile Asp Gly Gly
545                 550                 555                 560

Trp Gly Pro Trp Ser Leu Trp Gly Glu Cys Ser Arg Thr Cys Gly Gly
                565                 570                 575

Gly Val Ser Ser Ser Leu Arg His Cys Asp Ser Pro Ala Pro Ser Gly
            580                 585                 590

Gly Gly Lys Tyr Cys Leu Gly Glu Arg Lys Arg Tyr Arg Ser Cys Asn
        595                 600                 605

Thr Asp Pro Cys Pro Leu Gly Ser Arg Asp Phe Arg Glu Lys Gln Cys
    610                 615                 620

Ala Asp Phe Asp Asn Met Pro Phe Arg Gly Lys Tyr Tyr Asn Trp Lys
625                 630                 635                 640

Pro Tyr Thr Gly Gly Gly Val Lys Pro Cys Ala Leu Asn Cys Leu Ala
                645                 650                 655

Glu Gly Tyr Asn Phe Tyr Thr Glu Arg Ala Pro Ala Val Ile Asp Gly
            660                 665                 670

Thr Gln Cys Asn Ala Asp Ser Leu Asp Ile Cys Ile Asn Gly Glu Cys
        675                 680                 685

Lys His Val Gly Cys Asp Asn Ile Leu Gly Ser Asp Ala Arg Glu Asp
    690                 695                 700

Arg Cys Arg Val Cys Gly Gly Asp Gly Ser Thr Cys Asp Ala Ile Glu
705                 710                 715                 720

Gly Phe Phe Asn Asp Ser Leu Pro Arg Gly Gly Tyr Met Glu Val Val
                725                 730                 735

Gln Ile Pro Arg Gly Ser Val His Ile Glu Val Arg Glu Val Ala Met
            740                 745                 750

Ser Lys Asn Tyr Ile Ala Leu Lys Ser Glu Gly Asp Asp Tyr Tyr Ile
        755                 760                 765

Asn Gly Ala Trp Thr Ile Asp Trp Pro Arg Lys Phe Asp Val Ala Gly
    770                 775                 780

Thr Ala Phe His Tyr Lys Arg Pro Thr Asp Glu Pro Glu Ser Leu Glu
785                 790                 795                 800

Ala Leu Gly Pro Thr Ser Glu Asn Leu Ile Val Met Val Leu Leu Gln
                805                 810                 815

Glu Gln Asn Leu Gly Ile Arg Tyr Lys Phe Asn Val Pro Ile Thr Arg
            820                 825                 830

Thr Gly Ser Gly Asp Asn Glu Val Gly Phe Thr Trp Asn His Gln Pro
        835                 840                 845

Trp Ser Glu Cys Ser Ala Thr Cys Ala Gly Gly Val Gln Arg Gln Glu
    850                 855                 860

Val Val Cys Lys Arg Leu Asp Asp Asn Ser Ile Val Gln Asn Asn Tyr
865                 870                 875                 880

Cys Asp Pro Asp Ser Lys Pro Pro Glu Asn Gln Arg Ala Cys Asn Thr
                885                 890                 895

Glu Pro Cys Pro Pro Glu Trp Phe Ile Gly Asp Trp Leu Glu Cys Ser
            900                 905                 910

Lys Thr Cys Asp Gly Gly Met Arg Thr Arg Ala Val Leu Cys Ile Arg
        915                 920                 925

Lys Ile Gly Pro Ser Glu Glu Thr Leu Asp Tyr Ser Gly Cys Leu
    930                 935                 940

Thr His Arg Pro Val Glu Lys Glu Pro Cys Asn Asn Gln Ser Cys Pro
945                 950                 955                 960
```

```
Pro Gln Trp Val Ala Leu Asp Trp Ser Glu Cys Thr Pro Lys Cys Gly
                965                 970                 975

Pro Gly Phe Lys His Arg Ile Val Leu Cys Lys Ser Ser Asp Leu Ser
            980                 985                 990

Lys Thr Phe Pro Ala Ala Gln Cys  Pro Glu Glu Ser Lys  Pro Pro Val
        995                 1000                1005

Arg Ile  Arg Cys Ser Leu Gly  Arg Cys Pro Pro Pro  Arg Trp Val
    1010                 1015                1020

Thr Gly  Asp Trp Gly Gln Cys  Ser Ala Gln Cys Gly  Leu Gly Gln
    1025                 1030                1035

Gln Met  Arg Thr Val Gln Cys  Leu Ser Tyr Thr Gly  Gln Ala Ser
    1040                 1045                1050

Ser Asp  Cys Leu Glu Thr Val  Arg Pro Pro Ser Met  Gln Gln Cys
    1055                 1060                1065

Glu Ser  Lys Cys Asp Ser Thr  Pro Ile Ser Asn Thr  Glu Glu Cys
    1070                 1075                1080

Lys Asp  Val Asn Lys Val Ala  Tyr Cys Pro Leu Val  Leu Lys Phe
    1085                 1090                1095

Lys Phe  Cys Ser Arg Ala Tyr  Phe Arg Gln Met Cys  Cys Lys Thr
    1100                 1105                1110

Cys Gln  Gly His
    1115


<210> SEQ ID NO 30
<211> LENGTH: 427
<212> TYPE: PRT
<213> ORGANISM: Homo sapiens

<400> SEQUENCE: 30

Met Gly Gly Asp Leu Val Leu Gly Leu Gly Ala Leu Arg Arg Arg Lys
1               5                   10                  15

Arg Leu Leu Glu Gln Glu Lys Ser Leu Ala Gly Trp Ala Leu Val Leu
            20                  25                  30

Ala Gly Thr Gly Ile Gly Leu Met Val Leu His Ala Glu Met Leu Trp
        35                  40                  45

Phe Gly Gly Cys Ser Trp Ala Leu Tyr Leu Phe Leu Val Lys Cys Thr
    50                  55                  60

Ile Ser Ile Ser Thr Phe Leu Leu Leu Cys Leu Ile Val Ala Phe His
65                  70                  75                  80

Ala Lys Glu Val Gln Leu Phe Met Thr Asp Asn Gly Leu Arg Asp Trp
                85                  90                  95

Arg Val Ala Leu Thr Gly Arg Gln Ala Ala Gln Ile Val Leu Glu Leu
            100                 105                 110

Val Val Cys Gly Leu His Pro Ala Pro Val Arg Gly Pro Pro Cys Val
        115                 120                 125

Gln Asp Leu Gly Ala Pro Leu Thr Ser Pro Gln Pro Trp Pro Gly Phe
    130                 135                 140

Leu Gly Gln Gly Glu Ala Leu Leu Ser Leu Ala Met Leu Leu Arg Leu
145                 150                 155                 160

Tyr Leu Val Pro Arg Ala Val Leu Leu Arg Ser Gly Val Leu Leu Asn
                165                 170                 175

Ala Ser Tyr Arg Ser Ile Gly Ala Leu Asn Gln Val Arg Phe Arg His
            180                 185                 190

Trp Phe Val Ala Lys Leu Tyr Met Asn Thr His Pro Gly Arg Leu Leu
```

```
        195                 200                 205

Leu Gly Leu Thr Leu Gly Leu Trp Leu Thr Thr Ala Trp Val Leu Ser
    210                 215                 220

Val Ala Glu Arg Gln Ala Val Asn Ala Thr Gly His Leu Ser Asp Thr
225                 230                 235                 240

Leu Trp Leu Ile Pro Ile Thr Phe Leu Thr Ile Gly Tyr Gly Asp Val
                245                 250                 255

Val Pro Gly Thr Met Trp Gly Lys Ile Val Cys Leu Cys Thr Gly Val
            260                 265                 270

Met Gly Val Cys Cys Thr Ala Leu Leu Val Ala Val Val Ala Arg Lys
        275                 280                 285

Leu Glu Phe Asn Lys Ala Glu Lys His Val His Asn Phe Met Met Asp
    290                 295                 300

Ile Gln Tyr Thr Lys Glu Met Lys Glu Ser Ala Ala Arg Val Leu Gln
305                 310                 315                 320

Glu Ala Trp Met Phe Tyr Lys His Thr Arg Arg Lys Glu Ser His Ala
                325                 330                 335

Ala Arg Arg His Gln Arg Lys Leu Leu Ala Ala Ile Asn Ala Phe Arg
            340                 345                 350

Gln Val Arg Leu Lys His Arg Lys Leu Arg Glu Gln Val Asn Ser Met
        355                 360                 365

Val Asp Ile Ser Lys Met His Met Ile Leu Tyr Asp Leu Gln Gln Asn
    370                 375                 380

Leu Ser Ser Ser His Arg Ala Leu Glu Lys Gln Ile Asp Thr Leu Ala
385                 390                 395                 400

Gly Lys Leu Asp Ala Leu Thr Glu Leu Leu Ser Thr Ala Leu Gly Pro
                405                 410                 415

Arg Gln Leu Pro Glu Pro Ser Gln Gln Ser Lys
            420                 425


<210> SEQ ID NO 31
<211> LENGTH: 814
<212> TYPE: PRT
<213> ORGANISM: Homo sapiens

<400> SEQUENCE: 31

Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140
```

-continued

```
Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
```

```
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ser Gln Gly Pro Ala Lys Pro Pro Pro
        755                 760                 765

Pro Arg Lys Pro Leu Pro Ala Asp Pro Gln Gly Arg Cys Pro Ser Gly
    770                 775                 780

Asp Leu Pro Gly Pro Gly Ala Gly Ile Pro Pro Leu Val Val Pro Ser
785                 790                 795                 800

Arg Pro Ala Pro Pro Pro Pro Thr Val Ser Ser Leu Tyr Leu
                805                 810


<210> SEQ ID NO 32
<211> LENGTH: 772
<212> TYPE: PRT
<213> ORGANISM: Homo sapiens

<400> SEQUENCE: 32

Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125
```

-continued

```
Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
```

545 550 555 560

Gly Arg Asn Pro Ser Gly Ser Tyr Val Ser Cys Thr Pro Arg Asp Ala
565 570 575

Ile Cys Gly Gln Leu Gln Cys Gln Thr Gly Arg Thr Gln Pro Leu Leu
580 585 590

Gly Ser Ile Arg Asp Leu Leu Trp Glu Thr Ile Asp Val Asn Gly Thr
595 600 605

Glu Leu Asn Cys Ser Trp Val His Leu Asp Leu Gly Ser Asp Val Ala
610 615 620

Gln Pro Leu Leu Thr Leu Pro Gly Thr Ala Cys Gly Pro Gly Leu Val
625 630 635 640

Cys Ile Asp His Arg Cys Gln Arg Val Asp Leu Leu Gly Ala Gln Glu
645 650 655

Cys Arg Ser Lys Cys His Gly His Gly Val Cys Asp Ser Asn Arg His
660 665 670

Cys Tyr Cys Glu Glu Gly Trp Ala Pro Pro Asp Cys Thr Thr Gln Leu
675 680 685

Lys Ala Thr Ser Ser Leu Thr Thr Gly Leu Leu Leu Ser Leu Leu Val
690 695 700

Leu Leu Val Leu Val Met Leu Gly Ala Ser Tyr Trp Tyr Arg Ala Arg
705 710 715 720

Leu His Gln Arg Leu Cys Gln Leu Lys Gly Pro Thr Cys Gln Tyr Ser
725 730 735

Leu Arg Gly Gln Pro Ser Pro His Pro Gln Gly Ser His Cys Leu Pro
740 745 750

Thr Pro Arg Ala Gly Ala His Arg Val Thr Cys Pro Ala Gln Gly Leu
755 760 765

Glu Ser Arg Pro
770

<210> SEQ ID NO 33
<211> LENGTH: 839
<212> TYPE: PRT
<213> ORGANISM: Homo sapiens

<400> SEQUENCE: 33

Met Arg Leu Ala Leu Leu Trp Ala Leu Gly Leu Leu Gly Ala Gly Ser
1 5 10 15

Pro Leu Pro Ser Trp Pro Leu Pro Asn Ile Gly Gly Thr Glu Glu Gln
20 25 30

Gln Ala Glu Ser Glu Lys Ala Pro Arg Glu Pro Leu Glu Pro Gln Val
35 40 45

Leu Gln Asp Asp Leu Pro Ile Ser Leu Lys Lys Val Leu Gln Thr Ser
50 55 60

Leu Pro Glu Pro Leu Arg Ile Lys Leu Glu Leu Asp Gly Asp Ser His
65 70 75 80

Ile Leu Glu Leu Leu Gln Asn Arg Glu Leu Val Pro Gly Arg Pro Thr
85 90 95

Leu Val Trp Tyr Gln Pro Asp Gly Thr Arg Val Val Ser Glu Gly His
100 105 110

Thr Leu Glu Asn Cys Cys Tyr Gln Gly Arg Val Arg Gly Tyr Ala Gly
115 120 125

Ser Trp Val Ser Ile Cys Thr Cys Ser Gly Leu Arg Gly Leu Val Val
130 135 140

-continued

```
Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
```

-continued

```
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Gln Ala Ser Ala Leu Ser Phe Pro Ala
        755                 760                 765

Pro Pro Ser Arg Pro Leu Pro Pro Asp Pro Val Ser Lys Arg Leu Gln
    770                 775                 780

Ser Gln Gly Pro Ala Lys Pro Pro Pro Pro Arg Lys Pro Leu Pro Ala
785                 790                 795                 800

Asp Pro Gln Gly Arg Cys Pro Ser Gly Asp Leu Pro Gly Pro Gly Ala
                805                 810                 815

Gly Ile Pro Pro Leu Val Val Pro Ser Arg Pro Ala Pro Pro Pro Pro
            820                 825                 830

Thr Val Ser Ser Leu Tyr Leu
        835


<210> SEQ ID NO 34
<211> LENGTH: 838
<212> TYPE: PRT
<213> ORGANISM: Homo sapiens

<400> SEQUENCE: 34

Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95
```

-continued

```
Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
```

```
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ala Glu Leu Ala Asp Arg Pro Asn Pro
        755                 760                 765

Pro Thr Arg Pro Leu Pro Ala Asp Pro Val Val Arg Ser Pro Lys Ser
    770                 775                 780

Gln Gly Pro Ala Lys Pro Pro Pro Pro Arg Lys Pro Leu Pro Ala Asp
785                 790                 795                 800

Pro Gln Gly Arg Cys Pro Ser Gly Asp Leu Pro Gly Pro Gly Ala Gly
                805                 810                 815

Ile Pro Pro Leu Val Val Pro Ser Arg Pro Ala Pro Pro Pro Pro Thr
            820                 825                 830

Val Ser Ser Leu Tyr Leu
        835


<210> SEQ ID NO 35
<211> LENGTH: 862
<212> TYPE: PRT
<213> ORGANISM: Homo sapiens

<400> SEQUENCE: 35

Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45
```

-continued

```
Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
```

```
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ala Ser Ala Leu Ser Phe Pro Ala Pro
        755                 760                 765

Pro Ser Arg Pro Leu Pro Pro Asp Pro Val Ser Lys Arg Leu Gln Ala
    770                 775                 780

Glu Leu Ala Asp Arg Pro Asn Pro Pro Thr Arg Pro Leu Pro Ala Asp
785                 790                 795                 800

Pro Val Val Arg Ser Pro Lys Ser Gln Gly Pro Ala Lys Pro Pro Pro
                805                 810                 815

Pro Arg Lys Pro Leu Pro Ala Asp Pro Gln Gly Arg Cys Pro Ser Gly
            820                 825                 830

Asp Leu Pro Gly Pro Gly Ala Gly Ile Pro Pro Leu Val Val Pro Ser
        835                 840                 845

Arg Pro Ala Pro Pro Pro Pro Thr Val Ser Ser Leu Tyr Leu
    850                 855                 860
```

<210> SEQ ID NO 36
<211> LENGTH: 863
<212> TYPE: PRT
<213> ORGANISM: Homo sapiens -continued

<400> SEQUENCE: 36

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Lys Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
```

-continued

```
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Gln Ala Ser Ala Leu Ser Phe Pro Ala
        755                 760                 765

Pro Pro Ser Arg Pro Leu Pro Pro Asp Pro Val Ser Lys Arg Leu Gln
    770                 775                 780

Ala Glu Leu Ala Asp Arg Pro Asn Pro Pro Thr Arg Pro Leu Pro Ala
785                 790                 795                 800

Asp Pro Val Val Arg Ser Pro Lys Ser Gln Gly Pro Ala Lys Pro Pro
                805                 810                 815

Pro Pro Arg Lys Pro Leu Pro Ala Asp Pro Gln Gly Arg Cys Pro Ser
            820                 825                 830
```

Gly Asp Leu Pro Gly Pro Gly Ala Gly Ile Pro Pro Leu Val Val Pro
835 840 845

Ser Arg Pro Ala Pro Pro Pro Pro Thr Val Ser Ser Leu Tyr Leu
850 855 860

<210> SEQ ID NO 37
<211> LENGTH: 833
<212> TYPE: PRT
<213> ORGANISM: Homo sapiens

<400> SEQUENCE: 37

Met Asp Val Val Asp Pro Asp Ile Phe Asn Arg Asp Pro Arg Asp His
1 5 10 15

Tyr Asp Leu Leu Gln Arg Leu Gly Gly Gly Thr Tyr Gly Glu Val Phe
20 25 30

Lys Ala Arg Asp Lys Val Ser Gly Asp Leu Val Ala Leu Lys Met Val
35 40 45

Lys Met Glu Pro Asp Asp Asp Val Ser Thr Leu Gln Lys Glu Ile Leu
50 55 60

Ile Leu Lys Thr Cys Arg His Ala Asn Ile Val Ala Tyr His Gly Ser
65 70 75 80

Tyr Leu Trp Leu Gln Lys Leu Trp Ile Cys Met Glu Phe Cys Gly Ala
85 90 95

Gly Ser Leu Gln Asp Ile Tyr Gln Val Thr Gly Ser Leu Ser Glu Leu
100 105 110

Gln Ile Ser Tyr Val Cys Arg Glu Val Leu Gln Gly Leu Ala Tyr Leu
115 120 125

His Ser Gln Lys Lys Ile His Arg Asp Ile Lys Gly Ala Asn Ile Leu
130 135 140

Ile Asn Asp Ala Gly Glu Val Arg Leu Ala Asp Phe Gly Ile Ser Ala
145 150 155 160

Gln Ile Gly Ala Thr Leu Ala Arg Arg Leu Ser Phe Ile Gly Thr Pro
165 170 175

Tyr Trp Met Ala Pro Glu Val Ala Ala Val Ala Leu Lys Gly Gly Tyr
180 185 190

Asn Glu Leu Cys Asp Ile Trp Ser Leu Gly Ile Thr Ala Ile Glu Leu
195 200 205

Ala Glu Leu Gln Pro Pro Leu Phe Asp Val His Pro Leu Arg Val Leu
210 215 220

Phe Leu Met Thr Lys Ser Gly Tyr Gln Pro Pro Arg Leu Lys Glu Lys
225 230 235 240

Gly Lys Trp Ser Ala Ala Phe His Asn Phe Ile Lys Val Thr Leu Thr
245 250 255

Lys Ser Pro Lys Lys Arg Pro Ser Ala Thr Lys Met Leu Ser His Gln
260 265 270

Leu Val Ser Gln Pro Gly Leu Asn Arg Gly Leu Ile Leu Asp Leu Leu
275 280 285

Asp Lys Leu Lys Asn Pro Gly Lys Gly Pro Ser Ile Gly Asp Ile Glu
290 295 300

Asp Glu Glu Pro Glu Leu Pro Pro Ala Ile Pro Arg Arg Ile Arg Ser
305 310 315 320

Thr His Arg Ser Ser Ser Leu Gly Ile Pro Asp Ala Asp Cys Cys Arg
325 330 335

Arg His Met Glu Phe Arg Lys Leu Arg Gly Met Glu Thr Arg Pro Pro

```
            340                 345                 350

Ala Asn Thr Ala Arg Leu Gln Pro Pro Arg Asp Leu Arg Ser Ser Ser
        355                 360                 365

Pro Arg Lys Gln Leu Ser Glu Ser Ser Asp Asp Asp Tyr Asp Asp Val
    370                 375                 380

Asp Ile Pro Thr Pro Ala Glu Asp Thr Pro Pro Pro Leu Pro Pro Lys
385                 390                 395                 400

Pro Lys Phe Arg Ser Pro Ser Asp Glu Gly Pro Gly Ser Met Gly Asp
                405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Pro Ser Thr Ser Ser Pro
        435                 440                 445

His Leu Thr Ala His Ser Glu Pro Ser Leu Trp Asn Pro Pro Ser Arg
    450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
            500                 505                 510

His Leu Leu Leu Gly Ala Glu Glu Gly Ile Phe Ile Leu Asn Arg Asn
        515                 520                 525

Asp Gln Glu Ala Thr Leu Glu Met Leu Phe Pro Ser Arg Thr Thr Trp
    530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
        595                 600                 605

Ala Cys Cys Val Ala Glu Gly Ala Ser Ser Gly Gly Pro Phe Leu Cys
    610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
                645                 650                 655

Leu Ser Val Phe Ala Leu Leu Thr Gly Pro Gly Ser Glu Leu Pro Ala
            660                 665                 670

Val Cys Ile Gly Val Ser Pro Gly Arg Pro Gly Lys Ser Val Leu Phe
        675                 680                 685

His Thr Val Arg Phe Gly Ala Leu Ser Cys Trp Leu Gly Glu Met Ser
    690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                725                 730                 735

Ser Pro Val Arg Gly Leu Arg Thr Pro Glu Ile Pro Met Thr Glu Ala
            740                 745                 750

Val Glu Ala Val Ala Met Val Gly Gly Gln Leu Gln Ala Phe Trp Lys
        755                 760                 765
```

His Gly Val Gln Val Trp Ala Leu Gly Ser Asp Gln Leu Leu Gln Glu
770 775 780

Leu Arg Asp Pro Thr Leu Thr Phe Arg Leu Leu Gly Ser Pro Arg Leu
785 790 795 800

Glu Cys Ser Gly Thr Ile Ser Pro His Cys Asn Leu Leu Leu Pro Gly
805 810 815

Ser Ser Asn Ser Pro Ala Ser Ala Ser Arg Val Ala Gly Ile Thr Gly
820 825 830

Leu

<210> SEQ ID NO 38
<211> LENGTH: 323
<212> TYPE: PRT
<213> ORGANISM: Homo sapiens

<400> SEQUENCE: 38

Met Asn Ala Ser Cys Cys Leu Pro Ser Val Gln Pro Thr Leu Pro Asn
1 5 10 15

Gly Ser Glu His Leu Gln Ala Pro Phe Phe Ser Asn Gln Ser Ser Ser
20 25 30

Ala Phe Cys Glu Gln Val Phe Ile Lys Pro Glu Val Phe Leu Ser Leu
35 40 45

Gly Ile Val Ser Leu Leu Glu Asn Ile Leu Val Ile Leu Ala Val Val
50 55 60

Arg Asn Gly Asn Leu His Ser Pro Met Tyr Phe Phe Leu Cys Ser Leu
65 70 75 80

Ala Val Ala Asp Met Leu Val Ser Val Ser Asn Ala Leu Glu Thr Ile
85 90 95

Met Ile Ala Ile Val His Ser Asp Tyr Leu Thr Phe Glu Asp Gln Phe
100 105 110

Ile Gln His Met Asp Asn Ile Phe Asp Ser Met Ile Cys Ile Ser Leu
115 120 125

Val Ala Ser Ile Cys Asn Leu Leu Ala Ile Ala Val Asp Arg Tyr Val
130 135 140

Thr Ile Phe Tyr Ala Leu Arg Tyr His Ser Ile Met Thr Val Arg Lys
145 150 155 160

Ala Leu Thr Leu Ile Val Ala Ile Trp Val Cys Cys Gly Val Cys Gly
165 170 175

Val Val Phe Ile Val Tyr Ser Glu Ser Lys Met Val Ile Val Cys Leu
180 185 190

Ile Thr Met Phe Phe Ala Met Met Leu Leu Met Gly Thr Leu Tyr Val
195 200 205

His Met Phe Leu Phe Ala Arg Leu His Val Lys Arg Ile Ala Ala Leu
210 215 220

Pro Pro Ala Asp Gly Val Ala Pro Gln Gln His Ser Cys Met Lys Gly
225 230 235 240

Ala Val Thr Ile Thr Ile Leu Leu Gly Val Phe Ile Phe Cys Trp Ala
245 250 255

Pro Phe Phe Leu His Leu Val Leu Ile Ile Thr Cys Pro Thr Asn Pro
260 265 270

Tyr Cys Ile Cys Tyr Thr Ala His Phe Asn Thr Tyr Leu Val Leu Ile
275 280 285

Met Cys Asn Ser Val Ile Asp Pro Leu Ile Tyr Ala Phe Arg Ser Leu
290 295 300

Glu Leu Arg Asn Thr Phe Arg Glu Ile Leu Cys Gly Cys Asn Gly Met
305 310 315 320

Asn Leu Gly

<210> SEQ ID NO 39
<211> LENGTH: 1037
<212> TYPE: PRT
<213> ORGANISM: Homo sapiens

<400> SEQUENCE: 39

Met Arg Gly Ser Gly Pro Arg Gly Ala Gly His Arg Arg Pro Pro Ser
1 5 10 15

Gly Gly Gly Asp Thr Pro Ile Thr Pro Ala Ser Leu Ala Gly Cys Tyr
20 25 30

Ser Ala Pro Arg Arg Ala Pro Leu Trp Thr Cys Leu Leu Leu Cys Ala
35 40 45

Ala Leu Arg Thr Leu Leu Ala Ser Pro Ser Asn Glu Val Asn Leu Leu
50 55 60

Asp Ser Arg Thr Val Met Gly Asp Leu Gly Trp Ile Ala Phe Pro Lys
65 70 75 80

Asn Gly Trp Glu Glu Ile Gly Glu Val Asp Glu Asn Tyr Ala Pro Ile
85 90 95

His Thr Tyr Gln Val Cys Lys Val Met Glu Gln Asn Gln Asn Asn Trp
100 105 110

Leu Leu Thr Ser Trp Ile Ser Asn Glu Gly Ala Ser Arg Ile Phe Ile
115 120 125

Glu Leu Lys Phe Thr Leu Arg Asp Cys Asn Ser Leu Pro Gly Gly Leu
130 135 140

Gly Thr Cys Lys Glu Thr Phe Asn Met Tyr Tyr Phe Glu Ser Asp Asp
145 150 155 160

Gln Asn Gly Arg Asn Ile Lys Glu Asn Gln Tyr Ile Lys Ile Asp Thr
165 170 175

Ile Ala Ala Asp Glu Ser Phe Thr Glu Leu Asp Leu Gly Asp Arg Val
180 185 190

Met Lys Leu Asn Thr Glu Val Arg Asp Val Gly Pro Leu Ser Lys Lys
195 200 205

Gly Phe Tyr Leu Ala Phe Gln Asp Val Gly Ala Cys Ile Ala Leu Val
210 215 220

Ser Val Arg Val Tyr Tyr Lys Lys Cys Pro Ser Val Val Arg His Leu
225 230 235 240

Ala Val Phe Pro Asp Thr Ile Thr Gly Ala Asp Ser Ser Gln Leu Leu
245 250 255

Glu Val Ser Gly Ser Cys Val Asn His Ser Val Thr Asp Glu Pro Pro
260 265 270

Lys Met His Cys Ser Ala Glu Gly Glu Trp Leu Val Pro Ile Gly Lys
275 280 285

Cys Met Cys Lys Ala Gly Tyr Glu Glu Lys Asn Gly Thr Cys Gln Val
290 295 300

Cys Arg Pro Gly Phe Phe Lys Ala Ser Pro His Ile Gln Ser Cys Gly
305 310 315 320

Lys Cys Pro Pro His Ser Tyr Thr His Glu Glu Ala Ser Thr Ser Cys
325 330 335

Val Cys Glu Lys Asp Tyr Phe Arg Arg Glu Ser Asp Pro Pro Thr Met
340 345 350

```
Ala Cys Thr Arg Pro Pro Ser Ala Pro Arg Asn Ala Ile Ser Asn Val
        355                 360                 365

Asn Glu Thr Ser Val Phe Leu Glu Trp Ile Pro Pro Ala Asp Thr Gly
    370                 375                 380

Gly Arg Lys Asp Val Ser Tyr Tyr Ile Ala Cys Lys Lys Cys Asn Ser
385                 390                 395                 400

His Ala Gly Val Cys Glu Glu Cys Gly Gly His Val Arg Tyr Leu Pro
                405                 410                 415

Arg Gln Ser Gly Leu Lys Asn Thr Ser Val Met Met Val Asp Leu Leu
            420                 425                 430

Ala His Thr Asn Tyr Thr Phe Glu Ile Glu Ala Val Asn Gly Val Ser
        435                 440                 445

Asp Leu Ser Pro Gly Ala Arg Gln Tyr Val Ser Val Asn Val Thr Thr
    450                 455                 460

Asn Gln Ala Ala Pro Ser Pro Val Thr Asn Val Lys Lys Gly Lys Ile
465                 470                 475                 480

Ala Lys Asn Ser Ile Ser Leu Ser Trp Gln Glu Pro Asp Arg Pro Asn
                485                 490                 495

Gly Ile Ile Leu Glu Tyr Glu Ile Lys Tyr Phe Glu Lys Asp Gln Glu
            500                 505                 510

Thr Ser Tyr Thr Ile Ile Lys Ser Lys Glu Thr Thr Ile Thr Ala Glu
        515                 520                 525

Gly Leu Lys Pro Ala Ser Val Tyr Val Phe Gln Ile Arg Ala Arg Thr
    530                 535                 540

Ala Ala Gly Tyr Gly Val Phe Ser Arg Arg Phe Glu Phe Glu Thr Thr
545                 550                 555                 560

Pro Val Phe Ala Ala Ser Ser Asp Gln Ser Gln Ile Pro Val Ile Ala
                565                 570                 575

Val Ser Val Thr Val Gly Val Ile Leu Leu Ala Val Val Ile Gly Val
            580                 585                 590

Leu Leu Ser Gly Ser Cys Cys Glu Cys Gly Cys Gly Arg Ala Ser Ser
        595                 600                 605

Leu Cys Ala Val Ala His Pro Ser Leu Ile Trp Arg Cys Gly Tyr Ser
    610                 615                 620

Lys Ala Lys Gln Asp Pro Glu Glu Glu Lys Met His Phe His Asn Gly
625                 630                 635                 640

His Ile Lys Leu Pro Gly Val Arg Thr Tyr Ile Asp Pro His Thr Tyr
                645                 650                 655

Glu Asp Pro Asn Gln Ala Val His Glu Phe Ala Lys Glu Ile Glu Ala
            660                 665                 670

Ser Cys Ile Thr Ile Glu Arg Val Ile Gly Ala Gly Glu Phe Gly Glu
        675                 680                 685

Val Cys Ser Gly Arg Leu Lys Leu Pro Gly Lys Arg Glu Leu Pro Val
    690                 695                 700

Ala Ile Lys Thr Leu Lys Val Gly Tyr Thr Glu Lys Gln Arg Arg Asp
705                 710                 715                 720

Phe Leu Gly Glu Ala Ser Ile Met Gly Gln Phe Asp His Pro Asn Ile
                725                 730                 735

Ile His Leu Glu Gly Val Val Thr Lys Ser Lys Pro Val Met Ile Val
            740                 745                 750

Thr Glu Tyr Met Glu Asn Gly Ser Leu Asp Thr Phe Leu Lys Lys Asn
        755                 760                 765
```

```
Asp Gly Gln Phe Thr Val Ile Gln Leu Val Gly Met Leu Arg Gly Ile
    770                 775                 780

Ser Ala Gly Met Lys Tyr Leu Ser Asp Met Gly Tyr Val His Arg Asp
785                 790                 795                 800

Leu Ala Ala Arg Asn Ile Leu Ile Asn Ser Asn Leu Val Cys Lys Val
                805                 810                 815

Ser Asp Phe Gly Leu Ser Arg Val Leu Glu Asp Asp Pro Glu Ala Ala
            820                 825                 830

Tyr Thr Thr Arg Gly Gly Lys Ile Pro Ile Arg Trp Thr Ala Pro Glu
        835                 840                 845

Ala Ile Ala Phe Arg Lys Phe Thr Ser Ala Ser Asp Val Trp Ser Tyr
    850                 855                 860

Gly Ile Val Met Trp Glu Val Val Ser Tyr Gly Glu Arg Pro Tyr Trp
865                 870                 875                 880

Glu Met Thr Asn Gln Asp Val Ile Lys Ala Val Glu Glu Gly Tyr Arg
                885                 890                 895

Leu Pro Ser Pro Met Asp Cys Pro Ala Ala Leu Tyr Gln Leu Met Leu
            900                 905                 910

Asp Cys Trp Gln Lys Glu Arg Asn Ser Arg Pro Lys Phe Asp Glu Ile
        915                 920                 925

Val Asn Met Leu Asp Lys Leu Ile Arg Asn Pro Ser Ser Leu Lys Thr
    930                 935                 940

Leu Val Asn Ala Ser Cys Arg Val Ser Asn Leu Leu Ala Glu His Ser
945                 950                 955                 960

Pro Leu Gly Ser Gly Ala Tyr Arg Ser Val Gly Glu Trp Leu Glu Ala
                965                 970                 975

Ile Lys Met Gly Arg Tyr Thr Glu Ile Phe Met Glu Asn Gly Tyr Ser
            980                 985                 990

Ser Met Asp Ala Val Ala Gln Val  Thr Leu Glu Asp Leu  Arg Arg Leu
        995                 1000                1005

Gly Val  Thr Leu Val Gly His  Gln Lys Lys Ile Met  Asn Ser Leu
    1010                1015                1020

Gln Glu  Met Lys Val Gln Leu  Val Asn Gly Met Val  Pro Leu
    1025                1030                1035


<210> SEQ ID NO 40
<211> LENGTH: 1015
<212> TYPE: PRT
<213> ORGANISM: Homo sapiens

<400> SEQUENCE: 40

Met Arg Gly Ser Gly Pro Arg Gly Ala Gly His Arg Arg Pro Pro Ser
1               5                   10                  15

Gly Gly Gly Asp Thr Pro Ile Thr Pro Ala Ser Leu Ala Gly Cys Tyr
            20                  25                  30

Ser Ala Pro Arg Arg Ala Pro Leu Trp Thr Cys Leu Leu Leu Cys Ala
        35                  40                  45

Ala Leu Arg Thr Leu Leu Ala Ser Pro Ser Asn Glu Val Asn Leu Leu
    50                  55                  60

Asp Ser Arg Thr Val Met Gly Asp Leu Gly Trp Ile Ala Phe Pro Lys
65                  70                  75                  80

Asn Gly Trp Glu Glu Ile Gly Glu Val Asp Glu Asn Tyr Ala Pro Ile
                85                  90                  95

His Thr Tyr Gln Val Cys Lys Val Met Glu Gln Asn Gln Asn Asn Trp
            100                 105                 110
```

-continued

```
Leu Leu Thr Ser Trp Ile Ser Asn Glu Gly Ala Ser Arg Ile Phe Ile
        115                 120                 125

Glu Leu Lys Phe Thr Leu Arg Asp Cys Asn Ser Leu Pro Gly Gly Leu
    130                 135                 140

Gly Thr Cys Lys Glu Thr Phe Asn Met Tyr Tyr Phe Glu Ser Asp Asp
145                 150                 155                 160

Gln Asn Gly Arg Asn Ile Lys Glu Asn Gln Tyr Ile Lys Ile Asp Thr
                165                 170                 175

Ile Ala Ala Asp Glu Ser Phe Thr Glu Leu Asp Leu Gly Asp Arg Val
            180                 185                 190

Met Lys Leu Asn Thr Glu Val Arg Asp Val Gly Pro Leu Ser Lys Lys
        195                 200                 205

Gly Phe Tyr Leu Ala Phe Gln Asp Val Gly Ala Cys Ile Ala Leu Val
    210                 215                 220

Ser Val Arg Val Tyr Tyr Lys Glu Cys Pro Ser Val Val Arg His Leu
225                 230                 235                 240

Ala Val Phe Pro Asp Thr Ile Thr Gly Ala Asp Ser Ser Gln Leu Leu
                245                 250                 255

Glu Val Ser Gly Ser Cys Val Asn His Ser Val Thr Asp Glu Pro Pro
            260                 265                 270

Lys Met His Cys Ser Ala Glu Gly Glu Trp Leu Val Pro Ile Gly Lys
        275                 280                 285

Cys Met Cys Lys Ala Gly Tyr Glu Glu Lys Asn Gly Thr Cys Gln Val
    290                 295                 300

Cys Arg Pro Gly Phe Phe Lys Ala Ser Pro His Ile Gln Ser Cys Gly
305                 310                 315                 320

Lys Cys Pro Pro His Ser Tyr Thr His Glu Glu Ala Ser Thr Ser Cys
                325                 330                 335

Val Cys Glu Lys Asp Tyr Phe Arg Arg Glu Ser Asp Pro Pro Thr Met
            340                 345                 350

Ala Cys Thr Arg Pro Pro Ser Ala Pro Arg Asn Ala Ile Ser Asn Val
        355                 360                 365

Asn Glu Thr Ser Val Phe Leu Glu Trp Ile Pro Pro Ala Asp Thr Gly
    370                 375                 380

Gly Arg Lys Asp Val Ser Tyr Tyr Ile Ala Cys Lys Lys Cys Asn Ser
385                 390                 395                 400

His Ala Gly Val Cys Glu Glu Cys Gly Gly His Val Arg Tyr Leu Pro
                405                 410                 415

Arg Gln Ser Gly Leu Lys Asn Thr Ser Val Met Met Val Asp Leu Leu
            420                 425                 430

Ala His Thr Asn Tyr Thr Phe Glu Ile Glu Ala Val Asn Gly Val Ser
        435                 440                 445

Asp Leu Ser Pro Gly Ala Arg Gln Tyr Val Ser Val Asn Val Thr Thr
    450                 455                 460

Asn Gln Ala Ala Pro Ser Pro Val Thr Asn Val Lys Lys Gly Lys Ile
465                 470                 475                 480

Ala Lys Asn Ser Ile Ser Leu Ser Trp Gln Glu Pro Asp Arg Pro Asn
                485                 490                 495

Gly Ile Ile Leu Glu Tyr Glu Ile Lys Tyr Phe Glu Lys Asp Gln Glu
            500                 505                 510

Thr Ser Tyr Thr Ile Ile Lys Ser Lys Glu Thr Thr Ile Thr Ala Glu
        515                 520                 525
```

-continued

```
Gly Leu Lys Pro Ala Ser Val Tyr Val Phe Gln Ile Arg Ala Arg Thr
    530                 535                 540

Ala Ala Gly Tyr Gly Val Phe Ser Arg Arg Phe Glu Phe Glu Thr Thr
545                 550                 555                 560

Pro Val Phe Ala Ala Ser Ser Asp Gln Ser Gln Ile Pro Val Ile Ala
                565                 570                 575

Val Ser Val Thr Val Gly Val Ile Leu Leu Ala Val Val Ile Gly Val
            580                 585                 590

Leu Leu Ser Gly Arg Arg Cys Gly Tyr Ser Lys Ala Lys Gln Asp Pro
        595                 600                 605

Glu Glu Glu Lys Met His Phe His Asn Gly His Ile Lys Leu Pro Gly
    610                 615                 620

Val Arg Thr Tyr Ile Asp Pro His Thr Tyr Glu Asp Pro Asn Gln Ala
625                 630                 635                 640

Val His Glu Phe Ala Lys Glu Ile Glu Ala Ser Cys Ile Thr Ile Glu
                645                 650                 655

Arg Val Ile Gly Ala Gly Glu Phe Gly Glu Val Cys Ser Gly Arg Leu
            660                 665                 670

Lys Leu Pro Gly Lys Arg Glu Leu Pro Val Ala Ile Lys Thr Leu Lys
        675                 680                 685

Val Gly Tyr Thr Glu Lys Gln Arg Arg Asp Phe Leu Gly Glu Ala Ser
    690                 695                 700

Ile Met Gly Gln Phe Asp His Pro Asn Ile Ile His Leu Glu Gly Val
705                 710                 715                 720

Val Thr Lys Ser Lys Pro Val Met Ile Val Thr Glu Tyr Met Glu Asn
                725                 730                 735

Gly Ser Leu Asp Thr Phe Leu Lys Lys Asn Asp Gly Gln Phe Thr Val
            740                 745                 750

Ile Gln Leu Val Gly Met Leu Arg Gly Ile Ser Ala Gly Met Lys Tyr
        755                 760                 765

Leu Ser Asp Met Gly Tyr Val His Arg Asp Leu Ala Ala Arg Asn Ile
    770                 775                 780

Leu Ile Asn Ser Asn Leu Val Cys Lys Val Ser Asp Phe Gly Leu Ser
785                 790                 795                 800

Arg Val Leu Glu Asp Asp Pro Glu Ala Ala Tyr Thr Thr Arg Gly Gly
                805                 810                 815

Lys Ile Pro Ile Arg Trp Thr Ala Pro Glu Ala Ile Ala Phe Arg Lys
            820                 825                 830

Phe Thr Ser Ala Ser Asp Val Trp Ser Tyr Gly Ile Val Met Trp Glu
        835                 840                 845

Val Val Ser Tyr Gly Glu Arg Pro Tyr Trp Glu Met Thr Asn Gln Asp
    850                 855                 860

Val Ile Lys Ala Val Glu Glu Gly Tyr Arg Leu Pro Ser Pro Met Asp
865                 870                 875                 880

Cys Pro Ala Ala Leu Tyr Gln Leu Met Leu Asp Cys Trp Gln Lys Glu
                885                 890                 895

Arg Asn Ser Arg Pro Lys Phe Asp Glu Ile Val Asn Met Leu Asp Lys
            900                 905                 910

Leu Ile Arg Asn Pro Ser Ser Leu Lys Thr Leu Val Asn Ala Ser Cys
        915                 920                 925

Arg Val Ser Asn Leu Leu Ala Glu His Ser Pro Leu Gly Ser Gly Ala
    930                 935                 940

Tyr Arg Ser Val Gly Glu Trp Leu Glu Ala Ile Lys Met Gly Arg Tyr
```

-continued

```
945                 950                 955                 960

Thr Glu Ile Phe Met Glu Asn Gly Tyr Ser Ser Met Asp Ala Val Ala
                965                 970                 975

Gln Val Thr Leu Glu Asp Leu Arg Arg Leu Gly Val Thr Leu Val Gly
            980                 985                 990

His Gln Lys Lys Ile Met Asn Ser  Leu Gln Glu Met Lys  Val Gln Leu
        995                 1000                1005

Val Asn  Gly Met Val Pro Leu
    1010                1015


<210> SEQ ID NO 41
<211> LENGTH: 415
<212> TYPE: PRT
<213> ORGANISM: Homo sapiens

<400> SEQUENCE: 41

Met Asp Phe Asp Lys Lys Gly Gly Lys Gly Glu Thr Glu Glu Gly Arg
1               5                   10                  15

Arg Met Ser Lys Ala Gly Gly Gly Arg Ser Ser His Gly Ile Arg Ser
            20                  25                  30

Ser Gly Thr Ser Ser Gly Val Leu Met Val Gly Pro Asn Phe Arg Val
        35                  40                  45

Gly Lys Lys Ile Gly Cys Gly Asn Phe Gly Glu Leu Arg Leu Gly Lys
    50                  55                  60

Asn Leu Tyr Thr Asn Glu Tyr Val Ala Ile Lys Leu Glu Pro Ile Lys
65                  70                  75                  80

Ser Arg Ala Pro Gln Leu His Leu Glu Tyr Arg Phe Tyr Lys Gln Leu
                85                  90                  95

Ser Ala Thr Glu Gly Val Pro Gln Val Tyr Tyr Phe Gly Pro Cys Gly
            100                 105                 110

Lys Tyr Asn Ala Met Val Leu Glu Leu Leu Gly Pro Ser Leu Glu Asp
        115                 120                 125

Leu Phe Asp Leu Cys Asp Arg Thr Phe Thr Leu Lys Thr Val Leu Met
    130                 135                 140

Ile Ala Ile Gln Leu Ile Thr Arg Met Glu Tyr Val His Thr Lys Ser
145                 150                 155                 160

Leu Ile Tyr Arg Asp Val Lys Pro Glu Asn Phe Leu Val Gly Arg Pro
                165                 170                 175

Gly Thr Lys Arg Gln His Ala Ile His Ile Ile Asp Phe Gly Leu Ala
            180                 185                 190

Lys Glu Tyr Ile Asp Pro Glu Thr Lys Lys His Ile Pro Tyr Arg Glu
        195                 200                 205

His Lys Ser Leu Thr Gly Thr Ala Arg Tyr Met Ser Ile Asn Thr His
    210                 215                 220

Leu Gly Lys Glu Gln Ser Arg Arg Asp Asp Leu Glu Ala Leu Gly His
225                 230                 235                 240

Met Phe Met Tyr Phe Leu Arg Gly Ser Leu Pro Trp Gln Gly Leu Lys
                245                 250                 255

Ala Asp Thr Leu Lys Glu Arg Tyr Gln Lys Ile Gly Asp Thr Lys Arg
            260                 265                 270

Ala Thr Pro Ile Glu Val Leu Cys Glu Asn Phe Pro Glu Glu Met Ala
        275                 280                 285

Thr Tyr Leu Arg Tyr Val Arg Arg Leu Asp Phe Phe Glu Lys Pro Asp
    290                 295                 300
```

-continued

```
Tyr Asp Tyr Leu Arg Lys Leu Phe Thr Asp Leu Phe Asp Arg Ser Gly
305                 310                 315                 320

Phe Val Phe Asp Tyr Glu Tyr Asp Trp Ala Gly Lys Pro Leu Pro Thr
                325                 330                 335

Pro Ile Gly Thr Val His Thr Asp Leu Pro Ser Gln Pro Gln Leu Arg
            340                 345                 350

Asp Lys Thr Gln Pro His Ser Lys Asn Gln Ala Leu Asn Ser Thr Asn
        355                 360                 365

Gly Glu Leu Asn Ala Asp Asp Pro Thr Ala Gly His Ser Asn Ala Pro
    370                 375                 380

Ile Thr Ala Pro Ala Glu Val Glu Val Ala Asp Glu Thr Lys Cys Cys
385                 390                 395                 400

Cys Phe Phe Lys Arg Arg Lys Arg Lys Ser Leu Gln Arg His Lys
                405                 410                 415


<210> SEQ ID NO 42
<211> LENGTH: 351
<212> TYPE: PRT
<213> ORGANISM: Homo sapiens

<400> SEQUENCE: 42

Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Phe Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255

Gly Gln Val Val Leu Leu Leu Asp Gly Leu Gly Cys Glu Ser Cys Asn
            260                 265                 270
```

```
Val Leu Ala Val Glu Lys Tyr Phe Leu Leu Leu Ala Glu Ala Asn Ser
        275                 280                 285

Leu Val Asn Ala Ala Val Tyr Ser Cys Arg Asp Ala Glu Met Arg Arg
    290                 295                 300

Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Asp Ser Thr Leu
            340                 345                 350
```

<210> SEQ ID NO 43
<211> LENGTH: 19
<212> TYPE: DNA
<213> ORGANISM: Homo sapiens

<400> SEQUENCE: 43
catggctcta gttgtcgac 19

<210> SEQ ID NO 44
<211> LENGTH: 19
<212> TYPE: DNA
<213> ORGANISM: Homo sapiens

<400> SEQUENCE: 44
tatcctgctg gatgaacac 19

<210> SEQ ID NO 45
<211> LENGTH: 19
<212> TYPE: DNA
<213> ORGANISM: Homo sapiens

<400> SEQUENCE: 45
gtaggagtga aagcacttc 19

<210> SEQ ID NO 46
<211> LENGTH: 19
<212> TYPE: DNA
<213> ORGANISM: Homo sapiens

<400> SEQUENCE: 46
tacttgaaca cgactgagc 19

<210> SEQ ID NO 47
<211> LENGTH: 19
<212> TYPE: DNA
<213> ORGANISM: Homo sapiens

<400> SEQUENCE: 47
ctgctacgag aacttcacc 19

<210> SEQ ID NO 48
<211> LENGTH: 19
<212> TYPE: DNA
<213> ORGANISM: Homo sapiens

<400> SEQUENCE: 48
gatgctcaca aaccacacc 19

<210> SEQ ID NO 49
<211> LENGTH: 19

-continued

<212> TYPE: DNA
<213> ORGANISM: Homo sapiens

<400> SEQUENCE: 49
ctttcagcct atggcaagc 19

<210> SEQ ID NO 50
<211> LENGTH: 19
<212> TYPE: DNA
<213> ORGANISM: Homo sapiens

<400> SEQUENCE: 50
atgatcctgt atgacctgc 19

<210> SEQ ID NO 51
<211> LENGTH: 19
<212> TYPE: DNA
<213> ORGANISM: Homo sapiens

<400> SEQUENCE: 51
tccaagatct ccacctgcc 19

<210> SEQ ID NO 52
<211> LENGTH: 19
<212> TYPE: DNA
<213> ORGANISM: Homo sapiens

<400> SEQUENCE: 52
gttggagctg gacggtgac 19

<210> SEQ ID NO 53
<211> LENGTH: 19
<212> TYPE: DNA
<213> ORGANISM: Homo sapiens

<400> SEQUENCE: 53
gatccaggac accaaaggc 19

<210> SEQ ID NO 54
<211> LENGTH: 19
<212> TYPE: DNA
<213> ORGANISM: Homo sapiens

<400> SEQUENCE: 54
catcttcgac tccatgatc 19

<210> SEQ ID NO 55
<211> LENGTH: 19
<212> TYPE: DNA
<213> ORGANISM: Homo sapiens

<400> SEQUENCE: 55
agatcagtag gtgaatggc 19

<210> SEQ ID NO 56
<211> LENGTH: 19
<212> TYPE: DNA
<213> ORGANISM: Homo sapiens

<400> SEQUENCE: 56
accaggcgtt gaactccac 19

<210> SEQ ID NO 57

<211> LENGTH: 19
<212> TYPE: DNA
<213> ORGANISM: Homo sapiens

<400> SEQUENCE: 57
tctgctggtc atagcagcc 19

<210> SEQ ID NO 58
<211> LENGTH: 12
<212> TYPE: RNA
<213> ORGANISM: Artificial Sequence
<220> FEATURE:
<223> OTHER INFORMATION: Synthetic linker

<400> SEQUENCE: 58
guuugcuaua ac 12

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
ccgtttacgt ggagactcgc c 21

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
cccccacctt atatatattc tttcc 25

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
tggagatcag cccaaaccc 19

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
gccagtggag gaagttttcg 20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
aagacggtgc tgatgatcgc 20

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
cacatactcc atgcgcgtg 19

<210> SEQ ID NO 65
<211> LENGTH: 19
<212> TYPE: DNA
<213> ORGANISM: Artificial Sequence
<220> FEATURE:
<223> OTHER INFORMATION: Primer

<400> SEQUENCE: 65
ccacaatggc atgcacaag 19

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
ttgagatggc attccgagg 19

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gacgcagagg caaagacaca 20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ccacacccct gtcctcattt 20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
cacctcaagt gcaaggacca 20

<210> SEQ ID NO 70
<211> LENGTH: 19
<212> TYPE: DNA
<213> ORGANISM: Artificial Sequence
<220> FEATURE:

<223> OTHER INFORMATION: Primer

<400> SEQUENCE: 70
aagccaaccc actccaagc 19

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ttgcatggaa cacatggacg 20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
gcctctttca gcacctggtc 20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
gcatcttcat cctgaaccgg 20

<210> SEQ ID NO 74
<211> LENGTH: 19
<212> TYPE: DNA
<213> ORGANISM: Artificial Sequence
<220> FEATURE:
<223> OTHER INFORMATION: Primer

<400> SEQUENCE: 74
agagcatttc cagcgtggc 19

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
caccatcttt tacgcgctcc 20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
gccttcctca cggtcatgat 20

-continued

```
<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77

ttcccagatc atccattgca                                                20


<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78

cgtttccttt agccttctca ctga                                           24


<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79

gaatatgggc gggaaccact                                                20


<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80

tcattctcgt caaacacggg                                                20
```

METHODS AND MEANS FOR TREATMENT OF OSTEOARTHRITIS

CROSS REFERENCE TO RELATED APPLICATIONS

The present application is a Divisional Application of U.S. application Ser. No. 14/162,908 filed Jan. 24, 2014, now abandoned, which is a divisional of National Stage Application U.S. Ser. No. 13/262,634 filed Oct. 1, 2011, now U.S. Pat. No. 8,663,930, claiming the priority of co-pending PCT Application No. PCT/EP2010/054412 filed Apr. 1, 2010, which in turn, claims priority from U.S. Provisional Application Ser. No. 61/211,740 filed Apr. 1, 2009. Applicants claim the benefits of 35 U.S.C. § 120 as to the U.S. Application and U.S. National Stage application and the PCT application and priority under 35 U.S.C. § 119 as to the said U.S. provisional application, and the entire disclosures of both applications are incorporated herein by reference in their entireties.

FIELD OF THE INVENTION

The invention relates to the field of medicinal research, inflammation, cartilage physiology and diseases involving inflammation and/or the degeneration of cartilage tissue and/or extracellular matrix (ECM). More specifically, the present invention relates to agents, and methods for identifying compounds, which agents and compounds inhibit catabolic processes in chondrocytes and that would decrease the degradation of cartilage and/or extracellular matrix. The invention also relates to targets, the modulation of which results in a decrease in the degradation of ECM and/or cartilage and decrease inflammation. In addition, the invention relates to compositions and methods for the use thereof in treating conditions that are characterized by the degradation of ECM and/or cartilage and inflammation. The invention also relates to the compounds that are useful in the treatment of osteoarthritis.

BACKGROUND OF THE INVENTION

Cartilage is an avascular tissue of which chondrocytes are the main cellular component. The chondrocytes in normal articular cartilage occupy approximately 5% of the tissue volume, while the extra-cellular matrix makes up the remaining 95% of the tissue. The chondrocytes secrete the components of the matrix, mainly proteoglycans and collagens, which in turn supply the chondrocytes with an environment suitable for their survival under mechanical stress. In cartilage, collagen type II, together with the protein collagen type IX, is arranged in solid fibril-like structures which provide cartilage with great mechanical strength. The proteoglycans can absorb water and are responsible for the resilient and shock absorbing properties of the cartilage.

One of the functional roles of cartilage in the joint is to allow bones to articulate on each other smoothly. Loss of articular cartilage, therefore, causes the bones to rub against each other leading to pain and loss of mobility. The degradation of cartilage can have various causes. In inflammatory arthritides, as rheumatoid arthritis for example, cartilage degradation is caused by the secretion of proteases (e.g. collagenases) by inflamed tissues (the inflamed synovium for example). Cartilage degradation can also be the result of an injury of the cartilage, due to an accident or surgery, or exaggerated loading or 'wear and tear'. Cartilage degradation may also be the result of an imbalance in cartilage synthesizing (anabolic) and cartilage degrading (catabolic) processes. The ability of cartilage tissue to regenerate after such insults is limited. Chondrocytes in injured cartilage often display reduced anabolic activity and/or increased catabolic activity. The limited ability of cartilage to self-repair after injury, disease, or surgery is a major limiting factor in rehabilitation of degrading joint surfaces and injury to meniscal cartilage.

The degeneration of cartilage is the hallmark of various diseases, among which rheumatoid arthritis and osteoarthritis are the most prominent.

Osteoarthritis (also referred to as OA, or wear-and-tear arthritis) is the most common form of arthritis and is characterized by loss of articular cartilage, often associated with hypertrophy of the bone and pain. The disease mainly affects hands and weight-bearing joints such as knees, hips and spines. This process thins the cartilage. When the surface area has disappeared due to the thinning, a grade I osteoarthritis is reached; when the tangential surface area has disappeared, grade II osteoarthritis is reached. There are further levels of degeneration and destruction, which affect the deep and the calcified cartilage layers that border with the subchondral bone. For an extensive review on osteoarthritis, we refer to Wieland et al., 2005.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

The clinical manifestations of the development of the osteoarthritis condition are: increased volume of the joint, pain, crepitation and functional disability that lead to pain and reduced mobility of the joints. When disease further develops, pain at rest emerges. If the condition persists without correction and/or therapy, the joint is destroyed leading to disability. Replacement surgery with total prosthesis is then required.

In mature articular cartilage, chondrocytes maintain the cartilage-specific matrix phenotype. Early signs of OA include progressive loss from articular cartilage of the proteoglycan aggrecan, due to damage to type II collagen. This protein represents the major structural collagen found in articular cartilage in healthy individuals. There is ordinarily a strict balance between the production of type II collagen and degradation of this protein by catabolic enzymes during normal remodeling of cartilage. Pathological conditions such as OA are characterized by a loss of this balance with increased proteolysis.

In general, elevated expression of MMPs is associated with the degradation of cartilage and/or extracellular matrix (ECM) but not all proteases are capable of degrading native collagen. Among the matrix metallo proteinases, MMP1, MMP8, MMP13 and MMP14 display the highest capacity for degrading collagen type II. Expression and contents of MMP-1 (collagenase-1) and MMP-13 (Mitchel et al., 1996; Shlopov et al., 1997), expression of MMP-8 (collagenase-2), and collagenase activity (Billinghurst et al., 1997, Dahlberg et al., 2000) are upregulated in human OA cartilage. In particular, MMP-13, also known as collagenase-3, is thought to play an important role in type II collagen degradation in articular cartilage and especially in OA (Billinghurst et al., 1997, Mitchell et al., 1996, Dahlberg et al., 2000, Billinghurst et al., 2000) as indicated by various observations. 1) The expression of MMP13 is increased in the cartilage of OA patients and of animals subjected to arthritogenic surgery like meniscectomy (Appleton et al., 2007) 2) The localization of MMP1 and MMP13 in arthritic cartilage appear to coincide with the location of cartilage destruction, as revealed by antibodies revealing neo-epitopes induced by cartilage cleavage. (Wu et al., 2002) 3) Overexpression of MMP13 in cartilage of transgenic mice lead to an OA-like cartilage destruction phenotype (Neuhold et al., 2001). 4) Type II collagen is the preferred substrate for MMP-13 (Billinghurst et al., 1997; Mitchell et al., 1996). Taken together, MMP13 is well-accepted as a key player in OA-induced cartilage and ECM degeneration.

Therapeutic methods for the correction of the articular cartilage lesions that appear during osteoarthritic disease have been developed, but so far none of them have been able to mediate the regeneration of articular cartilage in situ and in vivo.

Osteoarthritis is difficult to treat. At present, no cure is available and treatment focuses on relieving pain and preventing the affected joint from becoming deformed. Common treatments include the use of non-steroidal anti-inflammatory drugs (NSAIDs). Although dietary supplements such as chondroitin and glucosamine sulphate have been advocated as safe and effective options for the treatment or amelioration of osteoarthritis, a recent clinical trial revealed that both treatments did not reduce pain associated with osteoarthritis (Clegg et al., 2006). Taken together, no disease modifying osteoarthritic drugs are available.

In severe cases, joint replacement may be necessary. This is especially true for hips and knees. If a joint is extremely painful and cannot be replaced, it may be fused. This procedure stops the pain, but results in the permanent loss of joint function, making walking and bending difficult.

Another possible treatment is the transplantation of cultured autologous chondrocytes. Here, chondral cellular material is taken from the patient, sent to a laboratory where it is expanded. The material is then implanted in the damaged tissues to cover the tissue's defects.

Another treatment includes the intra-articular instillation of Hylan G-F 20 (e.g. Synvisc®, Hyalgan®, Artz®), a substance that improves temporarily the rheology of the synovial fluid, producing an almost immediate sensation of free movement and a marked reduction of pain.

Other reported methods include application of tendinous, periosteal, fascial, muscular or perichondral grafts; implantation of fibrin or cultured chondrocytes; implantation of synthetic matrices, such as collagen, carbon fiber; administration of electromagnetic fields. All of these have reported minimal and incomplete effects, resulting in a poor quality tissue that can neither support the weighted load nor allow the restoration of an articular function with normal movement.

Stimulation of the anabolic processes, blocking catabolic processes, or a combination of these two, may result in stabilization of the cartilage, and perhaps even reversion of the damage, and therefore prevent further progression of the disease.

The present invention relates to the relationship between the function of selected proteins identified by the present inventors (hereinafter referred to as "TARGETS") and inhibition of cartilage and/or extra-cellular matrix (ECM) degradation and inhibition of inflammation.

SUMMARY OF THE INVENTION

The present invention relates to a method for identifying compounds that reduce extra-cellular matrix (ECM) and/or cartilage degradation processes comprising contacting the compound with a polypeptide comprising an amino acid sequence selected from the group consisting of SEQ ID NO: 22-42 (hereinafter "TARGETS"), or a functional fragment thereof, under conditions that allow said polypeptide to bind to the compound, and measuring a compound-polypeptide property related to the inhibition of ECM and/or cartilage degradation. In a particular embodiment the compound-polypeptide property is the level of inflammatory cytokines for example IL-1b, IL-6, IL-8, IL-11, TNFα and/or LIF. In a specific embodiment the compound-polypeptide property measured is expression levels of cartilage degradation proteins or proteases such as collagenase. In a particular embodiment the compound-polypeptide property measured is the expression levels of MMP1, MMP3, MMP8, MMP13, MMP14, and/or ADAMTS4. In a specific embodiment the compound-polypeptide property measured is MMP13 expression levels.

Aspects of the present method include the in vitro assay of compounds using the polypeptide corresponding to a TARGET, or fragments thereof, such fragments being fragments of the amino acid sequences described by SEQ ID NO: 22-42, and cellular assays wherein TARGET inhibition is followed by observing indicators of efficacy including, for example, TARGET expression levels, TARGET enzymatic activity and/or MMP13 levels.

The present invention also relates to (1) expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a TARGET polypeptide said polynucleotide sequence comprising a sequence selected from the group consisting of SEQ ID NO: 22-42, and (2) pharmaceutical compositions comprising said agent(s), useful in the treatment, or prevention, of diseases characterized by ECM degradation and/or cartilage degradation such as osteoarthritis.

Another aspect of the invention is a method of treatment, or prevention, of a condition related to cartilage and/or ECM degeneration, bone and/or joint degradation, in a subject suffering or susceptible thereto, by administering a pharmaceutical composition comprising an effective TARGET-expression inhibiting amount of a expression-inhibitory agent or an effective TARGET activity inhibiting amount of a activity-inhibitory agent. In a particular embodiment the condition is osteoarthritis.

Another aspect of the invention is a method of treatment, or prevention, of a condition related to inflammation, in a subject suffering or susceptible thereto, by administering a pharmaceutical composition comprising an effective TARGET-expression inhibiting amount of a expression-inhibitory agent or an effective TARGET activity inhibiting amount of a activity-inhibitory agent.

A further aspect of the present invention is a method for diagnosis of a condition related to cartilage and/or ECM degeneration comprising measurement of indicators of levels of TARGET expression and/or activity in a subject.

A further aspect of the present invention is a method for diagnosis of a condition related to inflammation comprising measurement of indicators of levels of TARGET expression and/or activity in a subject.

Another aspect of this invention relates to the use of agents which inhibit a TARGET as disclosed herein in a therapeutic method, a pharmaceutical composition, and the manufacture of such composition, useful for the treatment of a disease involving cartilage and/or ECM degeneration. In particular, the present method relates to the use of the agents which inhibit a TARGET in the treatment of a disease characterized by joint degradation, and in particular, a disease characterized by abnormal MMP13 expression. The agents are useful for amelioration or treatment of a disease involving cartilage degradation, including but not limited to osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease, and Handigodu disease; degeneration resulting from fibromyalgia, systemic lupus erythematosus, scleroderma, ankylosing spondylitis, congenital cartilage malformations, including hereditary chondrolysis, chondrodysplasias and pseudoachondrodysplasias, and congenital cartilage malformation related diseases for example microtia, anotia, and metaphyseal chondrodysplasia. In a particular embodiment the disease is selected from osteoarthritis, rheumatoid arthritis, and inflammatory arthritis. In a particular embodiment the disease is osteoarthritis.

Another aspect of this invention relates to the use of agents which inhibit a TARGET as disclosed herein in a therapeutic method, a pharmaceutical composition, and the manufacture of such composition, useful for the treatment of a disease involving inflammation, including but not limited to allergic airways disease (e.g. asthma, rhinitis), autoimmune diseases, transplant rejection, Crohn's disease, rheumatoid arthritis, psoriasis, juvenile idiopathic arthritis, colitis, and inflammatory bowel diseases.

In a further aspect the present invention also relates to methods for the in vitro production of cartilage tissue.

Another further aspect of the present invention is a pharmaceutical composition comprising a therapeutically effective cartilage and/or ECM degradation-inhibiting amount of a TARGET inhibitor or its pharmaceutically acceptable salt, hydrate, solvate, or prodrug thereof in admixture with a pharmaceutically acceptable carrier. The present polynucleotides and TARGET inhibitor compounds are also useful for the manufacturing of a medicament for the treatment of conditions involving ECM degradation, cartilage degradation, and/or inflammation.

Furthermore, the invention also relates to diagnostic methods.

Other objects and advantages will become apparent from a consideration of the ensuing description taken in conjunction with the following illustrative drawings

BRIEF DESCRIPTION OF THE DRAWINGS

FIG. 7 lists the oligonucleotide primers used for SYBR® Green quantitative real-time PCR.

DETAILED DESCRIPTION

Figure 1:
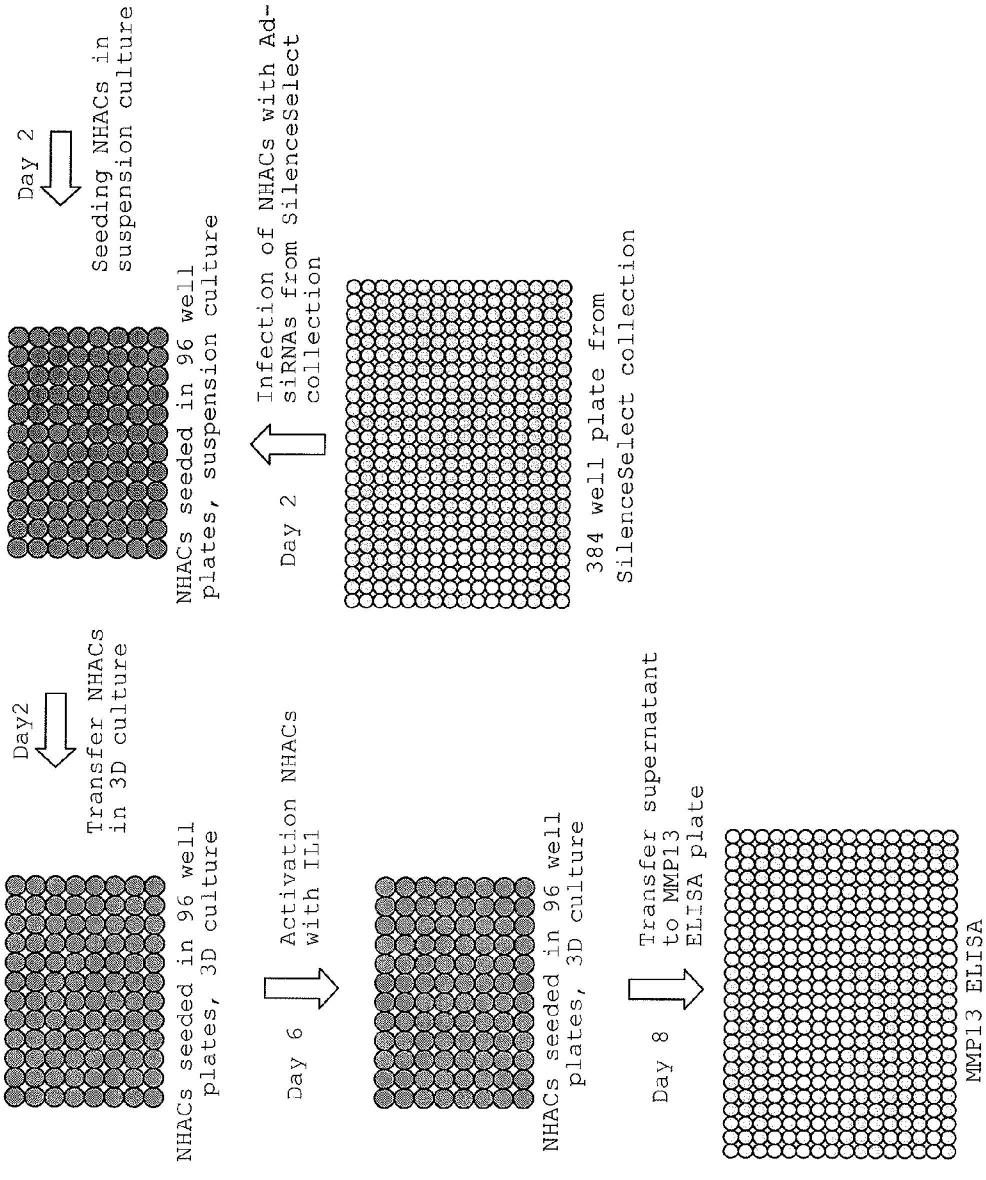
FIG. 1. Shows the principle of the general screening protocol for the MMP13 assay in normal human articular chondrocytes (NHACs)
Figure 2:
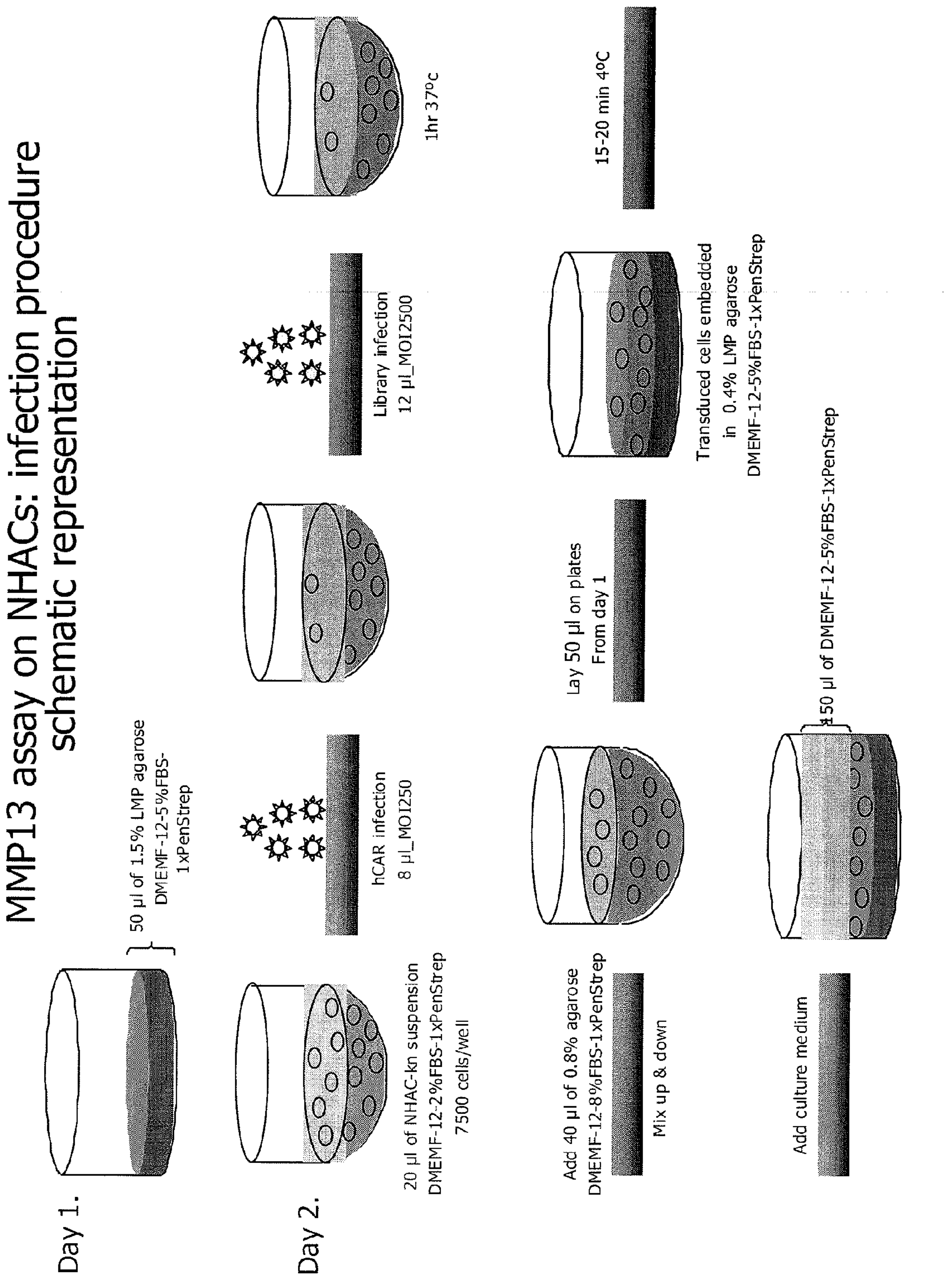
FIG. 2: Schematic representation of the MMP13 assay in normal human articular chondrocyes

The following terms are intended to have the meanings presented therewith below and are useful in understanding the description and intended scope of the present invention.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

As used herein, the term 'antagonist' is used to describe a compound that does not provoke a biological response itself upon binding to a receptor, but blocks or dampens agonist-mediated responses, or prevents or reduces agonist binding and, thereby, agonist-mediated responses.

The term 'assay' means any process used to measure a specific property of an agent. A 'screening assay' means a process used to characterize or select agents based upon their activity from a collection of agents.

The term 'binding affinity' is a property that describes how strongly two or more compounds associate with each other in a non-covalent relationship. Binding affinities can be characterized qualitatively (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically, recombinantly, or from natural sources.

The compounds include inorganic or organic compounds such as polynucleotides, lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical indicators or diagnostic indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethyl-phosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'endogenous' shall mean a material that a mammal naturally produces. Endogenous in reference to the term 'protease', 'kinase', 'factor', or 'receptor' shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both in vivo and in vitro systems. For example, and without limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term 'expressible nucleic acid' means a nucleic acid coding for a proteinaceous molecule, an RNA molecule, or a DNA molecule.

The term 'expression' comprises both endogenous expression and overexpression by transduction.

The term 'expression inhibitory agent' means a polynucleotide designed to interfere selectively with the transcription, translation and/or expression of a specific polypeptide or protein normally expressed within a cell. More particularly, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary expression inhibitory molecules include ribozymes, double stranded siRNA molecules, self-complementary single-stranded siRNA molecules (shRNA), genetic antisense constructs, and synthetic RNA antisense molecules with modified stabilized backbones.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'hybridization' means any process by which a strand of nucleic acid binds with a complementary strand through base pairing. The term 'hybridization complex' refers to a complex formed between two nucleic acid sequences by virtue of the formation of hydrogen bonds between complementary bases. A hybridization complex may be formed in solution (for example, $C_{0t}$ or $R_{0t}$ analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency. The term 'standard hybridization conditions' refers to salt and temperature conditions substantially equivalent to 5×SSC and 65° C. for both hybridization and wash. However, one skilled in the art will appreciate that such 'standard hybridization conditions' are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

The term 'inhibit' or 'inhibiting', in relationship to the term 'response' means that a response is decreased or prevented in the presence of a compound as opposed to in the absence of the compound. The term inhibit or inhibiting more generally refers to the relative reduction, decrease, or prevention of an activity or measurable phenomenon, particularly in the presence of a compound versus in the absence of a compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression or activity of a protein or polypeptide.

The term 'ligand' means a molecule, including an endogenous, naturally occurring or synthetic, non-natural molecules, specific for an endogenous, naturally occurring receptor.

The term 'pharmaceutically acceptable salts' refers to the non-toxic, inorganic and organic acid addition salts, and base addition salts, of compounds which inhibit the expression or activity of TARGETS as disclosed herein. These salts can be prepared in situ during the final isolation and purification of compounds useful in the present invention.

The term 'polypeptide' relates to proteins (such as TARGETS), proteinaceous molecules, fragments of proteins, monomers, subunits or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, most particularly 90 percent, and in a particular embodiment, 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A particular embodiment of polynucleotide is the polyribonucleotide of from about 17 to about 22 nucleotides, more commonly described as small interfering RNAs (siRNAs—double stranded siRNA molecules or self-complementary single-stranded siRNA molecules (shRNA)). Another particular embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'solvate' means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term 'subject' includes humans and other mammals.

'Therapeutically effective amount' means that amount of a drug, compound, expression inhibitory agent, or pharmaceutical agent that will elicit the biological or medical response of a subject that is being sought by a medical doctor or other clinician.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term "vectors" also relates to plasmids as well as to viral vectors, such as recombinant viruses, or the nucleic acid encoding the recombinant virus.

The term "vertebrate cells" means cells derived from animals having vertera structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine murine, such as mice and rats, and rabbits.

The term 'TARGET' or 'TARGETS' means the protein(s) identified in accordance with the assays described herein and determined to be involved ECM and/or cartilage degradation. The term TARGET or TARGETS includes and contemplates alternative species forms, isoforms, and variants, such as splice variants, allelic variants, alternate in frame exons, and alternative or premature termination or start sites, including known or recognized isoforms or variants thereof such as indicated in Table 1.

The term 'disease characterized by ECM and/or cartilage degradation' refers to a disease or condition which involves, results at least in part from, or includes a breakdown of the extracellular matrix or a breakdown in cartilage or wherein the degradation of, degeneration of, or loss of cartilage and/or ECM exceeds the generation or regeneration of cartilage and/or ECM. The term includes, but is not limited to, exemplary diseases selected from osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease, and Handigodu disease; degeneration resulting from fibromyalgia, systemic lupus erythematosus, scleroderma, ankylosing spondylitis, congenital cartilage malformations, including hereditary chondrolysis, chondrodysplasias and pseudoachondrodysplasias, and congenital cartilage malformation related diseases for example microtia, anotia, and metaphyseal chondrodysplasia.

The term 'disease characterized by inflammation' refers to a disease which involves, results at least in part from or includes inflammation. The term includes, but is not limited to, exemplary diseases selected from allergic airways disease (e.g. asthma, rhinitis), autoimmune diseases, transplant rejection, Crohn's disease, rheumatoid arthritis, psoriasis, juvenile idiopathic arthritis, colitis, and inflammatory bowel diseases.

TARGETS

The present invention is based on the present inventors' discovery that TARGETS are factors in the regulation of catabolic processes of chondrocytes, and in particular factors whose inhibition leads to a decrease in the catabolism of cartilage and/or ECM. Such a decrease may be monitored by following the expression of proteins related to cartilage and/or ECM degradation, for example but without limitation, MMP1, MMP3, MMP8, MMP13, MMP14, and/or ADAMTS4, in particular MMP13. The term "TARGET" or "TARGETS" means the proteins identified in accordance with the assay described below to be involved in the inhibition of ECM and/or cartilage degradation.

The TARGETS listed in Table 1 below were identified herein as involved in the pathway that regulates or modulates the catabolism of cartilage, particularly as involved in inhibiting the catabolism of cartilage, therefore, inhibitors of these TARGETS are able to inhibit degradation of cartilage and are of use in the prevention and/or treatment of diseases characterized by cartilage degradation.

The TARGETS are also factors in inflammatory processes, in particular they were identified as being involved in a reduction of the response to pro-inflammatory stimuli, particularly the response to IL1 stimulation, therefore inhibitors of these TARGETS are able to inhibit inflammatory processes and are of use in the prevention and/or treatment of diseases characterized by inflammation.

Therefore in one aspect, the present invention relates to a method for assaying for compounds that decrease ECM and/or cartilage degradation or inhibit inflammation, comprising contacting the compound with a polypeptide comprising an amino acid sequence of the polypeptides of SEQ ID NO: 22-42 ("TARGETS") or a fragment thereof under conditions that allow said polypeptide to bind to the compound, and detecting the formation of a complex between the polypeptide and the compound. In particular said method is used to identify an agent that inhibits the degradation of cartilage. In particular said method may be used to identify drug candidate compounds that inhibit the degradation of cartilage via chondrocytes. In an alternative embodiment the method is used to identify an agent that inhibits inflammation. In an alternative embodiment the method is used to identify an agent that inhibits ECM degradation. One preferred means of measuring the complex formation is to determine the binding affinity of said compound to said polypeptide.

More particularly, the invention relates to a method for identifying an agent that reduces degradation of ECM and/or cartilage by chondrocytes, the method comprising:

(a) contacting a population of chondrocyte cells with one or more compound(s) that exhibits binding affinity for a TARGET polypeptide, or fragment thereof, and (b) measuring a compound-polypeptide property related to the inhibition of ECM and/or cartilage degradation.

In a further aspect of the present invention said method is used to identify a compound that modulates the expression of or activity of one or more cartilage degrading enzyme, including for example MMP1, MMP3, MMP8, MMP13, MMP14, and/or ADAMTS4. In particular the inhibition of MMP13 expression may be measured.

In a further aspect of the present invention said method is used to identify a compound that modulates the expression or activity of one or more inflammatory cytokines, including for example IL-1b, IL-6, IL-8, IL-11, TNFα and/or LIF In a further aspect, the present invention relates to a method for assaying for drug candidate compounds that inhibit cartilage and/or ECM degradation said method comprising contacting the compound with a polypeptide comprising an amino acid sequence selected from SEQ ID NO: 22-42, or a fragment thereof, under conditions that allow said compound to modulate the activity or expression of the polypeptide, and determining the activity or expression of the polypeptide. In particular said method may be used to identify drug candidate compounds capable of suppressing expression of MMP1, MMP3, MMP8, MMP13, MMP14, and/or ADAMTS4, in particular suppressing the expression of MMP13. In particular said method may be to identify drug candidate compounds capable of suppressing the expression of MMP1, MMP3, MMP8, MMP13, MMP14, and/or ADAMTS4, in particular MMP13, in normal human articular chondrocytes (NHACs). One particular means of measuring the activity or expression of the polypeptide is to determine the amount of said polypeptide using a polypeptide binding agent, such as an antibody, or to determine the activity of said polypeptide in a biological or biochemical measure, for instance the amount of phosphorylation of a target of a kinase polypeptide, or the amount of degradation by an enzyme or on an enzyme's substrate polypeptide.

The compound-polypeptide property referred to above is related to the inhibition of ECM and/or cartilage degradation, and is a measurable phenomenon chosen by the person of ordinary skill in the art. The measurable property may e.g. be the binding affinity for a peptide domain of the polypeptide TARGET or the level of any one of a number of biochemical marker levels of decreased catabolism by chondrocytes. Catabolic inhibition of chondrocytes can e.g. be measured by measuring the level of proteins and other molecules that are induced as part of the degradation pathway. In particular, the level of MMP13 may be measured.

In addition, compound-polypeptide properties related to the inhibition of ECM and/or cartilage degradation may be measured in normal human articular chondrocytes (NHACs), SW1353 (chondrosarcoma cells), fibroblasts (e.g. synovial fibroblasts), or differentiating mesenchymal stem cell cultures. To some extent, such properties could be measured in cells displaying expression of cartilage degrading enzymes, including MMP1, MMP3, MMP8, MMP13, MMP14, and/or ADAMTS4 expression. However, such properties are also measured in alternative cell systems. For example, in situ binding assays that determine the affinity of compounds to bind to polypeptides of the invention are performed using any cell type that expresses the polypeptide. Expression of the polypeptide is exogenous or endogenous. Furthermore, when the compound-polypeptide property is activation of a biological pathway, any cell that contains the pathway cellular components is used to measure the compound-polypeptide property. The cell may inherently contain these components or may be engineered to express one or more component or express a variant of a component which is labeled or measurable. For example, induction of MMP13 in response to IL-1 stimulation of NHACs is indicative of cartilage and/or ECM degradation. Specifically, cells can be engineered to contain a reporter molecule activated by the MMP13 promoters. In this way alternative cells can be used to measure a property indicative of inhibition of cartilage and/or ECM degradation.

In an additional aspect, the present invention relates to a method for assaying for drug candidate compounds that inhibit cartilage and/or ECM degradation, said method, comprising contacting the compound with a nucleic acid encoding a TARGET polypeptide, including a nucleic acid sequence selected from SEQ ID NO: 1-21, or a fragment thereof, under conditions that allow said nucleic acid to bind to or otherwise associate with the compound, and detecting the formation of a complex between the nucleic acid and the compound. In particular, said method may be used to identify drug candidate compounds able to reduce the level of proteins and other molecules that are induced as part of the degradation pathway. In particular, said method may be used to identify drug candidate compounds able to reduce the level of MMP1, MMP3, MMP8, MMP13, MMP14, and/or ADAMTS4. In particular, said method may be used to identify drug candidate compounds able to reduce the level of MMP13. One particular means of measuring the complex formation is to determine the binding affinity of said compound to said nucleic acid or the presence of a complex by virtue of resistance to nucleases or by gel mobility assays. Alternatively, complex formation may be determined by inhibition of nucleic acid transcription or translation.

The invention relates to a method for identifying a compound that decreases the degradation of cartilage and/or ECM, said method comprising the steps of: culturing a population of cells expressing a polypeptide of any one of those listed in Table 1, or a functional fragment or derivative thereof; determining a first level of MMP1, MMP3, MMP8, MMP13, MMP14, and/or ADAMTS4 expression in response to IL-1 stimulation in said population of cells; exposing said population of cells to a compound, or a mixture of compounds; determining the level of MMP1, MMP3, MMP8, MMP13, MMP14, and/or ADAMTS4 expression in response to IL-1 stimulation in said population of cells during or after exposure of said population of cells to the compound, or the mixture of compounds; and identifying the compound that decreases the expression of MMP1, MMP3, MMP8, MMP13, MMP14, and/or ADAMTS4 is predictive of a decrease in cartilage and/or ECM degradation. In a specific embodiment, the cartilage degrading enzyme measured in the method above is MMP13.

More particularly, the invention relates to a method for identifying an agent that reduces inflammation, the method comprising:

(a) contacting a population of cells with one or more compound(s) that exhibits binding affinity for a TARGET polypeptide, or fragment thereof, and
(b) measuring a compound-polypeptide property related to the inhibition of inflammation.

In one embodiment the compound-polypeptide property related to the inhibition of inflammation is the response of the cells to IL1 stimulation. In a further embodiment the agent is able to reduce the response of the cells to IL1 stimulation.

The invention also relates to a method for identifying a compound that decreases the expression and/or activity of any one of the polypeptides listed in Table 1, said method comprising the steps of: culturing a population of cells expressing said polypeptide, or a fragment, or a derivative thereof; determining a first level of expression and/or activity of said polypeptide; exposing said population of cells to a compound, or a mixture of compounds; determining the level of expression and/or activity of said polypeptide during or after exposure of said population of cells to the compound, or the mixture of compounds; and identifying the compound that decreases the expression and/or activity of said polypeptide. If the polypeptide activity is not readily measurable, the identification of the compound may benefit from an extra step comprising exposing said population of cells to an agonist of said polypeptide. Furthermore, the methods of the present invention may comprise the step of introducing a gene encoding any one of the polypeptides listed in Table 1, in said population of cells. For high-throughput purposes it may be beneficial to have the gene stably integrated in the genome of said cells.

In a preferred embodiment, the level of inhibition of cartilage and/or ECM degradation is determined by measuring the expression level of a marker gene, wherein a particular marker gene encodes MMP1, MMP3, MMP8, MMP13, MMP14, and/or ADAMTS4. In a specific embodiment, the expression and/or activity of MMP13 is measured. In a specific embodiment, the expression and/or activity of MMP13 is decreased.

In a particular embodiment of the invention, the TARGET polypeptide comprises an amino acid sequence selected from the group consisting of SEQ ID No: 22-42 as listed in Table 1. In an embodiment of the invention, the nucleic acid capable of encoding the TARGET polypeptide comprises a nucleic acid sequence selected from the group consisting of SEQ ID NO: 1-21 as listed in Table 1. Table 1 provides TARGET exemplary human nucleic acid and protein sequence, including recognized variants or isoforms where more than one accession number and SEQ ID NO: is indicated. Isoforms or variants of the TARGET(S) include nucleic acid or proteins with or utilizing alternate in frame exons, alternative splicing or splice variants, and alternative or premature termination variants.

TABLE 1

| TARGETS | | | | | | |
|---|---|---|---|---|---|---|
| Target Gene Symbol | GenBank Nucleic Acid Acc #: | SEQ ID NO: DNA | GenBank Protein Acc # | SEQ ID NO: Protein: | TARGET NAME | Class |
| MET | NM_000245 | 1 | NP_000236 | 22 | met proto-oncogene (hepatocyte growth factor receptor) | Kinase |
| STK32B | NM_018401 | 2 | NP_060871 | 23 | serine/threonine kinase 32B | Kinase |
| GPR34 | NM_005300 | 3 | NP_005291 | 24 | G protein-coupled | |
| | NM_001033513 | 4 | NP_001028685 | 25 | receptor 34 | GPCR |
| | NM_001033514 | 5 | NP_001028686 | 26 | | |
| GPR43 | NM_005306 | 6 | NP_005297 | 27 | G protein-coupled receptor 43 | GPCR |
| MAP2K2 | NM_030662 | 7 | NP_109587 | 28 | mitogen-activated protein kinase kinase 2 | Kinase |
| ADAMTS6 | NM_014273 | 8 | NP_922932 | 29 | a disintegrin-like and metalloprotease (reprolysin type) with thrombospondin type 1 motif, 6 | Protease |
| KCNN4 | NM_002250 | 9 | NP_002241 | 30 | potassium intermediate/small conductance calcium-activated channel, subfamily N, member 4 | Ion Channel |
| ADAM15 | NM_003815 | 10 | NP_003806 | 31 | a disintegrin and | |
| | NM_207191 | 11 | NP_997074 | 32 | metalloproteinase | |
| | NM_207194 | 12 | NP_997077 | 33 | domain 15 | Protease |
| | NM_207195 | 13 | NP_997078 | 34 | (metargidin) | |
| | NM_207196 | 14 | NP_997079 | 35 | | |
| | NM_207197 | 15 | NP_997080 | 36 | | |
| MAP4K1 | NM_007181 | 16 | NP_009112 | 37 | mitogen-activated protein kinase kinase kinase kinase 1 | Kinase |
| MC3R | NM_019888 | 17 | NP_063941 | 38 | melanocortin 3 receptor | GPCR |
| EPHA5 | NM_004439 | 18 | NP_004430 | 39 | EPH receptor A5 | Kinase |
| | NM_182472 | 19 | NP_872272 | 40 | | |
| CSNK1G2 | NM_001319 | 20 | NP_001310 | 41 | casein kinase 1, gamma 2 | Kinase |
| EDG4 | NM_004720 | 21 | NP_004711 | 42 | endothelial differentiation, lysophosphatidic acid G-protein-coupled receptor, 4 | GPCR |

The present invention provides in one particular embodiment methods for identifying novel compounds, wherein the polypeptide is a GPCR. If so, the expression and/or activity of said GPCR is preferably determined by measuring the level of a second messenger. Preferred second messengers are cyclic AMP, $Ca^{2+}$ or both. Typically, the level of the second messenger is determined with a reporter gene under the control of a promoter that is responsive to the second messenger, wherein it is preferred that the promoter is a cyclic AMP-responsive promoter, an NF-KB responsive promoter, or a NF-AT responsive promoter, and wherein the reporter gene is selected from the group consisting of: alkaline phosphatase, GFP, eGFP, dGFP, luciferase and β-galactosidase. Exemplary TARGETs which are GPCRs are listed in Table 1 and include GPR34, GPR43, MC3R and EDG4.

In another particular embodiment, the invention provides methods for identifying novel compounds, wherein the polypeptide is a kinase or a phosphatase. Preferably, the activity of said kinase or phosphatase is determined by measuring the level of phosphorylation of a substrate of said kinase or phosphatase. Exemplary TARGETS which are kinases are listed in Table 1 and include MET, STK32B, MAP2K2, MAP4K1, EPHA5, and CSNK1G2, Preferred TARGETS which are kinases are selected from the group consisting of STK32B, EPHA5 and CSNK1G2. Particularly preferred TARGETS which are kinases are EPHA5 and CSNK1G2.

In yet another particular embodiment, the invention provides methods for identifying novel compounds, wherein the polypeptide is a protease. Preferably, the activity of said protease is measured by determining the level of cleavage of a substrate of said protease. Exemplary TARGETS which are proteases are listed in Table 1 and include ADAMTS6, and ADAM15.

In yet another particular embodiment, the invention provides methods for identifying novel compounds, wherein the polypeptide is an ion channel. An exemplary TARGET which is an ion channel is listed in Table 1, KCNN4.

Methods for determining second messenger levels, use of the reporter genes and second-messenger responsive promoters as well as phosphatase assays and protease assays are well known in the art and not further elaborated upon herein.

In a preferred embodiment, the compound that inhibits the polypeptide exhibits a binding affinity to the polypeptide of at most 10 micromolar.

In a preferred embodiment of the invention, the polypeptide TARGET comprises an amino acid sequence selected from the group consisting of SEQ ID NO: 22-42 (Table 1).

Depending on the choice of the skilled artisan, the present assay method may be designed to function as a series of measurements, each of which is designed to determine whether the drug candidate compound is indeed acting on the polypeptide to thereby inhibit the degradation of cartilage and/or ECM or to inhibit inflammation. For example, an assay designed to determine the binding affinity of a compound to the polypeptide, or fragment thereof, may be necessary, but not sufficient, to ascertain whether the test compound would be useful for decreasing ECM and/or cartilage degradation when administered to a subject, or alternatively to ascertain whether the test compound would be useful for decreasing inflammation. Nonetheless, such binding information would be useful in identifying a set of test compounds for use in an assay that would measure a different property, further up the biochemical pathway, such as the MMP13 assay described below or an assay using cartilage explants. Such second assay may be designed to confirm that the test compound, having binding affinity for the polypeptide, actually decreases the degradation of cartilage and/or ECM or reduces inflammation, in vitro or in vivo.

Suitable controls should always be in place to insure against false positive readings. In a particular embodiment of the present invention the screening method comprises the additional step of comparing the compound to a suitable control. In one embodiment, the control may be a cell or a sample that has not been in contact with the test compound. In an alternative embodiment, the control may be a cell that does not express the TARGET; for example in one aspect of such an embodiment the test cell may naturally express the TARGET and the control cell may have been contacted with an agent, e.g. an siRNA, which inhibits or prevents expression of the TARGET. Alternatively, in another aspect of such an embodiment, the cell in its native state does not express the TARGET and the test cell has been engineered so as to express the TARGET, so that in this embodiment, the control could be the untransformed native cell. The control may also or alternatively utilize a known mediator of inflammation or ECM and/or cartilage degradation, such as cells treated with cytokines e.g. IL1, TNFα, OSM, or other inflammatory mediators (e.g. LPA or reactive oxygen species), prostaglandins, or leukotrienes. Whilst exemplary controls are described herein, this should not be taken as limiting; it is within the scope of a person of skill in the art to select appropriate controls for the experimental conditions being used.

The order of taking these measurements is not believed to be critical to the practice of the present invention, which may be practiced in any order. For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide. However, for the present assay to be meaningful to the ultimate use of the drug candidate compounds, a direct measurement of inflammation, ECM degradation and/or cartilage degradation will be valuable. Validation studies including controls, and measurements of binding affinity to the polypeptides of the invention are nonetheless useful in identifying a compound useful in any therapeutic or diagnostic application.

Analogous approaches based on art-recognized methods and assays may be applicable with respect to the TARGETS and compounds in any of various disease(s) characterized by cartilage and/or ECM degradation. An assay or assays may be designed to confirm that the test compound, having binding affinity for the TARGET, inhibits the degradation of cartilage and/or ECM. In one such method the expression and/or activity of a cartilage degradative enzyme such as a collagenase is measured. In one particular such method the expression and/or activity of MMP1, MMP3, MMP8, MMP13, MMP14, and/or ADAMTS4 is measured. In one particular such method the expression and/or activity of MMP13 is measured.

Analogous approaches based on art-recognized methods and assays may be applicable with respect to the TARGETS and compounds in any of various disease(s) characterized by inflammation. An assay or assays may be designed to confirm that the test compound, having binding affinity for the TARGET, inhibits inflammation. In one such method the expression and/or activity of a cartilage degradative enzyme such as a collagenase is measured. In one particular such method the expression and/or activity of MMP1, MMP3, MMP8, MMP13, MMP14, and/or ADAMTS4 is measured. In one particular such method the expression and/or activity of MMP13 is measured. In an alternative method the level of one or more inflammatory cytokines selected from IL-1b, IL-6, IL-8, IL-11, TNFα and/or LIF are measured.

The present assay method may be practiced in vitro, using one or more of the TARGET proteins, or fragments thereof, including monomers, portions or subunits of polymeric proteins, peptides, oligopeptides and enzymatically active portions thereof.

The binding affinity of the compound with the polypeptide TARGET can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, i.e. in the range of 100 nM to 1 pM; a moderate to low affinity binding relates to a high Kd, $IC_{50}$ and $EC_{50}$ values, i.e. in the micromolar range.

The present assay method may also be practiced in a cellular assay, A host cell expressing TARGET can be a cell with endogenous expression or a cell over-expressing the TARGET e.g. by transduction. When the endogenous expression of the polypeptide is not sufficient to determine a baseline that can easily be measured, one may use using host cells that over-express TARGET. Over-expression has the advantage that the level of the TARGET substrate end products is higher than the activity level by endogenous expression. Accordingly, measuring such levels using presently available techniques is easier. In one such cellular assay, the biological activity of TARGET may be measured by following the production of cartilage component synthesis.

One embodiment of the present method for identifying a compound that inhibits inflammation, ECM and/or cartilage degradation comprises culturing a population of cells expressing a TARGET polypeptide, or a fragment or derivative thereof; determining a first level of MMP1, MMP3, MMP8, MMP13, MMP14, and/or ADAMTS4, in particular MMP13, expression and/or activity in said population of cells on activation of the population of cells (e.g. by stimulation using IL1); exposing said population of cells to a compound, or a mixture of compounds; determining a second level of expression or activity of MMP1, MMP3, MMP8, MMP13, MMP14, and/or ADAMTS4, in particular MMP13, in said population of cells after the same activation, during or after exposure of said population of cells to said compound, or the mixture of said compounds; and identifying the compound(s) that suppress the expression and/or activity of MMP1, MMP3, MMP8, MMP13, MMP14, and/or ADAMTS4, in particular MMP13. In a specific embodiment, the cells are chondrocytes. In a specific embodiment the cells are mammalian cells. In a specific embodiment the cells are human cells.

The expression and/or activity of MMP1, MMP3, MMP8, MMP13, MMP14, and/or ADAMTS4 can be determined by methods known in the art such as the methods as described herein.

The present inventors identified TARGET genes involved in the inhibition of inflammation, cartilage and/or ECM degradation by using a 'knock-down' library. This type of library is a screen in which siRNA molecules are transduced into cells by recombinant adenoviruses, which siRNA molecules inhibit or repress the expression of a specific gene as well as expression and activity of the corresponding gene product in a cell. Each siRNA in a viral vector corresponds to a specific natural gene. By identifying a siRNA that inhibits the degradation of cartilage, as measured by suppression of the expression of MMP13, a direct correlation can be drawn between the specific gene expression and the pathway for inhibiting inflammation, cartilage and/or ECM degradation. The TARGET genes identified using the knock-down library (the protein expression products thereof herein referred to as "TARGET" polypeptides) are then used in the present inventive method for identifying compounds that can be used in the treatment of diseases associated with the inflammation or the degradation of ECM and/or cartilage. Indeed, shRNA compounds comprising the sequences listed in Table 2 (SEQ ID NOs: 43-57) inhibit the expression and/or activity of these TARGET genes and decrease the expression of MMP13, confirming the role of the TARGETS in the pathway leading to the degradation of cartilage and/or ECM or inflammation.

TABLE 2

KD TARGET sequences useful in the practice of the present expression-inhibitory agent invention

| Hit ID | Target Gene Symbol | KD Target Sequence | KD SEQ ID No: |
|---|---|---|---|
| H54-001 | MET | CATGGCTCTAGTTGTCGAC | 43 |
| H54-016 | STK32B | TATCCTGCTGGATGAACAC | 44 |
| H54-023 | GPR34 | GTAGGAGTGAAAGCACTTC | 45 |
| H54-024 | GPR43 | TACTTGAACACGACTGAGC | 46 |
| H54-025 | GPR43 | CTGCTACGAGAACTTCACC | 47 |
| H54-044 | MAP2K2 | GATGCTCACAAACCACACC | 48 |
| H54-058 | ADAMTS6 | CTTTCAGCCTATGGCAAGC | 49 |
| H54-094 | KCNN4 | ATGATCCTGTATGACCTGC | 50 |
| H54-127 | ADAM15 | TCCAAGATCTCCACCTGCC | 51 |
| H54-305 | ADAM15 | GTTGGAGCTGGACGGTGAC | 52 |
| H54-140 | MAP4K1 | GATCCAGGACACCAAAGGC | 53 |
| H54-165 | MC3R | CATCTTCGACTCCATGATC | 54 |
| H54-257 | EPHA5 | AGATCAGTAGGTGAATGGC | 55 |
| H54-269 | CSNK1G2 | ACCAGGCGTTGAACTCCAC | 56 |
| H54-340 | EDG4 | TCTGCTGGTCATAGCAGCC | 57 |

The present invention further relates to a method for identifying a compound that reduces inflammation and/or the degradation of cartilage and/or ECM, comprising:

(a) contacting a compound with a polypeptide comprising an amino acid sequence selected from the group consisting of SEQ ID NO: 22-42;

(b) determining the binding affinity of the compound to the polypeptide;

(c) contacting a population of mammalian cells expressing said polypeptide with the compound that exhibits a binding affinity of at least 10 micromolar; and (d) identifying a compound that reduces response to IL-1 or that reduces the synthesis of enzymes that act to degrade ECM and/or cartilage and/or related markers that indicate the presence of said enzymes.

In one aspect, the assay method includes contacting cells expressing said polypeptide with the compound that exhibits a binding affinity in the micromolar range. In an aspect, the binding affinity exhibited is at least 10 micromolar. In an aspect, the binding affinity is at least 1 micromolar. In an aspect, the binding affinity is at least 500 nanomolar.

The assay method may be based on the particular expression or activity of the TARGET polypeptide, including but not limited to an enzyme activity. Assays for the protease TARGETs ADAMTS6 (SEQ ID NO: 29) or ADAM15 (SEQ ID NOs: 31, 32, 33, 34, 35, or 36) may be based on protease activity or expression. Assays for the kinase TARGETs identified as MET (SEQ ID NO: 22), STK32B (SEQ ID NO: 23), MAP2K2 (SEQ ID NO: 28), MAP4K1 (SEQ ID NO: 37), EPHA5 (SEQ ID NOs: 39 or 40) and CSNK1G2 (SEQ ID NO: 41), may be based on kinase or phosphatase activity or expression, including but not limited to phosphorylation or dephosphorylation of a target protein. Assays for the GPCR TARGETs identified as GPR34 (SEQ ID NOs: 24, 25 or 26), GPR43 (SEQ ID NO: 27) MC3R (SEQ ID NO: 39) and EDG4 (SEQ ID NO: 42), may be based on GPCR activity or expression, including downstream mediators or activators. Assays for the ion channel TARGET identified as KCNN4 (SEQ ID NO: 30) may use techniques well known to those of skill in the art including classical patch clamping, high-throughput fluorescence based or tracer based assays which measure the ability of a compound to open or close an ion channel thereby changing the concentration of fluorescent dyes or tracers across a membrane or within a cell. The measurable phenomenon, activity or property may be selected or chosen by the skilled artisan. The person of ordinary skill in the art may select from any of a number of assay formats, systems or design one using his knowledge and expertise in the art.

Table 1 lists the TARGETS identified using applicants' knock-down library in the MMP13 assay described below, including the class of polypeptides identified. TARGETS have been identified in polypeptide classes including kinase, phophatase, protease, GPCR, and ion channel, for instance. Specific methods to determine the activity of a kinase by measuring the phosphorylation of a substrate by the kinase, which measurements are performed in the presence or absence of a compound, are well known in the art.

Specific methods to determine the inhibition by a compound by measuring the cleavage of the substrate by the polypeptide, which is a protease, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

Ion channels are membrane protein complexes and their function is to facilitate the diffusion of ions across biological membranes. Membranes, or phospholipid bilayers, build a hydrophobic, low dielectric barrier to hydrophilic and charged molecules. Ion channels provide a high conducting, hydrophilic pathway across the hydrophobic interior of the membrane. The activity of an ion channel can be measured using classical patch clamping. High-throughput fluorescence-based or tracer-based assays are also widely available to measure ion channel activity. These fluorescent-based assays screen compounds on the basis of their ability to either open or close an ion channel thereby changing the concentration of specific fluorescent dyes across a membrane. In the case of the tracer based assay, the changes in concentration of the tracer within and outside the cell are measured by radioactivity measurement or gas absorption spectrometry.

G-protein coupled receptors (GPCR) are capable of activating an effector protein, resulting in changes in second messenger levels in the cell. The activity of a GPCR can be determined by measuring the activity level of such second messengers. Two exemplary important and useful second messengers in the cell are cyclic AMP (cAMP) and $Ca^{2+}$. The second messenger activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

It should be understood that the cells expressing the polypeptides may be cells which naturally express the polypeptides, or the cells may be transfected to express the polypeptides, as described above. Also, the cells may be transduced to overexpress the polypeptide, or may be transfected to express a non-endogenous form of the polypeptide, which can be differentially assayed or assessed.

In one particular embodiment the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of the release of inflammatory mediators. In a particular embodiment, the cells used in the present method are mammalian NHACs. The NHACs, in the assay contemplated, may be activated (e.g. by stimulation with IL1).

A method for identifying a compound that inhibits inflammation or cartilage and/or ECM degradation, comprising:

(a) contacting a compound with a polypeptide comprising an amino acid sequence selected from the group consisting of SEQ ID NO: 22-42, and fragments thereof; and (b) measuring a compound-polypeptide property related to cartilage degradation.

In one embodiment of the present invention the method relates to identifying a compound that inhibits the catabolic processes of chondrocytes.

In one embodiment of the present invention the compound-polypeptide property related to inflammation or cartilage and/or ECM degradation is binding affinity.

In one embodiment the compound-polypeptide property related to inflammation or cartilage and/or ECM degradation is the inhibition of MMP1, MMP3, MMP8, MMP13, MMP14, and/or ADAMTS4 expression and/or activity.

In one embodiment the compound-polypeptide property related to inflammation or cartilage and/or ECM degradation is the inhibition of MMP13 expression and/or activity.

In one embodiment the compound-polypeptide property related to inflammation or cartilage and/or ECM degradation is the expression of inflammatory cytokines such as IL-1b, IL-6, IL-8, IL-11, TNFα and/or LIF.

In one embodiment of the present invention the compound-polypeptide property related to inflammation or cartilage and/or ECM degradation is the activity of said polypeptide. In particular, in one embodiment the compound inhibits the activity of said polypeptide.

In one embodiment of the present invention the compound-polypeptide property related to inflammation or cartilage and/or ECM degradation is the expression of said polypeptide. In particular, in one embodiment the compound inhibits the expression of said polypeptide.

The present invention further relates to a method for identifying a compound that inhibits inflammation or cartilage and/or ECM degradation, wherein said compound exhibits at least a moderate binding affinity to an amino acid selected from the group of SEQ ID NOS: 22-42, said method comprising:

a) contacting a compound with a population of mammalian cells expressing a polypeptide comprising an amino acid sequence selected from the group consisting of SEQ ID NOS: 22-42, wherein the cells have been activated;

b) determining the expression of MMP13 from said cells; and c) identifying the compound that inhibits inflammation or cartilage and/or ECM degradation as the compound which suppresses the release of MMP13 from the cells.

In one such method the cells are activated by being contacted with pro-inflammatory factors. In a specific embodiment of the method the pro-inflammatory factors are selected from TNF-alpha, IL-1, OSM (oncostatin M), IL6, endothelin, bradykinin, LPA, leukotrienes, prostaglandins, LPS (lipo poly saccharides) or other TLR ligands, or combinations thereof.

In one such method, the compound exhibits a binding affinity to an amino acid selected from the group of SEQ ID NOS: 22-42 of at least 10 micromolar.

The present invention further relates to a method for identifying a compound that inhibits inflammation or cartilage and/or ECM degradation, said method comprising:

a) contacting a compound with a polypeptide comprising an amino acid sequence selected from the group consisting of SEQ ID NO: 22-42;

b) determining the binding affinity of the compound to the polypeptide;

c) contacting a population of mammalian cells expressing said polypeptide with the compound that exhibits a binding affinity of at least 10 micromolar; and d) identifying the compound that inhibits inflammation or cartilage and/or ECM degradation.

The present invention further relates to a method for identifying a compound that inhibits inflammation or cartilage and/or ECM degradation said method comprising:

a) contacting a compound with a polypeptide comprising an amino acid sequence selected from the group consisting of SEQ ID NO: 22-42;

b) determining the ability of the compound to inhibit the expression or activity of the polypeptide;

c) contacting a population of mammalian cells expressing said polypeptide with the compound that significantly inhibits the expression or activity of the polypeptide; and d) identifying the compound that inhibits inflammation or cartilage and/or ECM degradation.

In a particular aspect of the present invention the methods described above include the additional step of comparing the compound to be tested to a control, where the control is a population of cells that have not been contacted with the test compound.

In a particular aspect of the present invention the methods described above include the additional step of comparing the compound to be tested to a control, where the control is a population of cells that do not express said polypeptide.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich, BioFocus DPI) or natural compound libraries (Specs, TimTec, BioFocus DPI).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al., (2001)). Peptides comprise another preferred class of drug candidate compounds. Peptides may be excellent drug candidates and there are multiple examples of commercially valuable peptides such as fertility hormones and platelet aggregation inhibitors. Natural products are another preferred class of drug candidate compound. Such compounds are found in and extracted from natural sources, and which may thereafter be synthesized. The lipids are another preferred class of drug candidate compound.

Another preferred class of drug candidate compounds is an antibody. The present invention also provides antibodies directed against a TARGET. These antibodies may be endogenously produced to bind to the TARGET within the cell, or added to the tissue to bind to TARGET polypeptide present outside the cell. These antibodies may be monoclonal antibodies or polyclonal antibodies. The present invention includes chimeric, single chain, domain antibodies, camelid antibodies, and humanized antibodies, as well as FAb fragments and the products of a FAb expression library, and Fv fragments and the products of an Fv expression library. The antibodies may be neutralizing antibodies or antibodies that inhibit the activity of the TARGET or that block or inhibit binding of a ligand to the TARGET or of the TARGET to another protein.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, 1994). Transgenic animals may be used to express humanized antibodies.

Human antibodies can also be produced using various techniques known in the art, including phage display libraries (Hoogenboom and Winter, 1991; Marks et al., 1991). The techniques of Cole, et al. and Boerner, et al. are also available for the preparation of human monoclonal antibodies (Cole, et al., (1985); Boerner, et al., 1991) Techniques known in the art for the production of single chain antibodies can be adapted to produce single chain antibodies to the TARGET polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET; the other one is for another domain of the same or different TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983)). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker et al., 1991.

According to another preferred embodiment, the assay method uses a drug candidate compound identified as having a binding affinity for a TARGET, and/or has already been identified as having down-regulating activity such as antagonist activity vis-à-vis one or more TARGET.

In vivo animal models of arthritis or osteoarthritis or of inflammation or inflammatory diseases may be utilized by the skilled artisan to further or additionally screen, assess, and/or verify the agents or compounds identified in the present invention, including further assessing TARGET modulation in vivo. Such animal models include, but are not limited to, ulcerative colitis models, multiple sclerosis models (including EAE, lysolecithin-induced), arthritis models, allergic asthma models, airway inflammation models, and acute inflammation models. Osteoarthritis models include for example experimental osteoarthritis induced in rabbits after sectioning of the knee anterior cruciate ligament and in rats after tear of the medial collateral ligament.

The present invention further relates to a method for inducing anabolic stimulation of chondrocytes or reducing chondrocyte degradation comprising contacting said cells with an expression inhibitory agent comprising a polynucleotide sequence that complements at least about 17 nucleotides of the polyribonucleotide comprising a nucleotide sequence selected from the group consisting of SEQ ID NO: 1-21. In a preferred embodiment the expression-inhibitory agent comprises a polynucleotide sequence that complements a nucleotide sequence selected from the group consisting of SEQ ID NO: 43-57.

Another aspect of the present invention relates to a method for inhibiting inflammation or cartilage and/or ECM degradation, comprising contacting said cell with an expression-inhibiting agent that inhibits the translation in the cell of a polyribonucleotide encoding a TARGET polypeptide. A particular embodiment relates to a composition comprising a polynucleotide including at least one antisense strand that functions to pair the agent with the TARGET mRNA, and thereby down-regulate or block the expression of TARGET polypeptide. The inhibitory agent preferably comprises antisense polynucleotide, a ribozyme, or a small interfering RNA (siRNA), wherein said agent comprises a nucleic acid sequence complementary to, or engineered from, a naturally-occurring polynucleotide sequence encoding a portion of a polypeptide comprising an amino acid sequence selected from the group consisting of SEQ ID NO: 22-42. In a preferred embodiment the expression-inhibiting agent is complementary to a polynucleotide sequence selected from the group consisting of SEQ ID NO: 1-21. In an especially preferred embodiment the expression-inhibiting agent is complementary to a polynucleotide sequence selected from the group consisting of SEQ ID NO: 43-57.

An embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 22-42, a small interfering RNA (siRNA, preferably shRNA) that is sufficiently complementary to a portion of the polyribonucleotide coding for SEQ ID NO: 22-42, such that the siRNA, preferably shRNA, interferes with the translation of the TARGET polyribonucleotide to the TARGET polypeptide. Preferably the expression-inhibiting agent is an antisense RNA, ribozyme, antisense oligodeoxynucleotide, or siRNA, preferably shRNA, complementary to a nucleotide sequence selected from the group consisting of SEQ ID NO: 1-21. In an especially preferred embodiment the expression-inhibiting agent is complementary to a polynucleotide sequence selected from the group consisting of SEQ ID NO: 43-57.

A special embodiment of the present invention relates to a method wherein the expression-inhibiting agent is a nucleic acid expressing the antisense RNA, antisense oligodeoxynucleotide (ODN), a ribozyme that cleaves the polyribonucleotide coding for SEQ ID NO: 22-42, a small interfering RNA (siRNA, preferably shRNA) that is sufficiently complementary to a portion of the polyribonucleotide coding for SEQ ID NO: 22-42, such that the siRNA, preferably shRNA, interferes with the translation of the TARGET polyribonucleotide to the TARGET polypeptide. Preferably the nucleotide sequence is complementary to a polynucleotide selected from the group consisting of SEQ ID NO: 1-21. In an especially preferred embodiment nucleotide sequence is complementary to a polynucleotide selected from the group consisting of SEQ ID NO: 43-57.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-21. For example, an antisense nucleic acid (e.g. DNA) may be introduced into cells in vitro, or administered to a subject in vivo, as gene therapy to inhibit cellular expression of nucleic acids comprising SEQ ID NO: 1-21. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides complementary to a nucleic acid sequence selected from the sequences of SEQ ID NO: 1-21.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RN202-315NA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or *Neurospora* VS RNA motif. Ribozymes possessing a hammerhead or hairpin structure are readily prepared since these catalytic RNA molecules can be expressed within cells from eukaryotic promoters (Chen, et al., 1992). A ribozyme of the present invention can be expressed in eukaryotic cells from the appropriate DNA vector. If desired, the activity of the ribozyme may be augmented by its release from the primary transcript by a second ribozyme (Ventura, et al., 1993).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, 1993). It has been demonstrated that ribozymes expressed from these promoters can function in mammalian cells (Kashani-Sabet, et al., 1992).

A particularly preferred inhibitory agent is a small interfering RNA (siRNA, preferably shRNA). siRNA, preferably shRNA, mediates the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences described in SEQ ID NO: 1-21, preferably from the group of sequences described in SEQ ID No: 43-57, and an antisense strand of 17-23 nucleotides complementary to the sense strand. Exemplary sequences are described as sequences complementary to SEQ ID NO: 43-57. The most preferred siRNA comprises sense and anti-sense strands that are 100 percent complementary to each other and the TARGET polynucleotide sequence. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 or 12 nucleotides long. In a specific embodiment the linker sequence is UUGCUAUA. In an alternative specific embodiment the linker sequence is GUUUGCUAUAAC (SEQ ID NO: 58). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO 2004/094636, and US 2003/0198627, are hereby incorporated by reference).

The present invention also relates to compositions, and methods using said compositions, comprising a DNA expression vector capable of expressing a polynucleotide capable of inhibiting the degradation of cartilage and described hereinabove as an expression inhibition agent.

A special aspect of these compositions and methods relates to the down-regulation or blocking of the expression of a TARGET polypeptide by the induced expression of a polynucleotide encoding an intracellular binding protein that is capable of selectively interacting with the TARGET polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the TARGET polypeptide of SEQ ID NO: 22-42. More preferably, the intracellular binding protein is a single chain antibody.

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 22-42, and a small interfering RNA (siRNA) that is sufficiently homologous to a portion of the polyribonucleotide coding for SEQ ID NO: 22-42, such that the siRNA interferes with the translation of the TARGET polyribonucleotide to the TARGET polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in TARGET cells.

Preferably, the viral vectors used in the methods of the present invention are replication defective. Such replication defective vectors will usually lack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the TARGET cell population that an adenoviral capsid of the invention can enter in a preferred embodiment, the vehicle includes adenoviral fiber proteins from at least two adenoviruses. Preferred adenoviral fiber protein sequences are serotype 5, 17, 45 and 51. Techniques or construction and expression of these chimeric vectors are disclosed in US 2003/0180258 and US 2004/0071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to TARGET the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_l$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315:338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g. WO 95/21931), peptides derived from DNA binding proteins (e.g. WO 96/25508), or a cationic polymer (e.g. WO 95/21931).

It is also possible to introduce a DNA vector in vivo as a naked DNA plasmid (see U.S. Pat. No. 5,693,622, U.S. Pat. No. 5,589,466 and U.S. Pat. No. 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, cartilage degradation-inhibiting compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET; a nucleic acid would be able to replicate, translate a message, or hybridize to a complementary mRNA of a TARGET; a vector would be able to transfect a TARGET cell and expression the antisense, antibody, ribozyme or siRNA as described hereinabove; an antibody would bind a TARGET polypeptide domain.

A preferred biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particularly preferred embodiment of the present composition invention is a cartilage formation-enhancing pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a condition involving inflammation or cartilage and/or ECM degradation, or a susceptibility to the condition, comprising an effective cartilage formation-enhancing amount of a TARGET antagonist or inverse agonist, its pharmaceutically acceptable salts, hydrates, solvates, or prodrugs thereof in admixture with a pharmaceutically acceptable carrier. In one aspect the condition involves a systemic or local decrease in mean cartilage thickness.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the preferred embodiment, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J). A hydrogel is defined as a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions, that have charged side groups, or a monovalent ionic salt thereof. The composition medium may be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to TARGET tissues, complexed with cationic lipids, packaged within liposomes, or delivered to TARGET cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The present invention also provides methods of enhancing cartilage formation, which comprise the administration to said subject a therapeutically effective amount of an expression-inhibiting agent of the invention. A further aspect of the invention relates to a method of treating or preventing a disease involving chondrocyte anabolic stimulation, comprising administering to said subject a cartilage formation-enhancing pharmaceutical composition as described herein.

Examples of diseases involving degradation of ECM that are treatable using the means and methods of the present invention include, but are not limited to psoriatic arthritis, juvenile arthritis, early arthritis, reactive arthritis, osteoarthritis, ankylosing spondylitis. osteoporosis, muskulo skeletal diseases such as tendinitis and periodontal disease, cancer metastasis, airway diseases (COPD, asthma), renal and liver fibrosis, cardio-vascular diseases such as atherosclerosis and heart failure, and neurological diseases such as neuroinflammation and multiple sclerosis.

Examples of diseases involving degradation of cartilage that are treatable using the means and methods of the present invention include, but are not limited to osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease, and Handigodu disease; degeneration resulting from fibromyalgia, systemic lupus erythematosus, scleroderma, and ankylosing spondylitis. Furthermore, people suffering from congenital cartilage malformations, including hereditary chondrolysis, chondrodysplasias and pseudoachondrodysplasias, are likely to benefit from programs that result in anabolic stimulation of chondrocytes, and these diseases therefore may also be treated by using the methods and means of the present invention. Non-limiting examples of congenital cartilage malformation related diseases are microtia, anotia, and metaphyseal chondrodysplasia.

In addition, as the identified targets do also inhibit IL-1 signal transduction, inhibitors of these targets could be of use in the treatment of inflammatory diseases. Examples of diseases involving inflammation that are treatable using the means and methods of the present invention include but are not limited to allergic airways disease (e.g. asthma, rhinitis), autoimmune diseases, transplant rejection, Crohn's disease, rheumatoid arthritis, psoriasis, juvenile idiopathic arthritis, colitis, and inflammatory bowel diseases.

In one aspect the present invention provides methods of preventing and/or treating disorders involving inflammation, ECM degradation and/or cartilage degradation, said methods comprising administering to a subject a therapeutically effective amount of an agent as disclosed herein. In a particular embodiment, the agent is selected from an expression-inhibiting agent and an antibody. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

The invention also relates to the use of an agent as described above for the preparation of a medicament for treating or preventing a disease involving inflammation, ECM degradation and/or cartilage degradation. In a particular embodiment, the agent is selected from an expression-inhibiting agent and an antibody. In a particular embodiment of the present invention the disease is selected from osteoarthritis, rheumatoid arthritis, allergic airways disease (e.g. asthma, rhinitis), and autoimmune diseases. In a particular embodiment the disorder is osteoarthritis.

The present invention also provides a method of treating and/or preventing a disease involving inflammation, ECM degradation and/or cartilage degradation said method comprising administering, to a subject suffering from, or susceptible to, a disease involving cartilage degradation, a pharmaceutical composition or compound as described herein, particularly a therapeutically effective amount of an agent which inhibits the expression or activity of a TARGET as identified herein. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

The invention also relates to an agent or a pharmaceutical composition as described above for use in the treatment and/or prevention of a disease involving inflammation, ECM degradation and/or cartilage degradation. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

Administration of the agent or pharmaceutical composition of the present invention to the subject patient includes both self-administration and administration by another person. The patient may be in need of treatment for an existing disease or medical condition, or may desire prophylactic treatment to prevent or reduce the risk for diseases and medical conditions characterized by cartilage degradation. The agent of the present invention may be delivered to the subject patient orally, transdermally, via inhalation, injection, nasally, rectally or via a sustained release formulation.

Still another aspect of the invention relates to a method for diagnosing a pathological condition involving inflammation, ECM degradation and/or cartilage degradation, comprising determining the amount of a polypeptide comprising an amino acid sequence selected from the group consisting of SEQ ID NO: 22-42 in a biological sample, and comparing the amount with the amount of the polypeptide in a healthy subject, wherein an increase of the amount of polypeptide compared to the healthy subject is indicative of the presence of the pathological condition. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

Still another aspect of the invention relates to a method for diagnosing a pathological condition involving inflammation, ECM degradation and/or cartilage degradation, comprising determining the activity of a polypeptide comprising an amino acid sequence selected from the group consisting of SEQ ID NO: 22-42 in a biological sample, and comparing the activity with the activity of the polypeptide in a healthy subject, wherein an increase of the activity of polypeptide compared to the healthy subject is indicative of the presence of the pathological condition. Clearly, the activity and/or expression levels of the target genes as disclosed herein may have an effect on anabolic stimulation of chondrocytes. It remains to be determined to what level the activity should be elevated to diagnose for the disease. However, by comparing levels found in patients, individuals without symptoms and clearly healthy individuals the skilled person may easily determine these relevant levels. Since the skilled person is now aware which polypeptides should be monitored, the present invention provides novel tools for test assays for such diagnostics. A prominent disease that may be controlled, checked and diagnosed by using the knowledge provided by the present invention is osteoarthritis. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

Still another aspect of the invention relates to a method for diagnosing a pathological condition involving inflammation, ECM degradation and/or cartilage degradation, comprising determining the nucleic acid sequence of at least one of the genes of SEQ ID NO: 1-21 within the genomic DNA of a subject; comparing the sequence with the nucleic acid sequence obtained from a database and/or a healthy subject; and identifying any difference(s) related to the onset or prevalence of the pathological conditions disclosed herein. Such differences may be further checked in in vitro assays applying similar marker genes as disclosed herein. Such assays will reveal the role of the gene or its encoded polypeptide in anabolic stimulation processes of chondrocytes. If such mutations are identified this knowledge can be further exploited in test-kits for diagnosis of similar diseases. In a particular embodiment the disorder is selected from osteoarthritis, rheumatoid arthritis, allergic airways disease (e.g. asthma, rhinitis), and autoimmune diseases. In a particular embodiment the disorder is osteoarthritis.

The polypeptides or the polynucleotides employed in the methods of the present invention may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding of) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., ($^{35}$S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

Another embodiment of the present invention relates to a method for the use of compounds which are able to ameliorate or to stabilize the properties of chondrocytes, chondrocyte progenitors, or mesenchymal stem cells used for autologous cell or cartilage transplantation, either during ex vivo culturing or after implantation. This amelioration can be the result of a reduced level of ECM and/or cartilage degrading proteases in or around the implant. For example a candidate compound may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The rate of ECM and/or cartilage degradation can typically be measured by determining the deposition of cartilage, or cartilage components, or cartilage-containing extracellular matrix produced by the chondrocytes, in the medium. A cell-based ELISA, enzymatic assays, or other general techniques known in the art can be used to measure cartilage components, like the ones described in Walsh G., Proteins: Biotechnology and Biochemistry. John Wiley and Sons, 2001.

The invention is further illustrated in the following figures and examples.

EXAMPLES

Example 1: MMP13 Assay with NHACs

As described in the introduction, MMP13 has been identified in the osteoarthritis literature as one of the key players involved in catabolic events leading to the degradation of cartilage in the affected joints of osteoarthritic patients. Therefore, it was decided to initiate a functional genomics effort in order to identify factors that modulate the expression of MMP13 in primary human chondrocytes activated with a disease relevant trigger. This assay is further referred to herein as the "MMP13 assay". The factors identified in this assay can be used as the basis for the development of novel therapies for osteoarthritis.

The MMP13 assay that has been developed for the screening of the SilenceSelect collection has the following distinctive features:

- The assay is run with primary human articular chondrocytes, but with minimal adaptations, could be used for any other source of primary chondrocytes, chondrocyte progenitors, or chondrocytic cell lines, or any cell that is capable of producing MMP13.
- The assay is run such that the primary human chondrocytes used are in an environment that resembles their normal environment (the cartilage matrix) as much as possible. The cells are grown in a three-dimensional culture, avoiding cell adhesion to the culture vessel.
- The assay has been optimized for use with arrayed adenoviral collections for functional genomics purposes.
- With minimal adaptations, the assay can also be used to screen compounds or compound collections
- The assay can be run in high throughput mode.

The MMP13 assay with normal human articular chondrocytes (NHACs) is described in more detail below. First, the protocol of the MMP13 ELISA that has been developed is described in section 1. Then the culture and maintenance of the primary chondrocytes is described in section 2. The screening protocol of the MMP13 assay with NHACs is described in section 3. The composition and performance of the control plate is shown in section 4. An example of the performance of the screening of the SilenceSelect collection is given in section 5.

The MMP13 assay in NHACs has been screened against an arrayed collection of 10946 different recombinant adenoviruses mediating the expression of shRNA's in NHACs. These shRNA's cause a reduction in expression levels of genes that contain homologous sequences by a mechanism known as RNA interference (RNAi). The 10946 Ad-siRNA's contained in the arrayed collection do target 6308 different transcripts. On average, every transcript is targeted by 2 to 3 independent, different Ad-siRNA's. The principle of the screening is illustrated in FIG. 1 and described in detail below.

1.1 MMP13 ELISA Protocol

Various antibodies and substrates were tested in order to develop an ELISA with sufficient sensitivity to detect the MMP13 amounts produced by cultured NHACs. A 384-well format ELISA for measurement of MMP13 was developed. Various primary antibodies were tested, as well as various ELISA protocols leading to the following validated protocol for measurement of MMP13 levels in 384 well plates. Black maxi sorb 384 well plates (Nunc 460518) are coated with 5 μg/mL anti-MMP13 antibody MAB511 (R&D Systems). The antibody is diluted in carbonate-bicarbonate coating buffer (1.59 g $Na_2CO_3$ (Sigma S-7795) and 2.93 g $NaHCO_3$ (Sigma S-5761) in 1 L milliQ, adjusted to pH 9.6). After overnight incubation at 4° C., plates are washed three times with 100 μL PBST (80 g NaCl, 2 g KCl (Sigma), 11.5 g $Na_2HPO_4.7H_2O$ and 2 g $KH_2PO_4$ in 10 L milliQ; pH 7.4+0.05% Tween-20 (Sigma)) and blocked with 100 μL/well blocking buffer (5% non fat dry milk in PBS). After 2 hrs of incubation at room temperature, plates are washed three times with 100 μL PBST. The PBST is then removed and 35 μL of sample is transferred to the ELISA plates. After overnight incubation at 4° C., plates are washed three times with PBST and incubated for 1 hr at 37° C. with 35 μL/well 1.5 mM APMA. A 10 mM APMA stock solution (prepared one day before) is stored at 4° C. (35.18 mg APMA (Sigma A-9563) in 10 mL 0.1M NaOH (Merck 1.06469.1000)). The 10 mM APMA stock solution is diluted to 1.5 mM in APMA buffer (10×APMA buffer: 500 mM Tris (Roche 708976), 50 mM $CaCl_2$ (Sigma C-5080), 500 μM $ZnCl_2$ (Sigma Z-0173), 1.5 M NaCl (Calbiochem 567441), 0.5% Brij35 (Sigma 430 AG-6) and adjust to pH 7.0). After activation of MMP13 by APMA, plates are washed again three times with 100 μL PBST/well. OmniMMP Fluorescent substrate (Biomol P-126) is dissolved in OmniMMP buffer (10× OmniMMP buffer: 500 mM Hepes (Sigma H4034), 100 mM $CaCl_2$ (Sigma C5080), 0.5% Brij35 (Sigma 430 AG-6; adjusted to pH 7.0) to a final concentration of 0.01 mM. 35 μL of this substrate is added to each well. After an overnight incubation at 37° C., the active MMP13 in the sample has cleaved the substrate and released fluorescence. Readout is performed on the EnVision (Perkin Elmer) using 320 nm excitation/405 nm emission filters.

1.2 Maintenance of the Primary Chondrocytes

Normal human articular chondrocytes (NHACs) passage 1, were acquired from a commercial source (Cat No CC-2550, Cambrex Verviers, BE). For every experiment, a vial containing primary NHACs is thawed according to the manufacturers protocol and cells are cultured in monolayer in a T80 cell culture vessel in chondrocyte growth medium (CGM, Cat No CC3216, Cambrex, Verviers) under standard conditions (37° C., 5% $CO_2$). When this culture reaches confluence, the cells are trypsinized according to the manufacturers protocol (using reagent pack Cat No CC-3233, Cambrex, Verviers, BE) and transferred to a new T175 culture vessel (1×10E+05 cells/T175 flask). When these cultures reached confluence, cells were trypsinized and subjected to the MMP13 assay. Therefore, the cells used for the MMP13 assay were only subcultured for 2 passages after thawing.

1.3. Screening Procedure

The optimal screening protocol is as follows: 96 well tissue culture plates are coated with 50 μL of 1.5% of low melting point agarose prepared in DMEM-F12 medium supplemented with 5% of FBS and a mixture of 100 units/mL penicillin (Invitrogen) and 100 μg/mL streptomycin (Invitrogen) (this medium is further referred to as "assay medium"). NHACs were trypsinized and seeded in polypropylene 96 well plates (to avoid cell adhesion) at a density of 7500 cells/20 μL/well in DMEM-F12 medium containing 5% of FBS and a mixture of penicillin and streptomycin. The cells are then infected with an adenovirus mediating the expression of human Coxsackie/adenovirus receptor (hCAR) (at an MOI (multiplicity of infection, referring to the amount of viral particles used per cell in the assay) of approximately 250) in order to facilitate the subsequent infection with the Ad-siRNA viruses contained in the SilenceSelect collection. The human Coxsackie/adenovirus receptor is a coreceptor that is involved in the attachment of the adenovirus to the human cell membrane. Expression of this receptor in cells has been described to facilitate subsequent infection with adenoviruses, for example in T-cells (Schmidt et al., 2000). One day later, 12 μL Ad-siRNA virus from each well of the SilenceSelect® collection (WO 03/020931), stored in 384 well plates (estimated titer of $1\times10^9$ viral particles per mL) was transferred with the aid of a 96/384 channel dispenser to individual wells of the 96 well plates containing the NHACs. As the average titer of the adenoviral library is $1\times10^9$ Virus Particles/mL, this represents an average MOI of about 1600. After addition of the Ad-siRNA to the wells, an incubation step of one hour at 37° C. is performed. The infection is performed in an arrayed fashion as each well is infected with one individual type of Ad-siRNA from the SilenceSelect® collection. 40 μL of 0.8% low melting point agarose prepared in DMEMF12 medium supplemented with 8% FBS and a mixture of penicillin and streptomycin are then added to the wells. The content of the wells is mixed by pipetting up and down with a multichannel robot and 50 μL of the mixture is transferred to the 96 well plates coated with agarose. To speed up the solidification of the agarose, the plates are stored at 4° C. for approximately 15 minutes. 150 μL of assay medium is the added to the wells. The infected NHACs are then incubated for four days to allow the shRNA expression in the cells to reach sufficient levels and the gene silencing machinery in the cells to be fully primed and active. Four days after infection, the medium on the cells is refreshed with assay medium. One day later, the cells are triggered by addition of assay medium containing 10 ng/mL recombinant human IL1b. Two days after addition of the trigger, supernatant is collected and stored at −80° C. until subjected to the MMP13 ELISA. 35 μL of the supernatant are subjected to the MMP13 ELISA, which is performed in a 384 well plate format. The protocol applied for the high-throughput compatible ELISA is described in Example 1.1. The infection, medium replacement and medium collection steps were performed with a TECAN Freedom pipettor (Tecan Freedom 200 equipped with TeMO96, TeMO384 and RoMa, Tecan AG, Switzerland).

1.4. Performance of the Control Plate

A 96 well control plate is generated to assess the quality of the assay. The control plates are produced in the same way as the SilenceSelect® collection. Multiple aliquots of this control plate are produced and stored at −80° C. For every screening run, a new aliquot of the screening plate is thawed and tested to allow the performance of all the screening runs to be compared. The composition of this plate is as follows. Wells are filled with control viruses that are produced under the same conditions as the SilenceSelect® adenoviral collection (WO 03/020931). This control plate contains four sets of positive control viruses (8 wells per positive control virus; $P_1$ (Ad5-RIT1_v5_KD), $P_2$ (Ad5-SLC26A8_v2_KD), $P_3$ (Ad5-TRAF6_v4_KD), $P_4$ (Ad5-NFKBIA_KI)), arranged in columns, interspaced with three sets of negative control viruses (16 wells per negative control virus; $N_1$ (Ad5-Empty_KD), $N_2$ (Ad5-M6PR_v1_KD), $N_3$ (Ad5-LacZ_KI)). The negative controls viruses are tested either in presence of IL1 (8 wells) or in the absence of IL1 (8 wells). The positive control samples are selected either based on literature information ($P_3$ (Ad5-TRAF6_v4_KD), $P_4$ (Ad5-NFKBIA_KI)) or based on a preliminary screening of limited Ad-siRNA viruses ($P_1$ (Ad5-RIT1_v5_KD), $P_2$ (Ad5-SLC26A8_v2_KD)). TRAF6 is known to be required for the signal transduction downstream of IL1 (Cao et al., 1996), and over-expression of NFKBIA is known to inhibit NFKappaB, a transcription factor known to be required for the expression of MMP13 (Karin, 1999).

Figure 3:
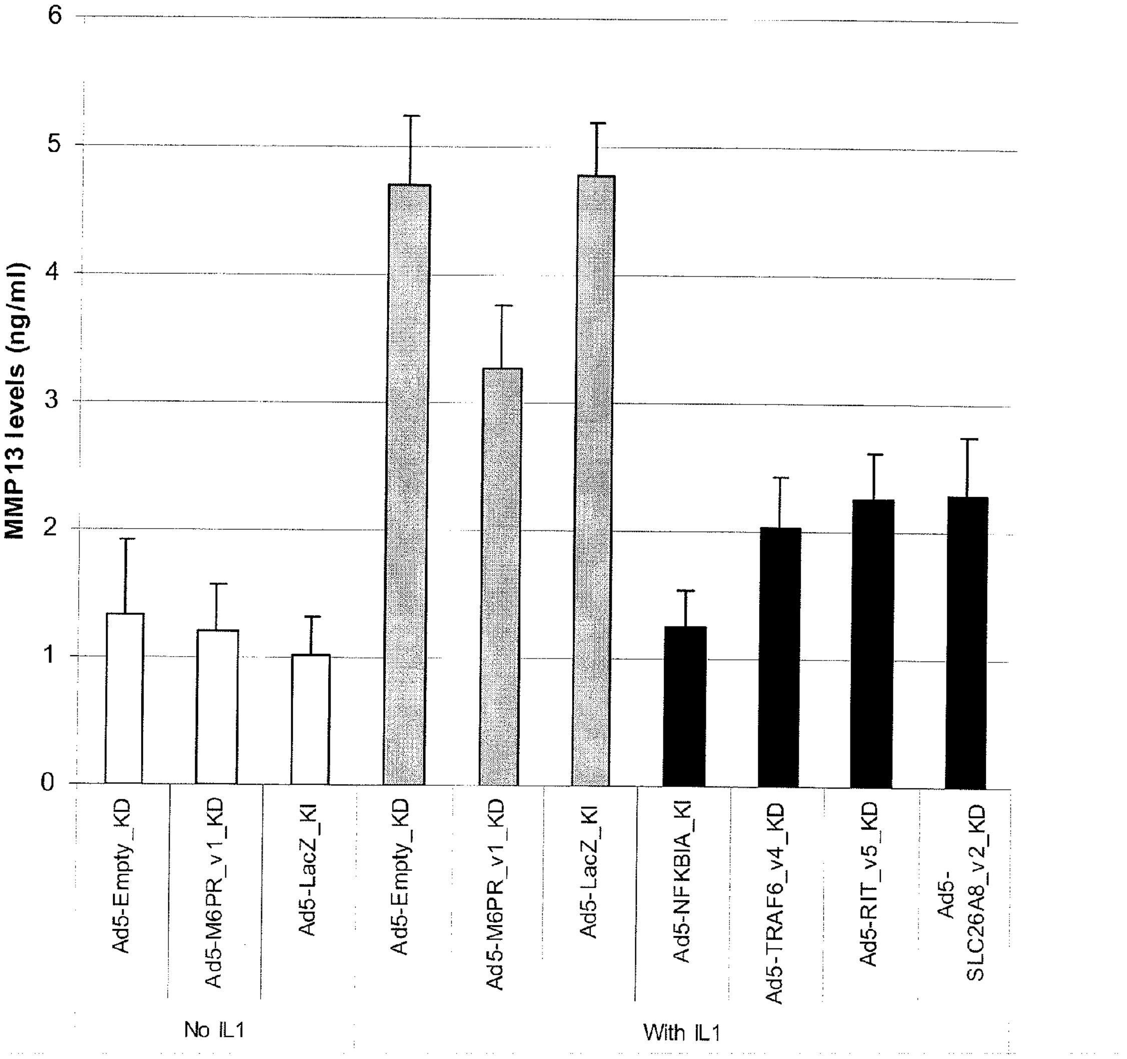
FIG. 3: A representative example of the performance of the control plate tested with the screening protocol described for the MMP13 assay in normal human articular chondrocytes

The control plate is run in parallel with and under the same conditions as the aliquot plates from the SilenceSelect® collection during the different screening runs. A representative example of the performance of the control plate tested with the screening protocol described above is shown in FIG. 3. The data shown represent the levels of MMP13 produced by NHACs infected with the viruses contained in the control plate. The average of the data obtained from the testing of 2 control plates are shown. The data indicate a clear upregulation of the MMP13 expression by IL1 treatment of the cells. The maximal MMP13 levels that are obtained upon IL1 treatment of the cells is comparable for the 3 negative controls. All 4 positive controls reduced the IL1 response of the NHACs, with the strongest effects being observed for the $P_3$ (Ad5-TRAF6_v4_KD) and $P_4$ (Ad5-NFKBIA_KI) positive controls. These data confirm the good quality of the screening.

Example 2: Screening of the SilenceSelect Collection

Figure 4:
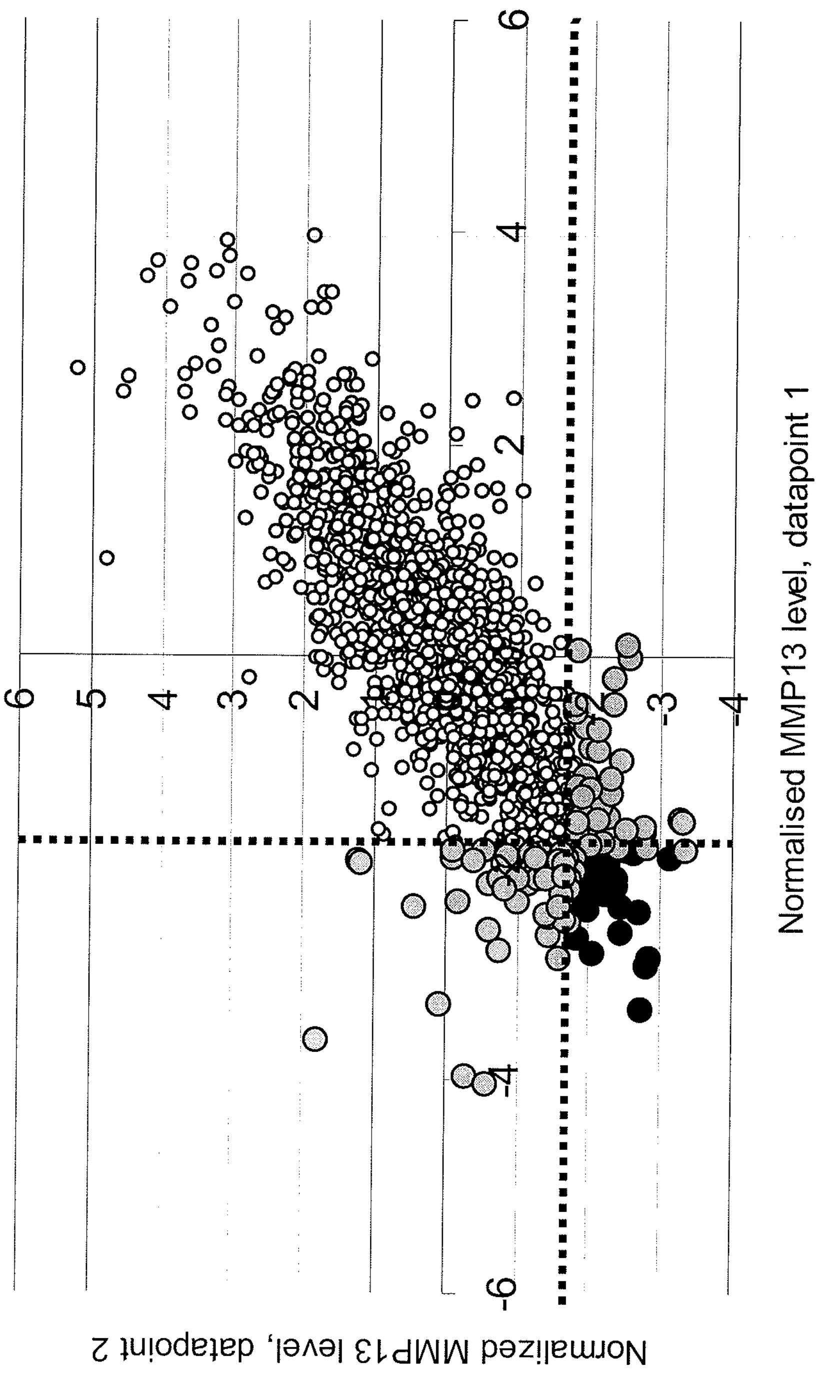
FIG. 4: Example of the data obtained during one of the screening batches of the SilenceSelect® collection

In total, 10946 viruses of the SilenceSelect collection are screened in the MMP13 assay performed on primary NHACs cultured in agarose in 3D format, according to the protocol described in example 1.3. These 10946 viruses cover 6308 transcripts, reflecting the redundancy built in the SilenceSelect® collection. This redundancy results in most transcripts being targeted by multiple independent Ad-siRNAs contained within the SilenceSelect® collection. The data obtained during one of the screening batches are shown in FIG. 4. During this screening batch, 1536 Ad-siRNAs contained in 4 384 well plates of the SilenceSelect® collection are screened in duplicate in the MMP13 assay. As mentioned in the description of the MMP13 assay on NHACs given in Example 1, the NHAC cell culture, infection with Ad5-siRNAs and activation with IL1 is performed in 96 well format. As such, every quadrant of a 384 well plate contained in the SilenceSelect® collection is used to infect two 96 well plates containing NHACs in parallel. The supernatant obtained is then transferred to a 384 well plate for the determination of the MMP13 levels in the MMP13 ELISA described in Example 1.1. Transfer is planned such that duplicate samples are measured on the same MMP13 ELISA plate. Data analysis is performed as follows:

First, for every 384 well plate individually, the data for all samples are normalized and transformed into "normalized values" as follows. All 384 datapoints are listed and the 5% highest and 5% lowest MMP13 signals are removed from the list. Mean and standard deviation are then calculated over all samples of this reduced list and based on these mean and standard deviation, the normalized data are calculated by applying the formula: normalized value sample A=[(raw MMP13 signal sample A−mean)/(standard deviation)]. This transformation of the data per 384 well plate allows comparison of samples of different screening batches.

Then a threshold value is determined to allow hit calling as follows. For every screening batch, two 96 well control plates are tested on parallel with the samples from the SilenceSelect® collection and every control plate contains 3 negative control viruses (8 wells per negative control virus). The average and standard deviation of the MMP13 signal for the 3 negative controls contained in the control plates (3 times 16 wells=48 wells in total) is calculated. Based on this data, various threshold values are expressed in relation to the standard deviation by applying following formula: threshold value=[(average over the negative controls)−("cutoff" times standard deviation over the negative controls)]. Various threshold values are then tested against the 48 negative controls. A cutoff is selected such that it defines a threshold value according to which less than 19% of the negative controls are lower than this threshold. Ad-siRNA viruses were nominated as primary hits if both datapoint (expressed as normalized values) for these Ad-siRNAs scored below the selected cutoff value in the primary screen.

In FIG. 4, the data are shown that are obtained in one of the screening batches during the screening of the SilenceSelect® collection against the MMP13 assay on NHACs. In this screening batch, 1536 Ad-siRNAs were tested in duplicate. On the graph, the 2 datapoints (expressed in terms of normalized MMP13 level) obtained for an Ad-siRNA are plotted against each other. The cutoff determined for this screening batch (−1.8) is indicated with dotted lines. The data for Ad-siRNA's that generated 2 datapoints that are below the selected cutoff and were nominated as primary hits (36 Ad-siRNA's) are indicated as black dots, the data for Ad-siRNA's that generated only one datapoint below the selected cutoff (100 Ad-siRNA's) are indicated as gray dots, and the data for the non-hit Ad-siRNA's are indicated as white dots. The symmetry observed between the duplicate datapoints (the datapoints are concentrated around a straight line) demonstrates the good quality and reproducibility of the screening.

Figure 6:
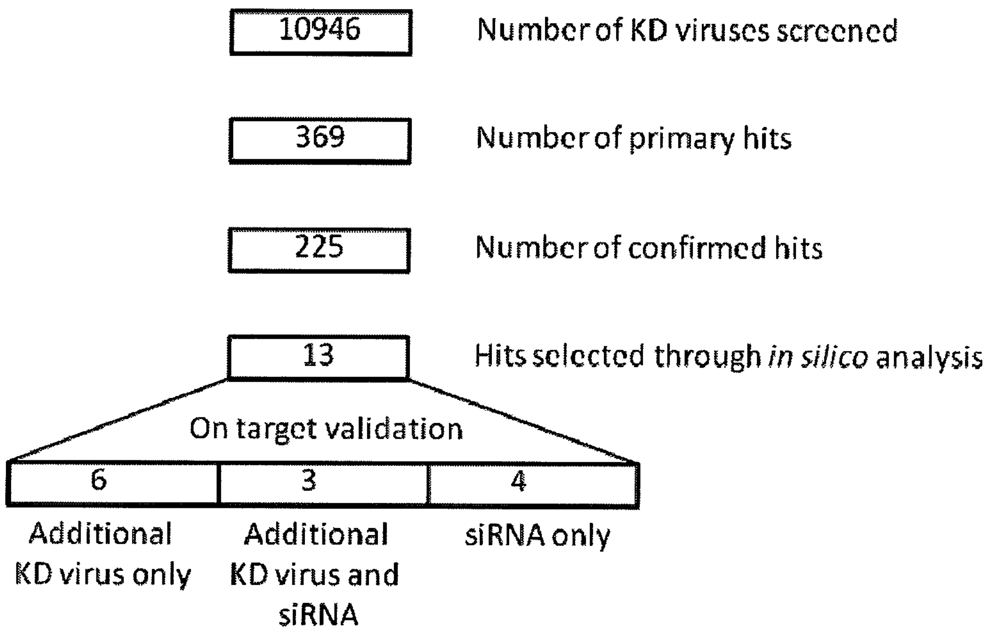
FIG. 6: Scheme indicating the attrition obtained during screening and the selection of the hits analysed in more detail.

The scheme shown in FIG. 6 displays the attrition obtained during screening and the selection of the hits analysed in more detail. Out of the 10946 Ad-siRNA's screened, 263 were identified as scoring in duplicate. In addition, in order to extract maximal value out of the primary screen, the list of viruses scoring only at one out of the 2 datapoints was further analyzed in order to identify independent viruses targeting an identical transcript. The fact that 2 independent Ad-siRNA's targeting the same gene through a different target sequence are active in the MMP13 assay, albeit more weakly, is considered valuable information. This analysis added 106 hits to the primary hit list, bringing the final number of primary hits to 369. These 369 primary hits were further analyzed in a rescreen procedure described in Example 3.

Example 3: 3MOI Rescreen 3.1 Rescreening Protocol

In order to turn primary hits into confirmed hits, original hit Ad-siRNA's are repropagated twice independently in order to produce independent Ad-siRNA material. These repropagated viruses are then tested in the MMP13 ELISA on NHACs at 3 MOI's. The new virus material is screened at 3 MOI's because the repropagation material could generate virus material with a different titer as compared to the original primary hits contained in the SilenceSelect® collection. As 2 repropagations are tested at 3 MOI's, 6 datapoints are generated for every Ad-siRNA subjected to the '3MOI rescreen'. Only the hits that score for at least 1 MOI for both repropagation materials are considered confirmed hits.

Figure 5A:
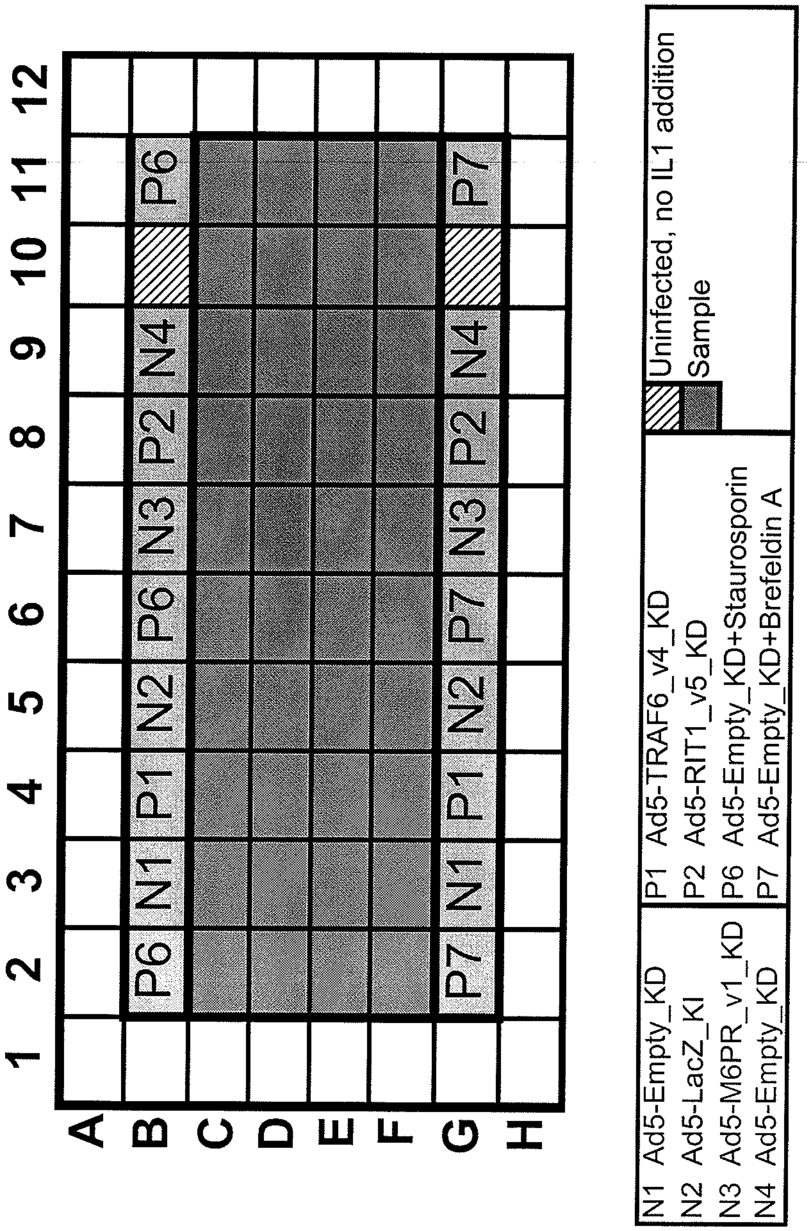
FIG. 5A: An exemplary layout for 3 MOI rescreen runs

For the repropagation step, the primary hits are picked from the SilenceSelect collection and repropagated in 96 well plates together with positive and negative controls. A possible layout for 3 MOI rescreen runs is shown in FIG. 5A. Each repropagation plate has 40 wells containing hit viruses surrounded by 20 control wells. These control wells contain either negative controls (N1(Ad5-Empty_KD); N2 (Ad5-LacZ_KI); N3 (Ad5-M6PR_v1_KD); N4(Ad5-Empty_KD) or positive controls (P1 (Ad5-TRAF6_v4_KD); P2 (Ad5-RIT1_v5_KD); P6 (Ad5-Empty_KD); P7(Ad5-Empty_KD). For propagation, the crude lysates of the hit Ad-siRNAs samples from the SilenceSelect® collection are picked and arranged together with controls in 96 well plates. As the containers of crude lysates are labeled with a barcode (Screenmates™, Matrix technologies), quality checks are performed on the plates. To propagate the viruses, 2.25×104 PER.C6/E2A cells are seeded in 200 μL of DMEM containing 10% non-heat inactivated FCS in each well of a 96 well plate and incubated overnight at 39° C. in a humidified incubator at 10% $CO_2$. One μL of crude lysate from each hit Ad-siRNA, arranged in the 96 well plates as indicated above, is then added to separate wells of PER.C6/E2A cells using a 96 well dispenser. After 7 to 10 days of incubation in a humidified incubator at 10% $CO_2$, the re-propagation plates are frozen at −20° C., provided that complete CPE (cytopathic effect, indicating virus production has been complete) could be observed.

In a next step, the Ad-siRNAs contained in the repropagation plates are tested in the MMP13 assay on NHACs. For this test, the same protocol was used as the one described in Example 2 for the primary screening, with the only difference that 3 volumes of the repropagated viruses are used to infect the chondrocytes subjected to the MMP13 assay: i.e. 8 μL, 12 μL and 16 μL. All control wells except the 2 uninfected ones are then activated with IL1. In addition, the P6 and P7 controls are treated with staurosporin (5 μM final concentration) and brefeldin A (0.5 μg/mL final concentration). These compounds are added one day before the addition of the IL1 trigger as well as one day later together with the addition of the IL1 trigger. The aim of the staurosporin and Brefeldin A addition to the P6 and P7 control wells is to define the background MMP13 expression levels when secretion by the NHACs is completely blocked (brefeldin A) or when the cells are treated with a cytotoxic compound (staurosporin). The data of the 3 MOI rescreens are analyzed as follows.

First, for every plate, sample data are normalized using following formula:

Normalized MMP13 value sample *A*=[((raw MMP13 signal sample *A*)−(median MMP13 signal over the negative controls))/(standard deviation over the MMP13 signal of the negative controls)].

The same basis is applied to generate the normalized value for the positive controls:

Normalized MMP13 value positive controls=[((Median MMP13 signal over the positive controls))−(median MMP13 signal over the negative controls)/(standard deviation over the MMP13 signal of the negative controls)].

For the "3 MOI rescreens", the positive controls are the wells treated with staurosporine and brefeldin A (P6 and P7), which are expected to reflect maximal inhibition of the IL1 induced MMP13 expression levels. Based on the normalized MMP13 values for the samples and the positive controls, the percentage inhibition is calculated for every sample by applying following formula: percentage inhibition sample A=[(Normalized MMP13 value sample A)/(Normalized MMP13 value positive controls)*100].

Figure 5B:
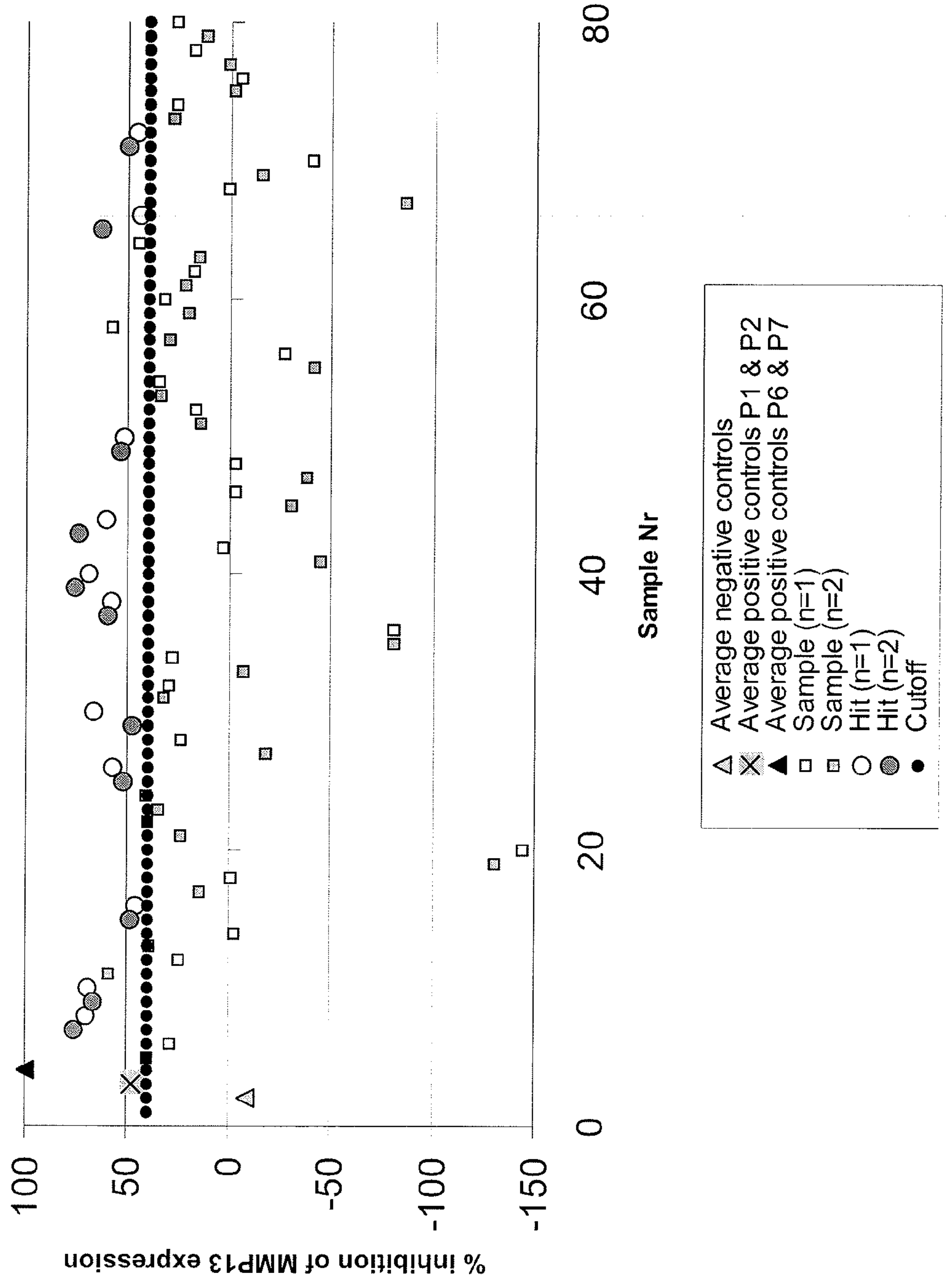
FIG. 5B: Example of the results obtained in a 3 MOI rescreen

An example of the outcome of a 3 MOI rescreen is shown in FIG. 5B. The experiment shown represents the data obtained during the screening of one 96 well repropagation plate (containing 40 primary hit AdsiRNA's as well as the appropriate controls) in the NHAC MMP13 assay at 8 μl in duplicate. Data are expressed as percentage inhibition of IL1-induced MMP13 expression. The cutoff selected for hit calling is 40 percent (represented as a dotted line). The average percentage inhibition for the P6 and P7 positive controls (100%) is represented as a black triangle, the average percentage inhibition for the P1 and P2 positive controls (48%) is represented as a cross and the average percentage inhibition for the N1, N2, N3 and N4 negative controls (−8.6%%) is represented as a gray triangle. Data for the Ad-siRNA's adhering to the hit calling criteria (2 datapoints are above the 40% cutoff) are indicated as white or grey circles, the data for the Ad-siRNA's not adhering to the hit calling criteria are indicated as squares. Duplicates are plotted next to each other (n=1 as a white circle, n=2 as a grey circle). For this repropagation plate and at this MOI, 11 out of the 40 primary hit Ad-siRNA's were confirmed.

The 3 MOI rescreen data obtained for all 13 preferred targets are indicated in Table 3. This table shows the TARGETS identified as active in the "3 MOI rescreen".

TABLE 3

| | Primary screen | 3MOI rescreen | Additional KD virus | Synthetic siRNA |
|---|---|---|---|---|
| ADAM15 | Active | Active | Active | |
| ADAMTS6 | Active | Active | Active (2) | Active |
| GPR34 | Active | Active | Active | |
| GPR43 | Active | Active | Active | |
| EPHA5 | Active | Active | Active | |
| MAP2K2 | Active | Active | Active | |
| MC3R | Active | Active | Active (4) | Active |
| MET | Active | Active | Active | Active |
| STK32B | Active | Active | Active (3) | |
| CSNK1G2 | Active | Active | | Active |
| EDG4 | Active | Active | | Active |
| MAP4K1 | Active | Active | | Active |
| KCNN4 | Active | Active | | Active |

A typical example of the outcome of a rescreen experiment is displayed in FIG. 6. In this rescreen procedure, 225 out of the 369 KD virus hits tested were confirmed. Out of these, 13 were selected for further validation based on an "in silico" analysis in which various properties of candidate targets were analysed, as drugability, availability of consumables allowing screening of the target against small molecule collections, level of conservation of the target sequence between human and rodent orthologs.

3.2 Quality Control of Target Ad-siRNAs

The quality and identity of hit Ad-siRNAs are checked by PCR and sequencing as described further. Target Ad-siRNAs are propagated using derivatives of PER.C6® cells (Crucell, Leiden, The Netherlands) in 96-well plates, followed by sequencing the siRNAs encoded by the target Ad-siRNA viruses. PER.C6/E2A cells are seeded in 96 well plates at a density of 40,000 cells/well in 180 μL of PER.C6/E2A medium. Cells are then incubated overnight at 39° C. in a 10% $CO_2$ humidified incubator. One day later, cells are infected with 1 μL of crude cell lysate from SilenceSelect® stocks containing target Ad-siRNAs. Cells are incubated further at 34° C., 10% $CO_2$ until appearance of a cytopathic effect (as revealed by the swelling and rounding up of the cells, typically at 7 days post infection). The supernatant is collected, and the virus crude lysate is treated with proteinase K by adding to 4 μL Lysis buffer (1× Expand High Fidelity buffer with MgCl2 (Roche Molecular Biochemicals, Cat. No 1332465) supplemented with 1 mg/mL proteinase K (Roche Molecular Biochemicals, Cat No 745 723) and 0.45% Tween-20 (Roche Molecular Biochemicals, Cat No 1335465) to 12 μL crude lysate in sterile PCR tubes. These tubes are incubated at 55° C. for 2 hours followed by a 15 minutes inactivation step at 95° C. For the PCR reaction, 1 μL lysate is added to a PCR master mix composed of 5 μL 10× Expand High Fidelity buffer with $MgCl_2$, 0.5 μL of dNTP mix (10 mM for each dNTP), 1 μL of "Forward primer" (10 mM stock, sequence: 5' CCG TTT ACG TGG AGA CTC GCC 3' (SEQ. ID NO.: 59), 1 μL of "Reverse Primer" (10 mM stock, sequence: 5' CCC CCA CCT TAT ATA TAT TCT TTC C) (SEQ. ID NO.: 60), 0.2 μL of Expand High Fidelity DNA polymerase (3.5 U/μL, Roche Molecular Biochemicals) and 41.3 μL of $H_2O$.

PCR is performed in a PE Biosystems GeneAmp PCR system 9700 as follows: the PCR mixture (50 μL in total) is incubated at 95° C. for 5 minutes; each cycle runs at 95° C. for 15 sec., 55° C. for 30 sec., 68° C. for 4 minutes, and is repeated for 35 cycles. A final incubation at 68° C. is performed for 7 minutes. 5 μL of the PCR mixture is mixed with 2 μL of 6× gel loading buffer, loaded on a 0.8% agarose gel containing 0.5 μg/μL ethidium bromide to resolve the amplification products. The size of the amplified fragments is estimated from a standard DNA ladder loaded on the same gel. The expected size is approximately 500 bp. For sequencing analysis, the siRNA constructs expressed by the target adenoviruses are amplified by PCR using primers complementary to vector sequences flanking the SapI site of the pIPspAdapt6-U6 plasmid. The sequence of the PCR fragments is determined and compared with the expected sequence. All sequences are found to be identical to the expected sequence.

Example 4: On Target Validation

The strengths and advantages of the siRNA technology are well-recognized and proved by the speed at which the technology has spread over the scientific community. Still the use of this technology asks for the required skills and knowledge as 1) siRNAs may nonspecifically target unrelated genes with only partial sequence-complementarity (off-target effects) and 2) the efficacy of siRNA's is difficult to predict (Pei et al., 2006). As such, it remains important to confirm the activity of a primary hit identified in a KD virus screen in an independent setting. Two approaches were taken to this end. First, a set of additional KD viruses were produced which were designed to reduce the expression of a certain gene through different target sequences. Second, synthetic siRNAs were purchased (Dharmacon) and used for target validation in the chondrocytic cell line SW1353.

4.1. On Target Analysis Using Additional KD Viruses

A set of KD viruses designed to reduce the expression of selected preferred hits through different target sequences were produced. These KD viruses were subsequently arrayed on 96 well plates together with positive and negative control viruses. Identical controls were used as described for the repropagation plates described for the 3MOI rescreen (Example 3). All additional different KD viruses targeting a particular hit were regrouped on a plate together with the original hit KD virus identified for this target during the primary screen. These plates were repropagated 2 times. Two copies of every repropagated plate was then tested in duplicate in 2 independent runs in the NHAC MMP13 assay as described above for the primary screen, using an MOI of 12 μl. As such, 8 datapoints were generated for every KD virus. The data were analysed as described above for the 3MOI rescreen (Example 3), converting the data to % inhibition. KD viruses giving rise to a reduction of the MMP13 levels of 35% for 4 out of the 8 datapoints generated were considered validated in this assay. As such, 1 additional KD virus having the capacity to reduce IL1_induced MMP13 expression levels in NHACs was identified for the following targets: ADAM15, GPR34, EPHA5, MAP2K2, MET, GPR43, 2 additional KD viruses were identified for ADAMTS6, 3 for STK32B and 4 for MC3R.

4.2. On Target Analysis Using Synthetic siRNA

The purpose of this experiment was to further validate adenoviral shRNA mediated KD effects on IL1 triggered MMP13 release using synthetic siRNA duplexes. The validation was done in a chondrosarcoma SW1353 cell line that was previously shown to upregulate MMP13 expression in response to IL1 triggering.

4.2.1 Materials

Human chondrosarcoma SW1353 cells (Cat. No. HTB-94, ATCC) are grown in a humidified 5% $CO_2$ incubator at 37° C. in DMEM (Cat. No. 41966-029, Gibco) supplemented with 10% heat-inactivated FBS (Hyclone) and 1× Penicillin/Streptomycin (Cat. No. 15140-122, Gibco) and subcultured (1:5 split ratio) twice a week after trypsinization.

Ready-to-use gene silencing siRNA duplexes for genes of interest may be obtained from Dharmacon. siGENOME SMARTpool (or ON-TARGETplus set of 4) lyophilized stock reagents are reconstituted in 1× siRNA Buffer (Cat. No. B-002000-UB-015, Dharmacon) to achieve 2 μM concentrations and aliquots are stored at −20° C.

4.2.2 Procedure siRNA duplexes are delivered into the SW1353 cells under optimized conditions. SW1353 cells are plated in 96-well plates (Nunc) at 10 000 cells/100 μL cell culture medium 24 hours prior to transfection. Cells are transfected with the siRNA reagents (30 nM or 10 nM final concentration) using INTERFERin™ (Cat. No. 409-10, Polyplus-transfection) at a final concentration of 1 L/well, essentially according to the manufacturers instructions. In brief, the siRNA stock reagent is diluted in 50 μL serum-free OptiMEM (Cat. No. 51985-026, Gibco) and 1 μL INTERFERin™ reagent is added followed by immediate homogenization for 10 sec and incubation at room temperature for 10-45 minutes to allow INTERFERin™/siRNA complexes to form. During complex formation the medium on top of the SW1353 cells is replaced with 100 μL pre-warmed cell culture medium containing no antibiotics. 50 μL of the formed INTERFERin™/siRNA mix is then added to the cells and plates are returned to the incubator at 37° C. and 5% $CO_2$.

After 72 hr, the medium on top of the cells is removed and replaced with 100 μL pre-warmed culture medium containing 10 ng/mL recombinant human IL1β (Cat. No. 200-01B, PeproTech) and 25 ng/mL recombinant human OSM (Cat. No. 295-0M, R&D Systems). Culture medium is DMEM/F12 (Cat. No. 11320-074, Gibco) containing 5% heat-inactivated FBS and 1× Penicillin/Streptomycin.

24 hr after addition of the cytokines, the supernatant is collected and stored at −80° C. for later analysis of appropriate dilutions in the MMP13 ELISA (see example 1), MMP1 ELISA (as described in WO 2006/040357) and TIMP2 ELISA (as described in WO 2006/040357). As TIMP2 levels are not influenced by the addition of the trigger, changes in amount of TIMP2 secreted into the supernatant are used to assess the effect of siRNA gene-specific duplex transfection on cell viability/secretion.

The effect of siRNA duplex delivery for genes of interest on IL1/OSM mediated upregulation of MMP13 and MMP1 may be assessed in two independent experiments. In each experiment transfection of siRNA duplexes is performed in duplicate at two siRNA concentration (10 nM and 30 nM). SMARTpool reagents targeting the human MMP1 (siGENOME SMARTpool siRNA MMP1), and one out of 4 selected individual siRNA duplexes targeting the human TRAF6 gene (siGENOME SMARTpool siRNA set of 4) and MMP13 gene (siGENOME SMARTpool set of 4) are used as positive controls. Cells transfected with the siCONTROL Non-Targeting siRNA pool or with the GL2.2 duplex targeting luciferase at 30 nM and/or 10 nM are used as negative controls. For MMP1 analysis, negative controls include both siRNA reagents at the two concentrations. For MMP13 analysis, negative controls include the non-targeting siRNA reagent at 30 nM and 10 nM and the GL2.2 duplex at 10 nM. Additional wells transfected with the GL2.2 control that are left unstimulated are included as non-triggered controls. Positive, negative and non-triggered controls are included on each 96-well plate. The collected supernatant of 4 different 96-well plates are analysed on one 384-well ELISA and results may be analysed as follows:

First, MMP13 and MMP1 numeric data for each well are recalculated as percentage inhibition of the signal (% PIN) as follows:

$$\% \text{ PIN}=100-((\text{signal}_{sample}-\text{Av signal}_{non\text{-}triggered\ control})/(\text{Av signal}_{negative\ controls}-\text{Av signal}_{non\text{-}triggered\ control})*100)$$

where,

Av $\text{signal}_{non\text{-}triggered\ control}$ is the average of non-triggered control of the 4 96-well plates all analysed on the same 384 ELISA Av $\text{signal}_{negative\ controls}$ is the average of described negative controls of 4 96-well plates all analysed on the same 384 ELISA TIMP2 results are expressed as percentage inhibition of the signal (% PIN) according to the following formula:

$$\% \text{ PIN}=100-((\text{signal}_{sample}-\text{Av signal}_{background})/(\text{Av signal}_{negative\ controls}-\text{Av signal}_{background1})*100)$$

where

Av $\text{signal}_{background1}$ is the background signal of the TIMP2 ELISA i.e. signal obtained in absence of TIMP2

Av $\text{signal}_{negative\ controls}$ is the average of all negative controls of 4 96-well plates analysed on same 384 ELISA Then, individual wells may be said to have a positive score if the % PIN was higher than 35% (for MMP1) or than 50% (MMP1). At these cutoff settings none of the negative controls are found to have a positive score. Results for transfections at 10 nM or 30 nM are given a scoring value of 1, only if both replicates are scoring above preset cutoffs. In order to assure that a drop in MMP1 or MMP13 expression is not caused by loss of cell viability, the TIMP2 results are taken into consideration. If TIMP2 signal is found to drop more than 35% for both replicates then result of MMP1 or MMP13 is not taken into account. For each screen a final value is assigned to the target that was the sum of the scoring values at both siRNA duplex test concentrations after taking into account the TIMP2 analysis. The effect of the siRNA duplex for a given gene is then believed to be a "true" effect if the sum of the final values of both screens is higher or equal to 2. The target is considered validated with synthetic siRNA if it scored as a true hit in either MMP1 or MMP13. As such, following targets were considered validated using the synthetic siRNA technology: ADAMTS6, MC3R, MET, CSNK1G2, EDG4, MAP4K1, KCNN4.

Taken together, the outcome of the on target validation exercise for the 13 hits selected through the on target analysis is indicated in Table 3. Nine targets were validated through the identification of an additional KD virus capable of recapitulating the effects of the original KD virus hit identified in the primary screen and 7 (3 of which were validated with an additional KD virus) were validated using the synthetic siRNA technology. Expression of these validated targets in primary human chondrocytes was further assessed (Example 5).

Example 5: Expression Analysis in Human Chondrocytes of the Preferred Targets In order to be validated as preferred targets, the genes should be expressed in chondrocytes. This may be assessed using quantitative real-time PCR. Normal human chondrocytes from articular cartilage (NHAC) (Cambrex, Verviers, Belgium) are seeded into 9 cm culture dishes at 3 million cells/dish in DMEM/F12 medium supplemented with 5% fetal calf serum (HighClone, Perbio, Erembodegem, Belgium). Two days later culture medium is replaced by either DMEM/F12 medium supplemented with 5% fetal calf serum, with or without 10 ng/mL of IL-13, or with Chondrocyte differentiation medium (CDM, Cell Applications, San Diego, Calif.), with or without 10 ng/mL IL-13. Each condition is performed in duplicate. After incubation for 48 h the medium is removed and cells are processed for RNA isolation using the RNeasy midi kit according to the manufacturer's instructions (Qiagen, Venlo Netherlands) and purified RNA is stored in aliquots at −20° C.

RNA is reverse transcribed to cDNA using the TaqMan® Gold RT kit (Applied Biosystems, Lennik, Belgium), according to the manufacturer's instructions (1× TaqMan® RT buffer, 5 mM MgCl2, 0.5 mM dNTP, 2.5 μM random hexamers, 10 U RNase inhibitor and 25 U multiscribe reverse transcriptase).

The cDNA is diluted 6-fold and 5 μL is used per PCR reaction in a 25 μL reaction for real-time QPCR in a ABI7000 instrument using either the SYBR® Green universal Mastermix or the TaqMan® Universal Mastermix (Both from Applied Biosystems).

For primer development in SYBR® Green QPCR analysis, DNA sequences are extracted from the RefSeq sequence depository, or, if not available, from the GenBank collection. From these sequences, primer pairs suitable for SYBR® Green QPCR are designed using the PrimerExpress software (Applied Biosystems). These primer pairs are checked for their specificity toward their target gene with the Blast software (NCBI, Entrez). Suitable primer pairs are ordered (Invitrogen) and used at 0.3 μM concentration. The primer pairs are shown in FIG. 7.

Primer pair quality is monitored by melting point analysis, whereby pairs yielding more than one melting point are discarded, and by comparison to a reference cDNA (Clontech Laboratories, Mountain View, Calif.) whereby the difference in melting point should not differ by more than 1° C.

For the genes for which the SYBR® Green primer pair does not fulfill the requirements, a TaqMan® assay is used (Assay-on-demand, Applied Biosystems).

Genes are considered as expressed if the average Ct value over all conditions was 37 or less.

Expression of the preferred targets in human articular chondrocytes as obtained by quantitative real-time PCR. Each Ct value is the average of 8 independent RNA preparations of cells grown in 4 different conditions, as outlined in Example 5. The results are show in Table 5.

TABLE 5

Expression of the preferred targets in human articular chondrocytes

| Hit-ID | 2nd hit-ID | Target Gene Symbol | average Ct values |
|---|---|---|---|
| H54-001 | | MET | 26.3 |
| H54-016 | | STK32B | 30.70 |
| H54-023 | | GPR34 | 36.18 |
| H54-024 | H54-025 | GPR43 | 32.86 |
| H54-044 | | MAP2K2 | 26.70 |
| H54-058 | | ADAMTS6 | 32.24 |
| H54-094 | | KCNN4 | 32.11 |
| H54-127 | H54-305 | ADAM15 | 26.04 |
| H54-140 | | MAP4K1 | 29.77 |
| H54-165 | | MC3R | 33.98 |
| H54-257 | | EPHA5 | 30.76 |

TABLE 5-continued

| Expression of the preferred targets in human articular chondrocytes | | | |
|---|---|---|---|
| Hit-ID | 2nd hit-ID | Target Gene Symbol | average Ct values |
| H54-269 | | CSNK1G2 | 23.15 |
| H54-340 | | EDG4 | 32.97 |

A Ct value of below 25 is considered high expression, between 25 and 30 is considered good expression, between 30 and 35 is considered moderate expression and above 35 is considered low expression. Therefore, good expression levels in primary chondrocytes could be demonstrated for most targets except for GPR34 (Ct=36), that displayed a low expression level. However, low expression levels may be observed for GPCRs and this low expression is not always predictive for low receptor activity

Example 6 Further Validation of EPHA5

Exemplary foregoing TARGET EPHA5 has been validated and confirmed by compounds directed against EPHA5 which inhibit EPHA5 and also inhibit MMP13 activity in NHACs. The activity against EPHA5 may be tested using the assays as described in Examples 6.1 and 6.2 below, ability to inhibit MMP13 activity in NHACs may be tested as described in Example 7.

6.1 EPHA5 Inhibition—Biochemical Assay

Recombinant Epha5 (Millipore catalog number 14-639) is incubated with 0.1 mg/mL Poly(Glu,Tyr)sodium salt (4:1), MW 20 000-50 000 (Sigma catalog number P0275) in kinase reaction buffer (10 mM MOPS pH7.0, 1 mM DTT, 0.01% Trition-X100, 2.5 mM $MnCl_2$, 0.5 mM $Na_3VO_4$, 5 mM beta-glycerolphosphate, 0.5 μM non-radioactive ATP, 0.25 μCi 33P-gamma-ATP (Perkin Elmer, catalog number NEG602K) final concentrations with or without 5 μL containing test compound or vehicle (DMSO, 1% final concentration), in a total volume of 25 μL, in a polypropylene 96-well plate (Greiner, V-bottom). After 45 min at 30° C., reactions are stopped by adding 25 μL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 μL per well of a 75 mM phosphoric acid solution and the bottom of the plates is sealed. 40 μL/well of Microscint-20 is added, the top of the plates is sealed and readout is performed using the Topcount (Perkin Elmer). Kinase activity is calculated by subtracting counts per minute (cpm) obtained in the presence of a positive control inhibitor (10 μM staurosporine) from cpm obtained in the presence of vehicle. The ability of a test compound to inhibit this activity is determined as:

Percentage inhibition=((cpm determined for sample with test compound present−cpm determined for sample with positive control inhibitor) divided by (cpm determined in the presence of vehicle−cpm determined for sample with positive control inhibitor))*100%.

Dose dilution series are prepared for the compounds enabling the testing of dose-response effects in the EPHA5 assay and the calculation of the $IC_{50}$ for each compound. Each compound is routinely tested at concentration of 30 μM followed by a 1/3 serial dilution, 8 points (30 μM-6.67 μM-2.22 μM-740 nM-247 nM-82 nM-27 nM-9 nM) in a final concentration of 1% DMSO. If potency of compound series is increased, more dilutions may be prepared and/or the top concentration may be lowered (e.g. 5 μM, 1 μM).

6.2 EPHA5 Inhibition—Cell Assay

The assay principle is to determine inhibitor activity on the STAT3 (Tyr705) phosphorylation level in HEK293 cells transiently transfected with STAT3 and EPHA5.

HEK293 are maintained in Dulbecco's Modified Eagle's Medium (DMEM) containing 10% heat inactivated fetal calf serum, 100 U/mL Penicillin and 100 μg/mL Streptomycin.

HEK293 at 70% confluency are collected by standard trysinisation. 15,000,000 cells are transiently transfected with 6,250 ng of pIPspAdapt6-STAT3, 3,750 ng of pIPsp-Adapt6-EPHA5, 4,000 ng of pIPspAdapt6-eGFP and 11,000 ng of pBSK using 50 μL Jet-PEI (Polyplus) as transfection reagent per T175 $cm^2$ cell culture flask. The transfected cells are seeded in T175 $cm^2$ cell culture flask. After overnight incubation at 37° C., 10% $CO_2$, transfection medium is removed and fresh cell culture medium is carefully added to avoid cell detachment.

48 hour after transfection, medium is removed. Cells are detached with prewarmed cell dissociation solution (Sigma cat no. C5914). 60,000 cells/40 μL of DMEM are seeded per well in 384-well plate. Then 10 μL of compound dilution (5×) in DMEM is added.

All compounds are tested in duplicate starting from 20 μM followed by a 1/3 serial dilution, 8 points (20 μM-6.6 μM-2.2 μM-740 nM-250 nM-82 nM-27 nM-9 nM) in a final concentration of 0.2% DMSO.

After 5 h incubation at 37° C., phosphor-Stat3(Tyr705) levels are determined using the AlphaScreen® SureFire® Phospho-STAT 3(Tyr705) Assay Kit (From Perkin Elmer). Cells are lysed by addition of 15 μL of 1× lysis buffer. The plate is gently shaken for 20 min at room temperature, 4 μL of lysate is transfered to the proxiplate, then 7 μL reaction buffer/activation buffer mix containing alpha-beads are added and the plate is sealed with an aluminium seal, shaken for 5 minutes and incubated for 16 hours at RT in the dark.

The plates are read on the Envision using standard AlphaScreen settings. 0.2% DMSO is used as a negative control (0% inhibition). The positive and negative controls are used to calculate z' and PIN values.

Percentage inhibition=(1−((value determined for sample with test compound present−value determined for sample with positive control inhibitor) divided by (value determined in the presence of vehicle−value determined for sample with positive control inhibitor)))*100%.

Example 7 MMP13 Inhibition Assay

Compounds identified as being active against one of the TARGETs identified herein, may be directly tested in an MMP13 inhibition assay.

Normal human articular chondrocytes (NHAC, Lonza cat no CC-2550) are suspended at a concentration of 1 600 000 cells per mL in medium (Gibco, DMEM:F12) containing 5% FBS and 1% pen/strep. 25 μL of the cell suspension is then pooled with 25 μL 0.8% agarose in medium with 5% serum and 1% pen/strep and added to a well of a 96-well culture dish precoated with 50 μL 1.5% agarose in medium with 5% serum and 1% pen/strep. After the agarose has set, 127.5 μL medium is added to each well. The cells are then treated with 7.5 μL compound at various concentrations for 1 hour followed by triggering with 15 μL 10 ng/mL IL-1b (final concentration: 1 ng/mL). 48 hours after triggering, the supernatant is harvested and MMP13 secretion is measured. Each compound is routinely tested at concentration of 30

μM followed by a 1/3 serial dilution, 8 points (30 μM-10 μM-3.33 μM-1.11 μM-370 nM-123 nM-41 nM-14 nM) in a final concentration of 0.3% DMSO.

MMP13 activity is measured in an antibody capture activity assay. For this purpose, 384 well plates (NUNC, P6491, MaxiSorp black) are coated with 35 μL of a 1.5 μg/mL anti-human MMP13 antibody (R&D Systems, MAB511) solution for 24 hours at 4° C. After washing the wells 2 times with PBS+0.05% Tween, the remaining binding sites are blocked with 100 μL 5% non-fat dry milk (Santa Cruz, sc-2325, Blotto) in PBS for 24 hours at 4° C. Then, the wells are washed 2 times with PBS+0.05% Tween and 35 μL culture supernatant containing MMP13 is added and incubated for 4 hours at room temperature. Following this the wells are washed 2 times with PBS+0.05% Tween and MMP13 protein is then fully activated by addition of 35 μL of a 1.5 mM 4-Aminophenylmercuric acetate (APMA) (Sigma, A9563) solution and incubation at 37° C. for 1 hour. Then, the wells are washed again with PBS+0.05% Tween and 35 μL MMP13 substrate (Biomol, P-126, OmniMMP fluorogenic substrate) is added. After incubation for 1 hour at 37° C. fluorescence of the converted substrate is measured in a Perkin Elmer Wallac EnVision 2102 Multilabel Reader (wavelength excitation: 320 nm, wavelength emission: 405 nm).

Percentage inhibition=((fluorescence determined in the presence of vehicle−fluorescence determined for sample with test compound present) divided by (fluorescence determined in the presence of vehicle−fluorescence determined for sample without trigger))*100%.

The activity of compounds against GPR43 may be tested using the assays as described Example 8 or 9 below

Example 8: GPR43 Phenotypic Assay—Neutrophil Migration Assay 8.1 Isolation of Neutrophils from Buffy Coats A human buffy coat is diluted with an equal volume of ice cold DPBS (Invitrogen cat#14190169). 20 mL of diluted buffy coat down is gently mixed with 4 mL of 140 mM citric acid, 200 mM sodium citrate and 220 mM Dextrose in a 50 mL conical tube. 12 mL of a 6% Dextran/0.9% NaCl solution (W/V) in water is added gently and mixed by inverting the tube up to 20 times. The total volume is then transferred to a fresh tube and incubated at room temperature for 1 hour for complete separation of the two phases. The yellow supernatant is then transferred to a new tube and centrifuged at 1300 rpm for 12 minutes in a standard table top centrifuge at 4° C. without brake. The supernatant is discarded and the remaining cell pellet is rapidly resuspended by pipetting up and down in 12 mL of ice-cold water. After 20 seconds 4 mL of ice cold 0.6 M KCl is added, mixed carefully and centrifuged at 1300 rpm for 12 minutes in a standard table top centrifuge at 4° C. without brake. This procedure is repeated until no red blood cells remain. Finally the pellet is resuspended in 4 mL of DPBS and layered over 5 mL of Lymphoprep™ (Nycomed Pharma, Cat#1114545) in a 15 mL tube. After centrifugation at 1300 rpm for 12 minutes in a standard table top centrifuge at 4° C. with low brake, the supernatant is removed and the cell pellet is resuspended in 25 mL chemotaxis buffer (RPMI 1640 (Invitrogen, Cat#21875) supplemented with 10 mM of HEPES (Invitrogen, Cat#15630).

8.2 Migration Assay

The migration assay is performed in a Corning HTS transwell 96 permeable support system with 5.0 μM pore size polycarbonate membrane (Corning Cat#3387). 180 μL of a cell suspension of 8.9×10$^6$ cells/mL is added to 20 μL of compound solution in chemotactic buffer in a polypropylene 96-well V-bottom plate. The cells are incubated for 30 minutes with an intermediate resuspension after 15 minutes to prevent the cells from settling to the plate bottom. Following this the 70 μL cell suspension is transferred to the upper compartment of the transwell system. The receiver well is filled with 200 μL chemotaxis buffer containing compound and chemotactic agent. After incubation at 37° C. in 5% $CO_2$ for 1 hour, the amount of cells that migrate to the receiver plate is measured by lysis and measuring ATP content of the lysate using ATP-lite (Promega, Cat#6016739) in a luminometer.

8.3 Data Analysis

Compound effects are expressed as percent inhibition using the formula:

[(RLU in the presence of vehicle & chemotactic agent−RLU in presence of compound & chemotactic agent)/(RLU in the presence of vehicle & chemotactic agent−RLU in absence of chemotactic agent)]*100

RLU=relative luminescence units.

Example 9: GPR43—Calcium Flux Assay

The activity against GPR43 may be tested using the assay as described in below

Clear bottom 384 well plates (Corning, ref. 3712) are coated with 25 μL poly-D-Lysine (Sigma, ref. P-6407) diluted in PBS at a final concentration of 0.05 mg/mL and incubated for 30 minutes at 37° C. Polylysine is removed by 2 washes with PBS. Six thousand HEK293 cells are seeded in 25 μL of DMEM complemented with 10% FBS, 10 μg/mL puromycin and 1% penicillin/streptomycin. The plates are then incubated for 24 hours at 37° C./5% $CO_2$. Twenty-five μL of calcium 4 dye (Molecular devices, ref. R8141) are added to plates according to manufacturer instructions and plates are incubated for 2 hours 15 minutes at 37° C./5% $CO_2$. Ten μL of compound solutions in HBSS, 20 mM hepes are then added and plates are incubated at 37° C./5% $CO_2$ for 15 minutes. Antagonist activity is measured by adding 10 μL of sodium acetate (Sigma, ref. S2889) in HBSS, 20 mM hepes at the $EC_{80}$ concentration.

Calcium signaling is measured using a Flex station3 (Molecular Devices) by recording fluorescence (excitation 485 nm, emission 525 nm) during sixty seconds. Activity is determined as the ration between the maximal fluorescence of the calcium curves produced by the sodium acetate and the basal fluorescence measured before sodium acetate addition. Percentages of inhibition are calculated using negative (vehicle addition) and positive (sodium acetate at $EC_{100}$) controls on each plate.

Example 10: EDG4 Calcium Flux Assay

The activity of compounds against EDG4 may be tested using the assay as described below Ten thousand CHO-EDG4 cells per well are resuspended in 50 μL of DMEM/F12 complemented with 10% FBS and 10 μg/mL Puromycin, then are seeded in clear bottom 384 well plates (Corning, ref. 3712). After 24 hours incubation at 37° C./5% $CO_2$ plates are washed twice with 25 μL of DMEM/F12 complemented with 0.1% fatty acid free BSA and then plates are incubated for 1 hour at 37° C./5% $CO_2$. Twenty-five μL of Fluo 4 Direct Ca dye (Invitrogen, ref. F10473) diluted in HBSS containing calcium and magnesium (Gibco ref. 14025) complemented with 20 mM HEPES (with further 12 dilution compared to manufacturer instructions), and 5 mM Probenicid (Invitrogen, ref. P36400) are added to the plates. Plates are then incubated for 1 hour at 37° C./5% $CO_2$. Ten μL of compound solutions in HBSS, 20 mM hepes, 0.1% fatty acid free BSA, 0.6% DMSO are then added and plates are incubated at 37° C./5% $CO_2$ for 15 minutes. Antagonist activity is measured by adding 10 μL of oleoyl-L-Lysophosphatidic acid sodium salt (LPA, Sigma, ref. L7260) in HBSS, 20 mM hepes, 0.1% fatty acid free BSA at the $EC_{80}$ concentration.

Calcium signaling is measured using a Flex station3 (Molecular Devices) by recording fluorescence (excitation 485 nm, emission 525 nm) for sixty seconds. Activity is determined as the ratio between the maximal fluorescence of the calcium curve produced by the LPA and the basal fluorescence measured before LPA addition. Percentages of inhibition are calculated using negative (vehicle addition) and positive (LPA at $EC_{100}$) controls on each plate.

The activity of compounds against CSNK1G2 may be tested using the assay as described in Example 11 or 12 below.

Example 11: CSNK1G2 Biochemical Assay 0.75 mU of recombinant CSNK1G2 (Millipore catalog number 14-712) is incubated with 0.1 mg/mL casein (Sigma catalog number C4765) in kinase reaction buffer (10 mM MOPS pH7.0, 0.01% Triton-X-100, 0.5 mM EDTA, 1 mM DTT, 0.5 mM $Na_3VO_4$, 5 mM beta-glycerophosphate, 10 mM $MgCl_2$, 0.5 μM non-radioactive ATP, 0.25 μCi 33P-gamma-ATP (Perkin Elmer, catalog number NEG602K) final concentrations with or without 5 μL containing test compound or vehicle (DMSO, 1% final concentration), in a total volume of 25 μL, in a polypropylene 96-well plate (Greiner, V-bottom). After 45 min at 30° C., reactions are stopped by adding 25 μL/well of 150 mM phosphoric acid. All of the terminated kinase reaction is transferred to pre-washed (75 mM phosphoric acid) 96 well filter plates (Perkin Elmer catalog number 6005177) using a cell harvester (Perkin Elmer). Plates are washed 6 times with 300 μL per well of a 75 mM phosphoric acid solution and the bottom of the plates is sealed. 40 μL/well of Microscint-20 is added, the top of the plates is sealed and readout is performed using the Topcount (Perkin Elmer).

Kinase activity is calculated by subtracting counts per minute (cpm) obtained in the presence of a positive control inhibitor (20 μM staurosporine) from cpm obtained in the presence of vehicle. The ability of a test compound to inhibit this activity is determined as:

Percentage inhibition=((cpm determined for sample with test compound present−cpm determined for sample with positive control inhibitor) divided by (cpm determined in the presence of vehicle−cpm determined for sample with positive control inhibitor))*100%.

Dose dilution series are prepared for the compounds enabling the testing of dose-response effects in the CSNK1G2 assay and the calculation of the $IC_{50}$ for each compound. Each compound is routinely tested at concentration of 30 μM followed by a 1/3 serial dilution, 8 points (30 μM-6.67 μM-2.22 μM-740 nM-247 nM-82 nM-27 nM-9 nM) in a final concentration of 1% DMSO. If potency of compound series is increased, more dilutions may be prepared and/or the top concentration may be lowered (e.g. 5 μM, 1 μM).

Example 12: CSNK1G2 Cell Assay

In the Wnt-signaling assay a Wnt luciferase reporter construct is transfected together with expression vectors for LRP6 and CSNK1G2 into SW1353 cells with the JetPEI transfection agent (Polyplus Transfection, Cat no 101-40). CSNK1G2 overexpression potentiates LRP6-induced Wnt-reporter activity. The CSNK1G2- and LRP6-mediated expression of the luciferase reporter gene is measured with a luciferase substrate. Compounds inhibiting CSNK1G2 activity will reduce reporter activity.

Day 1: a suspension of SW1353 cells is prepared (density: 30000 cells/well/80 μL (375000 cells/mL)). In parallel, a DNA/transfection agent mixture is prepared as follows.

The total amount of DNA to be added per well is diluted to 10 μL in a NaCl 150 mM solution. Typically, following amounts of DNA will be transfected per well: Wnt-luc reporter (20 ng), A010800-CSNK1G2-WT (20 ng), pCS-myc-hLRP (10 ng). The total amount of JetPEI transfection agent needed per well (0.32 μL) is diluted to 10 μL in a NaCl 150 mM solution. JetPEI solution and DNA solutions are then mixed yielding 20 μL DNA/transfection agent mix to be added per well. This solution is immediately mixed, centrifuged and incubated for 30 min at RT. The cell suspension is added dropwise to the DNA/transfection agent mix, and incubated at 37° C. for 2 hrs. The compound to be tested, diluted to 11 μL, is then added to the wells containing the transfected cells using an automated dispenser (Tecan aquarius) and the mixture is incubated for 16 to 24 hours.

Day 2: The medium on top of the cells is removed and the luciferase substrate SteadyLite HTS (Perkin Elmer, CatNo 550-070303) is then added to the white 96-well plates (50 μl/well). After an incubation of 30 min in the dark under continuous shaking, the readout is performed readout with a luminometer (Envision, Perkin Elmer).

REFERENCES

Appleton C T, Pitelka V, Henry J, Beier F, Global analyses of gene expression in early experimental osteoarthritis, Arthritis Rheum. 2007; 56(6):1854-68.

Billinghurst, R C, et al., Comparison of the degradation of type II collagen and proteoglycan in nasal and articular cartilages induced by interleukin-1 and the selective inhibition of type II collagen cleavage by collagenase. Arthritis Rheum. 2000; 43:664-672.

Billinghurst, R C, et al. Enhanced cleavage of type II collagen by collagenases in osteoarthritic articular cartilage. J Clin Invest. 1997; 99:1534-1545.

Boerner. P, Lafond, R, Lu, W Z, Brams, P, and Royston, I, Production of antigen-specific human monoclonal antibodies from in vitro-primed human splenocytes, J. Immunol., 1991, 147(1):86-95.

Cao, Z; Xiong, J; Takeuchi, M; Kurama, T; Goeddel, D V, TRAF6 is a signal transducer for interleukin-1. Nature 383: 443-446, 1996.

Chen, C J, Banerjea, A C, Harmison, G G, Haglund, K, Schubert, M, Multitarget-ribozyme directed to cleave at up to nine highly conserved HIV-1 env RNA regions inhibits HIV-1 replication—potential effectiveness against most presently sequenced HIV-1 isolates Nucl. Acids Res. 1992 20: 4581-4589;

Choy E H, Panayi G S. Cytokine pathways and joint inflammation in rheumatoid arthritis. N Engl J Med. 2001; 344(12):907-16.

Clegg D O, Reda D J, Harris C L, Klein M A, O'Dell J R, Hooper M M, Bradley J D, Bingham C O 3rd, Weisman M H, Jackson C G, Lane N E, Cush J J, Moreland L W, Schumacher H R Jr, Oddis C V, Wolfe F, Molitor J A, Yocum D E, Schnitzer T J, Furst D E, Sawitzke A D, Shi H, Brandt K D, Moskowitz R W, Williams H J. Glucosamine, chondroitin sulfate, and the two in combination for painful knee osteoarthritis. N Engl J Med. 2006; 354(8):795-808.

Cole, et al. (1985) Monoclonal Antibodies and Cancer Therapy, Alan R. Liss, p. 77;

Dahlberg, L, et al. Collagenase-mediated cleavage of type II collagen is selectively enhanced in osteoarthritis cartilage and can be arrested with a synthetic inhibitor which spares collagenase-1 (MMP-1). Arthritis Rheum. 2000; 43:673-682.

Firestein G S. Evolving concepts of rheumatoid arthritis, Nature. 2003; 423(6937):356-61.

Gao, X and Huang, L, Cytoplasmic expression of a reporter gene by co-delivery of T7 RNA polymerase and T7 promoter sequence with cationic liposomes, Nucl. Acids Res. 1993 21: 2867-2872

Hoogenboom and Winter, By-passing immunisation: Human antibodies from synthetic repertoires of germline VH gene segments rearranged in vitro, J. Mol. Biol. 1992, 227:381-8;

Karin M. The beginning of the end: IkappaB kinase (IKK) and NF-kappaB activation. J Biol Chem. 1999 Sep. 24; 274(39):27339-42. Review.

Kashani-Sabet, et al., Reversal of the malignant phenotype by an anti-ras ribozyme Antisense Res Dev, 1992 2:3-15

Lee D M, Weinblatt M E. “Rheumatoid arthritis” Lancet. 2001; 358(9285):903-11.

Lipinski C A, Lombardo F, Dominy B W and Feeney P J., “Experimental and computational approaches to estimate solubility and permeability in drug discovery and development settings” Adv Drug Deliv Rev, 2001; 46: 3-26

Mark and Padlan, (1994) “Chapter 4. Humanization of Monoclonal Antibodies”, The Handbook of Experimental Pharmacology Vol. 113, Springer-Verlag, New York Marks J D, Hoogenboom H R, Bonnert T P, McCafferty J, Griffiths A D, Winter G. By-passing immunization. Human antibodies from V-gene libraries displayed on phage. J Mol Biol. 1991 Dec. 5; 222(3):581-97. Links Milstein and Cuello, Hybrid hybridomas and their use in immunohistochemistry Nature 1983, 305:537-9

Mitchell, P G, et al. Cloning, expression, and type II collagenolytic activity of matrix metalloproteinase-13 from human osteoarthritic cartilage. J Clin Invest. 1996; 97:761-768.

Neuhold L A, Killar L, Zhao W, Sung M L, Warner L, Kulik J, Turner J, Wu W, Billinghurst C, Meijers T, Poole A R, Babij P, DeGennaro L J J; Postnatal expression in hyaline cartilage of constitutively active human collagenase-3 (MMP-13) induces osteoarthritis in mice. Clin Invest. 2001 January; 107(1):35-44.

O’Dell J R. Therapeutic strategies for rheumatoid arthritis, N Engl J Med. 2004; 350(25):2591-602.

Pei Y, Tuschl T. On the art of identifying effective and specific siRNAs, Nat Methods. 2006; 3(9):670-6.

Schmidt M R, Piekos B, Cabatingan M S, Woodland R T. Expression of a human coxsackie/adenovirus receptor transgene permits adenovirus infection of primary lymphocytes. J Immunol. 2000 165:4112-9.

Shlopov, B V, et al. Osteoarthritic lesions. Involvement of three different collagenases. Arthritis Rheum. 1997; 40:2065-2074.

Smolen J S, Steiner G. Therapeutic strategies for rheumatoid arthritis, Nat Rev Drug Discov. 2003; 2(6):473-88.

Traunecker A, Lanzavecchia A, Karjalainen K Bispecific single chain molecules (Janusins) target cytotoxic lymphocytes on HIV infected cells, EMBO J. 1991; 10(12): 3655-9.

Ventura M, Wang P, Ragot T, Perricaudet M, Saragosti S. Activation of HIV-specific ribozyme activity by self-cleavage, Nucleic Acids Res. 1993; 21(14):3249-55.

Wieland H A, Michaelis M, Kirschbaum B J, Rudolphi K A. “Osteoarthritis—an untreatable disease?”, Nat Rev Drug Discov. 2005; 4(4):331-44.

Wu W, Billinghurst R C, Pidoux I, Antoniou J, Zukor D, Tanzer M, Poole A R, Sites of collagenase cleavage and denaturation of type II collagen in aging and osteoarthritic articular cartilage and their relationship to the distribution of matrix metalloproteinase 1 and matrix metalloproteinase 13. Arthritis Rheum. 2002 August; 46(8):2087-94.

We claim:

1. A method for identifying a compound that inhibits type II collagen degradation in extracellular matrix (ECM) and/or cartilage, comprising:

(a) contacting a compound with a polypeptide comprising the amino acid sequence of SEQ ID NO: 29;

(b) selecting a compound that binds said polypeptide; and (c) measuring the ability of the compound selected in (b) to inhibit expression and/or activity of matrix metalloproteinase 13 (MMP13).

2. The method according to claim 1, wherein said polypeptide is in an in vitro cell-free preparation.

3. The method according to claim 1, wherein said polypeptide is present in a mammalian cell.

4. The method of claim 1, wherein the method is used to identify compounds that inhibit the catabolic process of chondrocytes.

5. The method of claim 1, which comprises the steps of:

c) contacting a population of mammalian cells expressing said polypeptide with one or more compound that exhibits a binding affinity for said polypeptide; and d) identifying a compound that inhibits expression and/or activity of MMP13 as a compound that inhibits type II collagen degradation in ECM and/or cartilage.

6. The method of claim 1 or 5, wherein the compound that binds said polypeptide has a binding affinity to the polypeptide of at least 10 micromolar.

7. The method according to claim 1, which additionally comprises the step of comparing the compound to be tested to a control.

8. The method according to claim 7, wherein said control is where the polypeptide has not been contacted with said compound.

9. The method according to claim 5, which additionally comprises the step of comparing the compound to a control, wherein said control is a population of mammalian cells that does not express said polypeptide.

10. The method according to claim 1 or 5, wherein said compound is selected from the group consisting of compounds of a commercially available screening library and compounds having binding affinity for a polypeptide comprising the amino acid sequence of SEQ ID NO: 29.

11. The method according to claim 1, wherein said compound is a peptide in a phage display library or an antibody fragment library.

* * * * *